(12) United States Patent
Bleicher et al.

(10) Patent No.: US 8,470,820 B2
(45) Date of Patent: Jun. 25, 2013

(54) NITROGEN-CONTAINING HETEROARYL DERIVATIVES

(75) Inventors: Konrad Bleicher, Freiburg (DE); Alexander Flohr, Loerrach (DE); Katrin Groebke Zbinden, Liestal (CH); Matthias Koerner, Grenzach-Wyhlen (DE); Bernd Kuhn, Reinach BL (CH); Jens-Uwe Peters, Grenzach-Wyhlen (DE); Rosa Maria Rodriguez-Sarmiento, Basel (CH); Eric Vieira, Frenkendorf (CH)

(73) Assignee: Hoffman-La Roche Inc., Nutley, NJ (US)

( * ) Notice: Subject to any disclaimer, the term of this patent is extended or adjusted under 35 U.S.C. 154(b) by 224 days.

(21) Appl. No.: 13/005,572

(22) Filed: Jan. 13, 2011

(65) Prior Publication Data
US 2011/0183979 A1    Jul. 28, 2011

(30) Foreign Application Priority Data
Jan. 22, 2010   (EP) ..................... 10151364

(51) Int. Cl.
| | | |
|---|---|---|
| *A61K 31/535* | (2006.01) | |
| *A61K 31/4965* | (2006.01) | |
| *C07D 239/42* | (2006.01) | |
| *C07D 403/14* | (2006.01) | |
| *C07D 413/12* | (2006.01) | |
| *C07D 239/02* | (2006.01) | |

(52) U.S. Cl.
USPC .............. 514/236.5; 514/255.05; 514/256; 544/122; 544/295; 544/296; 544/322

(58) Field of Classification Search
USPC ............. 514/236.5, 256, 255.05; 544/122, 544/295, 296, 322
See application file for complete search history.

(56) References Cited

U.S. PATENT DOCUMENTS
2006/0199960 A1   9/2006   Jaeschke et al.

FOREIGN PATENT DOCUMENTS
WO    2005/012485    2/2005

OTHER PUBLICATIONS

Lewis et al., Neuron. vol. 28 (2000) pp. 325-333.
Vandenberg et al., Exp. Opin. Ther, Targets vol. 5(4) (2001) pp. 507-518.
Nakazato et al., Exp. Opin Ther. Patents vol. 10(1) (2000) pp. 75-98.
PCT International Search Report—PCT/EP2011/050640—Issued: Jan. 19, 2011.
Sharma et al., Br. J. Psychiatry vol. 174 (Suppl. 28) (1999) pp. 44-51.
Javitt et al., Biol. Psychiatry vol. 45 (1999) pp. 668-679.
Beavo J., Physiol. Rev. vol. 75 (1995) pp. 725-748.
Conti et al., Progress in Nucleic Acid Resarch & Molecular Biology vol. 63 (1999) pp. 1-38.
Soderling et al., Curr. Opin. Cell Biol. vol. 12 (2000) pp. 174-179.
Manallack et al., J. Med. Chem. vol. 48(10) (2005) pp. 3449-3462.
Fujishige et al., Eur. J. Biochem. vol. 266(3) (1999) pp. 1118-1127.
Soderling et al., Proc. Natl. Acad. Sci. USA vol. 96(12) (1999) pp. 7071-7076.
Loughney t al., Gene vol. 234(1) (1999) pp. 109-117.
Fujishige et al., J. Biol. Chem. vol. 274 (1999) pp. 18438-18445.
Coskran et al., J. Histochem. Cytochem vol. 54(11) (2006) pp. 1205-1213.
Seeger et al., Brain Research vol. 985 (2003) pp. 113-126.
Graybiel A.M., Curr. Biol. vol. 10 (2000) pp. R509-R511.
Siuciak et al., Neuropharmacology vol. 51(2) (2006) pp. 386-396.
Siuciak et al., Neuropharmacology vol. 51(2) (2006) pp. 374-385.
Rodefer et al., Eur. J. Neuroscience vol. 21 (2005) pp. 1070-1076.
Sano H., J. Neurochem vol. 105(2) (2008) pp. 546-556.

*Primary Examiner* — James O Wilson
*Assistant Examiner* — Ebenezer O Sackey

(57) ABSTRACT

The invention is concerned with novel nitrogen-containing heteroaryl derivatives of formula (I)

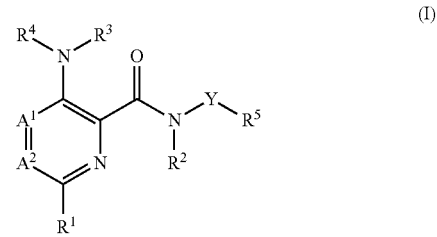

wherein $R^1$, $R^2$, $R^3$, $R^4$, $R^5$, $A^1$, $A^2$, and Y are as defined in the description and in the claims, as well as physiologically acceptable salts and esters thereof. These compounds inhibit PDE10A and can be used as medicaments.

18 Claims, No Drawings

NITROGEN-CONTAINING HETEROARYL DERIVATIVES

PRIORITY TO RELATED APPLICATION(S)

This application claims the benefit of European Patent Application No. 10151364.6, filed Jan. 22, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry*, 174 (*suppl.* 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididymal sperm (Coskran T. M, et al., *J. Histochem. Cytochem.* 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel nitrogen-containing heteroaryl derivatives of formula (I)

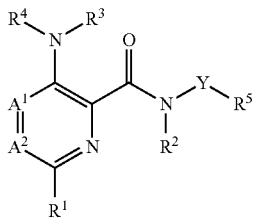

wherein
$A^1$ and $A^2$ are each independently selected from the group consisting of CH and N, provided that $A^1$ and $A^2$ are not simultaneously N;
$R^1$ is lower alkyl, lower alkoxy, lower hydroxyalkyl, lower haloalkyl, lower alkoxy lower alkyl, acetyl, lower alkyl-C(O)—, cyano, halogen, amino optionally substituted by 1 or 2 lower alkyl or lower alkoxy lower alkyl, cycloalkyl, or heterocyclyl;
$R^2$ and $R^3$ are each independently hydrogen or lower alkyl;
$R^4$ is heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl;
Y is 5-membered heteroaryl selected from the group consisting of:

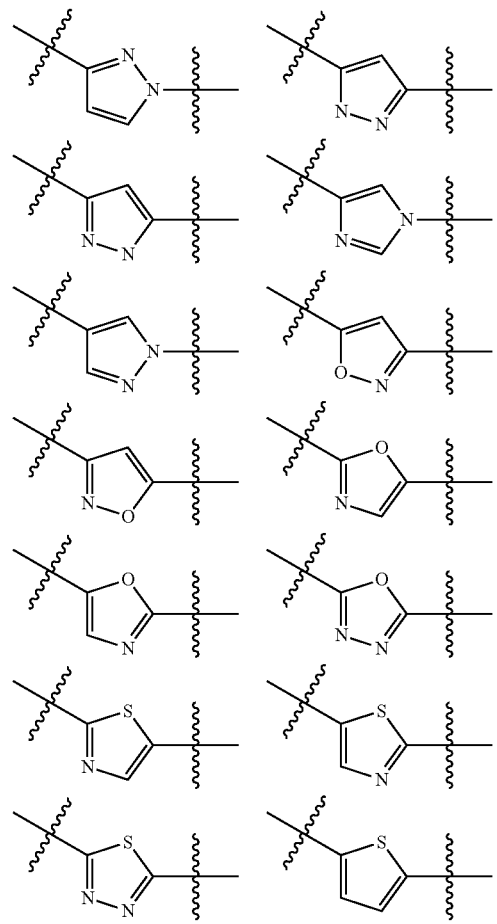

wherein said heteroaryl is optionally substituted by one substituent selected from the group consisting of
lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COOH, COO-lower alkyl, oxo, cyano and heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl,
cycloalkyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, and
heterocyclyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl; and
$R^5$ is selected from the group consisting of aryl and heteroaryl, wherein said aryl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, or pharmaceutically acceptable salts thereof.

Further, the invention provides a process for the manufacture of the above compounds, pharmaceutical compositions which contain such compounds as well as the use of these compounds for the production of pharmaceutical compositions.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower alkyl", alone or in combination with other groups, refers to a branched or straight-chain monovalent alkyl radical as defined above of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "lower haloalkyl" refers to lower alkyl groups which are mono- or multiply substituted with halogen. Examples of lower haloalkyl groups are e.g. $CFH_2$, $CF_2H$, $CF_3$, $CF_3CH_2$, $CF_3(CH_2)_2$, $(CF_3)_2CH$ and $CF_2H$—$CH_2$.

The term "alkoxy" refers to the group R'—O—, wherein R' is an alkyl group. The term "lower alkoxy" refers to the group R'—O—, wherein R' is a lower alkyl group.

The term "lower alkoxy lower alkyl" refers to lower alkyl groups which are mono- or multiply substituted with lower alkoxy. Examples of lower alkoxy lower alkyl groups are e.g. —$CH_2$—O—$CH_3$, —$CH_2$—$CH_2$—O—$CH_3$, and —$CH_2$—O—$CH_2$—$CH_3$.

The term "lower hydroxyalkyl" refers to a lower alkyl group as defined above, which is substituted by 1 to 3 hydroxy groups. Examples of lower hydroxyalkyl groups are e.g. hydroxy-methyl, 2-hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "amino" refers to a monovalent group that has a nitrogen atom with two hydrogen atoms (represented by —$NH_2$).

The term "heterocyclyl" refers to a monovalent saturated 5- to 6-membered monocyclic ring containing one, two or three ring heteroatoms selected from N, O and S, the remaining ring atoms being carbon atoms, wherein the point of attachment can be through either a carbon atom or a heteroatom. Examples of heterocycloalkyl are e.g. morpholinyl, tetrahydropyranyl and piperidinyl.

The term "aryl" refers to a monovalent aromatic hydrocarbon ring. The aryl group preferably includes $C_{6-10}$ aryl groups. Examples of aryl groups are e.g. phenyl, 1-naphthyl and 2-naphthyl.

The term "heteroaryl" refers to an aromatic 5 to 6 membered monocyclic ring or 9 to 10 membered bicyclic ring which comprises 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl and isoquinolinyl. Preferred heteroaryl groups are pyridinyl, pyrimidinyl, pyrazinyl, quinolinyl or imidazolyl.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

Compounds of formula (I) which comprise an acidic group, such as e.g. a COOH group, can further form salts with bases. Examples of such salts are alkaline, earth-alkaline and ammonium salts such as e.g. Na-, K-, Ca- and trimethylammonium salt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

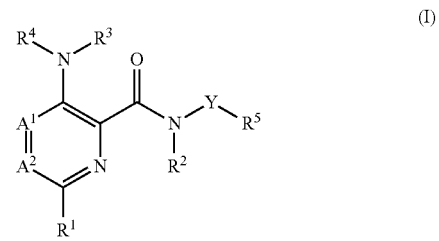

(I)

wherein $A^1$ and $A^2$ are each independently selected from the group consisting of CH and N, provided that $A^1$ and $A^2$ are not simultaneously N;

R¹ is lower alkyl, lower alkoxy, lower hydroxyalkyl, lower haloalkyl, lower alkoxy lower alkyl, acetyl, lower alkyl-C(O)—, cyano, halogen, amino optionally substituted by 1 or 2 lower alkyl or lower alkoxy lower alkyl, cycloalkyl, or heterocyclyl;

R² and R³ are each independently hydrogen or lower alkyl;

R⁴ is heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl;

Y is 5-membered heteroaryl selected from the group consisting of:

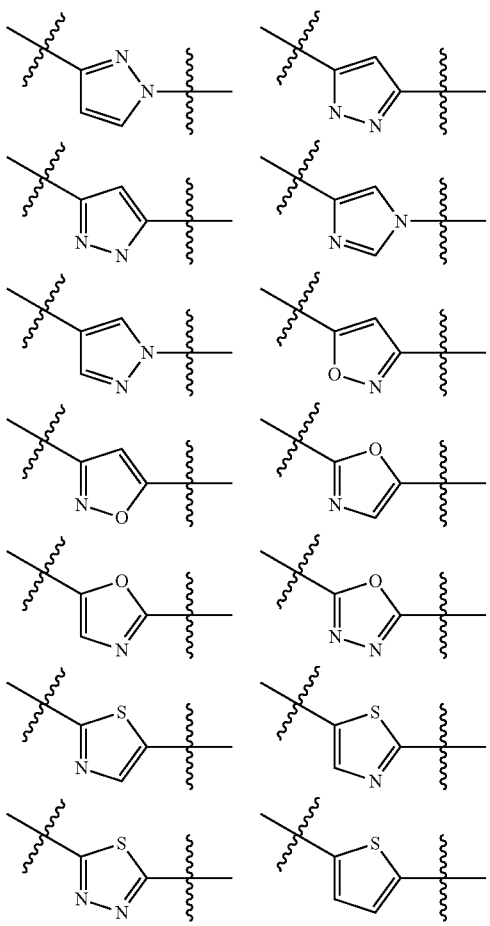

wherein said heteroaryl is optionally substituted by one substituent selected from the group consisting of lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COOH, COO-lower alkyl, oxo, cyano and heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, cycloalkyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, and heterocyclyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl; and R⁵ is selected from the group consisting of aryl and heteroaryl, wherein said aryl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, or pharmaceutically acceptable salts thereof.

The chemical structures of Y described above are attached to the amide nitrogen in formula (I) at their left side and attached to R⁵ at their right side.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

A preferred embodiment of the present invention relates to compounds of formula (I) as described above, wherein R¹ is lower alkyl, cycloalkyl or lower alkoxy lower alkyl, and more preferably methyl, ethyl, isopropyl, isobutyl, tert-butyl, cyclopropyl, cyclohexyl or methoxymethyl.

Another preferred embodiment of the present invention relates to compounds of formula (I) as described above, wherein R² and R³ are hydrogen.

In another preferred embodiment of the present invention, R⁴ is pyrimidinyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl. Compounds, wherein R⁴ is pyrimidin-5-yl, are more preferred.

Other preferred compounds according to the present invention are those, wherein R⁵ is phenyl or 6- or 10-membered heteroaryl containing one or two nitrogen, wherein said phenyl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl. Compounds, wherein R⁵ is phenyl, pyridinyl, pyrazinyl, or quinolinyl optionally substituted by substituents as defined above, are more preferred. Among the substituents as defined above, halogen and lower alkoxy are more preferred. Further more preferably, R⁵ is phenyl, 2-fluoro-phenyl, 4-fluoro-phenyl, 4-chloro-phenyl, 4-bromo-phenyl, 4-methoxy-phenyl, pyridin-2-yl, pyridin-4-yl, 5-chloro-pyridin-2-yl, 6-chloro-pyridin-2-yl, pyrazin-2-yl or quinolin-2-yl.

Other preferred compounds according to the present invention are those, wherein Y is selected from the group consisting of:

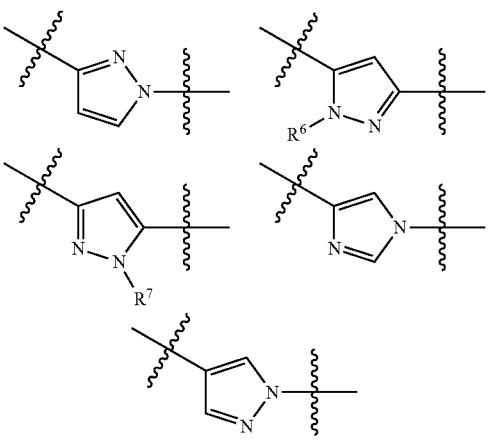

wherein R⁶ is selected from the group consisting of lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COO-lower alkyl, cyano and heteroaryl optionally substituted by lower alkyl, cycloalkyl, and
heterocyclyl optionally substituted by 1 to 3 substituents selected from the group consisting of lower alkyl, and
R⁷ is lower alkyl or lower alkyl substituted by amino optionally substituted by one or two lower alkyl.

More preferably, R⁶ is methyl, ethyl, propyl, isopropyl, isobutyl, tert-butyl, 2,2,2-trifluoro-ethyl, 2-hydroxy-ethyl, 2-methoxy-ethyl, —CH₂COOC₂H₅, 2-dimethylamino-ethyl, 2-cyano-ethyl, cyclopentylmethyl, cyclohexyl, cyclohexylmethyl, tetrahydro-pyran-4-yl, 1-methyl-piperidin-4-yl, 2-morpholin-4-yl-ethyl, benzyl, 2-phenylethyl or 3-methyl-3H-imidazol-4-ylmethyl, and R⁷ is methyl or 2-dimethylamino-ethyl.

Other preferred compounds according to the present invention are those, wherein Y is selected from the group consisting of:

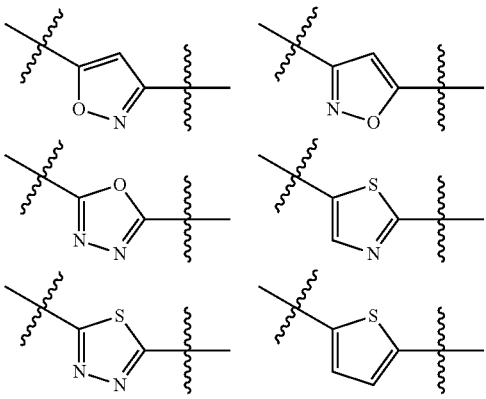

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:
6-Methyl-3-(pyrimidin-5-ylamino)-pyridine-2-carboxylic acid (1-phenyl-1H-pyrazol-3-yl)-amide,
6-Methyl-3-(pyrimidin-5-ylamino)-pyridine-2-carboxylic acid [1-(4-fluoro-phenyl)-1H-pyrazol-3-yl]-amide,
6-Methyl-3-(pyrimidin-5-ylamino)-pyridine-2-carboxylic acid [1-(2-fluoro-phenyl)-1H-pyrazol-3-yl]-amide,
6-Methyl-3-(pyrimidin-5-ylamino)-pyridine-2-carboxylic acid (1-pyridin-2-yl-1H-pyrazol-3-yl)-amide,
6-Methyl-3-(pyrimidin-5-ylamino)-pyridine-2-carboxylic acid (1-pyridin-4-yl-1H-pyrazol-3-yl)-amide,
6-Cyclopropyl-3-(pyrimidin-5-ylamino)-pyridine-2-carboxylic acid [1-(4-fluoro-phenyl)-1H-pyrazol-3-yl]-amide,
6-Cyclopropyl-3-(pyrimidin-5-ylamino)-pyridine-2-carboxylic acid (1-pyridin-4-yl-1H-pyrazol-3-yl)-amide,
6-Cyclopropyl-3-(pyrimidin-5-ylamino)-pyridine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [2-(2-hydroxy-ethyl)-5-phenyl-2H-pyrazol-3-yl]-amide,
6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide,
6-Methoxymethyl-3-(pyrimidin-5-ylamino)-pyridine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(2-dimethylamino-ethyl)-5-pyridin-2-yl-2H-pyrazol-3-yl]-amide,
2-Methoxymethyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid (2-cyclohexyl-5-pyridin-2-yl-2H-pyrazol-3-yl)-amide,
(5-{[6-Cyclopropyl-3-(pyrimidin-5-ylamino)-pyridine-2-carbonyl]-amino}-3-pyridin-2-yl-pyrazol-1-yl)-acetic acid ethyl ester,
6-Cyclopropyl-3-(pyrimidin-5-ylamino)-pyridine-2-carboxylic acid [2-(2-morpholin-4-yl-ethyl)-5-pyridin-2-yl-2H-pyrazol-3-yl]-amide,
6-Cyclopropyl-3-(pyrimidin-5-ylamino)-pyridine-2-carboxylic acid (2-phenethyl-5-pyridin-2-yl-2H-pyrazol-3-yl)-amide,
6-Cyclopropyl-3-(pyrimidin-5-ylamino)-pyridine-2-carboxylic acid (2-tert-butyl-5-pyridin-2-yl-2H-pyrazol-3-yl)-amide,
6-Ethyl-3-(pyrimidin-5-ylamino)-pyridine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [5-pyridin-2-yl-2-(tetrahydro-pyran-4-yl)-2H-pyrazol-3-yl]-amide,
6-Cyclopropyl-3-(pyrimidin-5-ylamino)-pyrazine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [5-pyridin-2-yl-2-(2,2,2-trifluoro-ethyl)-2H-pyrazol-3-yl]-amide,
6-Cyclopropyl-3-(pyrimidin-5-ylamino)-pyridine-2-carboxylic acid (2-propyl-5-pyridin-2-yl-2H-pyrazol-3-yl)-amide,
6-Cyclopropyl-3-(pyrimidin-5-ylamino)-pyridine-2-carboxylic acid [5-(6-chloro-pyridin-2-yl)-2-(2-hydroxy-ethyl)-2H-pyrazol-3-yl]-amide, 6-Cyclopropyl-3-(pyrimidin-5-ylamino)-pyridine-2-carboxylic acid [2-(2-hydroxy-ethyl)-5-quinolin-2-yl-2H-pyrazol-3-yl]-amide,
6-Cyclopropyl-3-(pyrimidin-5-ylamino)-pyridine-2-carboxylic acid [5-(5-chloro-pyridin-2-yl)-2-(2-hydroxy-ethyl)-2H-pyrazol-3-yl]-amide,
6-Cyclopropyl-3-(pyrimidin-5-ylamino)-pyridine-2-carboxylic acid (2-isopropyl-5-pyridin-2-yl-2H-pyrazol-3-yl)-amide,
6-Cyclopropyl-3-(pyrimidin-5-ylamino)-pyridine-2-carboxylic acid (2-isobutyl-5-pyridin-2-yl-2H-pyrazol-3-yl)-amide,
6-Cyclopropyl-3-(pyrimidin-5-ylamino)-pyridine-2-carboxylic acid (2-benzyl-5-pyridin-2-yl-2H-pyrazol-3-yl)-amide,
6-Cyclopropyl-3-(pyrimidin-5-ylamino)-pyridine-2-carboxylic acid (2-ethyl-5-pyridin-2-yl-2H-pyrazol-3-yl)-amide,
6-Cyclopropyl-3-(pyrimidin-5-ylamino)-pyridine-2-carboxylic acid (2-cyclopentylmethyl-5-pyridin-2-yl-2H-pyrazol-3-yl)-amide,
6-Cyclopropyl-3-(pyrimidin-5-ylamino)-pyridine-2-carboxylic acid (2-cyclohexylmethyl-5-pyridin-2-yl-2H-pyrazol-3-yl)-amide,
6-Cyclopropyl-3-(pyrimidin-5-ylamino)-pyridine-2-carboxylic acid [2-(2-cyano-ethyl)-5-pyridin-2-yl-2H-pyrazol-3-yl]-amide,
6-Ethyl-3-(pyrimidin-5-ylamino)-pyridine-2-carboxylic acid [2-(2-hydroxy-ethyl)-5-pyridin-2-yl-2H-pyrazol-3-yl]-amide,
6-Methyl-3-(pyrimidin-5-ylamino)-pyrazine-2-carboxylic acid (2-methyl-5-pyridin-2-yl-2H-pyrazol-3-yl)-amide,
6-Methyl-3-(pyrimidin-5-ylamino)-pyrazine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(3-methyl-3H-imidazol-4-ylmethyl)-5-pyridin-2-yl-2H-pyrazol-3-yl]-amide,
6-Cyclopropyl-3-(pyrimidin-5-ylamino)-pyridine-2-carboxylic acid [2-(2-methoxy-ethyl)-5-pyridin-2-yl-2H-pyrazol-3-yl]-amide,
6-Cyclopropyl-3-(pyrimidin-5-ylamino)-pyridine-2-carboxylic acid [5-(5-chloro-pyridin-2-yl)-2-methyl-2H-pyrazol-3-yl]-amide,
6-Cyclopropyl-3-(pyrimidin-5-ylamino)-pyridine-2-carboxylic acid (2-methyl-5-quinolin-2-yl-2H-pyrazol-3-yl)-amide,
6-Cyclopropyl-3-(pyrimidin-5-ylamino)-pyridine-2-carboxylic acid [5-(6-chloro-pyridin-2-yl)-2-methyl-2H-pyrazol-3-yl]-amide,
6-Cyclopropyl-3-(pyrimidin-5-ylamino)-pyridine-2-carboxylic acid [1-(2-dimethylamino-ethyl)-5-pyridin-2-yl-1H-pyrazol-3-yl]-amide,
6-Cyclopropyl-3-(pyrimidin-5-ylamino)-pyridine-2-carboxylic acid [2-(1-methyl-piperidin-4-yl)-5-pyridin-2-yl-2H-pyrazol-3-yl]-amide,
6-Cyclopropyl-3-(pyrimidin-5-ylamino)-pyridine-2-carboxylic acid [5-(4-methoxy-phenyl)-[1,3,4]thiadiazol-2-yl]-amide,
6-Cyclopropyl-3-(pyrimidin-5-ylamino)-pyridine-2-carboxylic acid [5-(4-fluoro-phenyl)-[1,3,4]thiadiazol-2-yl]-amide,
6-Cyclopropyl-3-(pyrimidin-5-ylamino)-pyridine-2-carboxylic acid (3-phenyl-isoxazol-5-yl)-amide,
6-Cyclopropyl-3-(pyrimidin-5-ylamino)-pyridine-2-carboxylic acid (5-phenyl-isoxazol-3-yl)-amide,
6-Cyclopropyl-3-(pyrimidin-5-ylamino)-pyridine-2-carboxylic acid (5-phenyl-[1,3,4]thiadiazol-2-yl)-amide,
6-Cyclopropyl-3-(pyrimidin-5-ylamino)-pyridine-2-carboxylic acid (5-pyrazin-2-yl-[1,3,4]thiadiazol-2-yl)-amide,
6-Cyclopropyl-3-(pyrimidin-5-ylamino)-pyridine-2-carboxylic acid (5-pyridin-2-yl-thiophen-2-yl)-amide,
6-Cyclopropyl-3-(pyrimidin-5-ylamino)-pyridine-2-carboxylic acid (3-pyridin-2-yl-isoxazol-5-yl)-amide,
6-Cyclopropyl-3-(pyrimidin-5-ylamino)-pyridine-2-carboxylic acid (1-pyridin-2-yl-1H-imidazol-4-yl)-amide,
2-Isopropyl-5-(pyrimidin-5-ylamino)-pyrimidine-4-carboxylic acid (2-methyl-5-pyridin-2-yl-2H-pyrazol-3-yl)-amide,
2-Cyclopropyl-5-(pyrimidin-5-ylamino)-pyrimidine-4-carboxylic acid (2-methyl-5-pyridin-2-yl-2H-pyrazol-3-yl)-amide,
2-tert-Butyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [3-(4-chloro-phenyl)-isoxazol-5-yl]-amide,
6-Cyclopropyl-3-(pyrimidin-5-ylamino)-pyridine-2-carboxylic acid [3-(4-bromo-phenyl)-isoxazol-5-yl]-amide,
6-Cyclopropyl-3-(pyrimidin-5-ylamino)-pyridine-2-carboxylic acid [3-(4-fluoro-phenyl)-isoxazol-5-yl]-amide,
6-Methoxymethyl-3-(pyrimidin-5-ylamino)-pyridine-2-carboxylic acid (2-methyl-5-pyridin-2-yl-2H-pyrazol-3-yl)-amide,
2-Cyclohexyl-5-(pyrimidin-5-ylamino)-pyrimidine-4-carboxylic acid (2-methyl-5-pyridin-2-yl-2H-pyrazol-3-yl)-amide,
2-Isobutyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid (2-pyridin-2-yl-thiazol-5-yl)-amide,
6-Cyclopropyl-3-(pyrimidin-5-ylamino)-pyridine-2-carboxylic acid (1-methyl-5-pyridin-2-yl-1H-pyrazol-3-yl)-amide,
6-Cyclopropyl-3-(pyrimidin-5-ylamino)-pyridine-2-carboxylic acid (5-pyridin-2-yl-[1,3,4]oxadiazol-2-yl)-amide,
6-Cyclopropyl-3-(pyrimidin-5-ylamino)-pyridine-2-carboxylic acid (1-pyridin-2-yl-1H-pyrazol-4-yl)-amide, and
6-Cyclopropyl-3-(pyrimidin-5-ylamino)-pyrazine-2-carboxylic acid (1-pyridin-2-yl-1H-imidazol-4-yl)-amide,
or pharmaceutically acceptable salts thereof.

Particularly preferred compounds of formula (I) are those selected from the group consisting of:
6-Cyclopropyl-3-(pyrimidin-5-ylamino)-pyridine-2-carboxylic acid [1-(4-fluoro-phenyl)-1H-pyrazol-3-yl]-amide,
6-Cyclopropyl-3-(pyrimidin-5-ylamino)-pyridine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide,
6-Methoxymethyl-3-(pyrimidin-5-ylamino)-pyridine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(2-dimethylamino-ethyl)-5-pyridin-2-yl-2H-pyrazol-3-yl]-amide, 6-Cyclopropyl-3-(pyrimidin-5-ylamino)-pyridine-2-carboxylic acid [2-(2-morpholin-4-yl-ethyl)-5-pyridin-2-yl-2H-pyrazol-3-yl]-amide, 6-Cyclopropyl-3-(pyrimidin-5-ylamino)-pyridine-2-carboxylic acid [5-pyridin-2-yl-2-(tetrahydro-pyran-4-yl)-2H-pyrazol-3-yl]-amide, 6-Cyclopropyl-3-(pyrimidin-5-ylamino)-pyrazine-2-carboxylic acid (2-methyl-5-pyridin-2-yl-2H-pyrazol-3-yl)-amide, 6-Ethyl-3-(pyrimidin-5-ylamino)-pyridine-2-carboxylic acid [2-(2-hydroxy-ethyl)-5-pyridin-2-yl-2H-pyrazol-3-yl]-amide, 6-Methyl-3-(pyrimidin-5-ylamino)-pyrazine-2-carboxylic acid [2-(2-hydroxy-ethyl)-5-pyridin-2-yl-2H-pyrazol-3-yl]-amide, 6-Cyclopropyl-3-(pyrimidin-5-ylamino)-pyridine-2-carboxylic acid [2-(2-methoxy-ethyl)-5-pyridin-2-yl-2H-pyrazol-3-yl]-amide, 6-Cyclopropyl-3-(pyrimidin-5-ylamino)-pyridine-2-carboxylic acid [5-(5-chloro-pyridin-2-yl)-2-methyl-2H-pyrazol-3-yl]-amide, 6-Cyclopropyl-3-(pyrimidin-5-ylamino)-pyridine-2-carboxylic acid (5-pyridin-2-yl-thiophen-2-yl)-amide, 6-Cyclopropyl-3-(pyrimidin-5-ylamino)-pyridine-2-carboxylic acid (3-pyridin-2-yl-isoxazol-5-yl)-amide, 6-Cyclopropyl-3-(pyrimidin-5-ylamino)-pyridine-2-carboxylic acid (1-pyridin-2-yl-1H-imidazol-4-yl)-amide, 2-tert-Butyl-5-(pyrimidin-5-ylamino)-pyrimidine-4-carboxylic acid (2-methyl-5-pyridin-2-yl-2H-pyrazol-3-yl)-amide, 6-Methoxymethyl-3-(pyrimidin-5-ylamino)-pyridine-2-carboxylic acid (2-methyl-5-pyridin-2-yl-2H-pyrazol-3-yl)-amide, 2-Isobutyl-5-(pyrimidin-5-ylamino)-pyrimidine-4-carboxylic acid (2-methyl-5-pyridin-2-yl-2H-pyrazol-3-yl)-amide, and 6-Cyclopropyl-3-(pyrimidin-5-ylamino)-pyridine-2-carboxylic acid (2-pyridin-2-yl-thiazol-5-yl)-amide, or pharmaceutically acceptable salts thereof.

It will be appreciated that the compounds of general formula (I) in this invention can be derivatized at functional groups to provide derivatives which are capable of conversion back to the parent compound in vivo.

The invention further relates to a process for the manufacture of compounds of formula (I) as defined above, which process comprises:

a) reacting a compound of formula (IV) or formula (IVa)

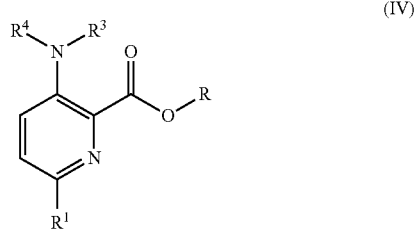
(IV)

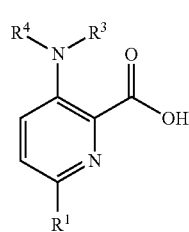
(IVa)

with a compound of formula (XIV)

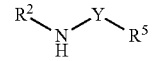
(XIV)

wherein R is lower alkyl, and $R^1$, $R^2$, $R^3$, $R^4$, and $R^5$ are as described above, and if desired, converting the compounds into pharmaceutical acceptable salts thereof;

b) reacting a compound of formula (VII) or the free acid thereof

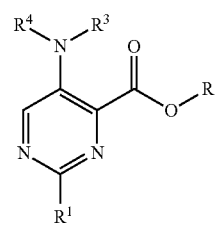
(VII)

with a compound of formula (XIV)

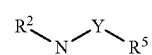
(XIV)

wherein R is lower alkyl, and $R^1$, $R^2$, $R^3$, $R^4$, and $R^5$ are as described above, and if desired, converting the compounds into pharmaceutical acceptable salts thereof;

c) reacting a compound of formula (VIII)

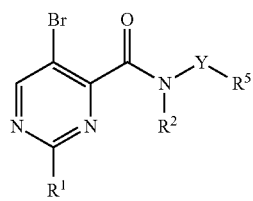
(VIII)

with a compound of formula (XV)

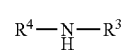
(XV)

wherein $R^1$, $R^2$, $R^3$, $R^4$, and $R^5$ are as described above, and if desired, converting the compounds into pharmaceutical acceptable salts thereof; or d) reacting a compound of formula (XIII) or formula (XIIIa)

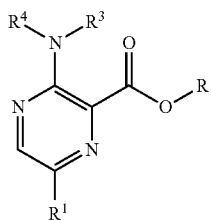

(XIII)

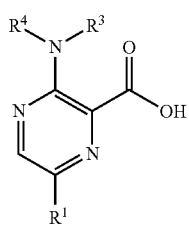

(XIIIa)

with a compound of formula (XIV)

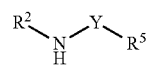

(XIV)

wherein R is lower alkyl, and $R^1$, $R^2$, $R^3$, $R^4$, and $R^5$ are as described above, and if desired, converting the compounds into pharmaceutical acceptable salts thereof.

The reaction described above can be carried out under conditions as described in the description and examples or under conditions well known to the person skilled in the art.

The compounds of formula (IV), (IVa), (VII), (VIII), (XIII), (XIIIa), (XIV) and (XV) can be prepared by methods known in the art or as described below or in analogy thereto. Unless otherwise indicated, R is lower alkyl, and $R^1$, $R^2$, $R^3$, $R^4$, and $R^5$ are as described above.

The present invention also relates to compounds of formula (I) as defined above, when prepared by a process as described above.

Compounds of general formula (I) wherein $A^1$ and $A^2$ are CH can be prepared according to the general methods described in US 2006/0199960 and as outlined in schemes 1 and 2 and in general procedures 1, 2a and 2b.

Scheme 1

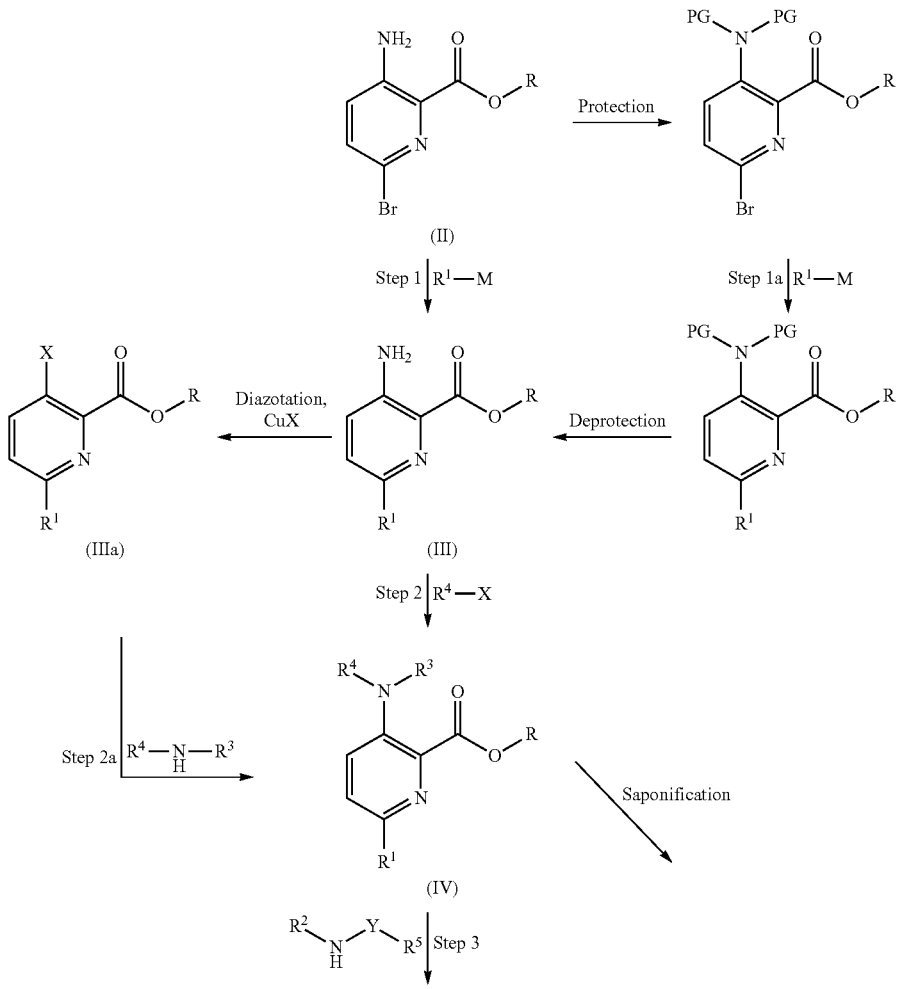

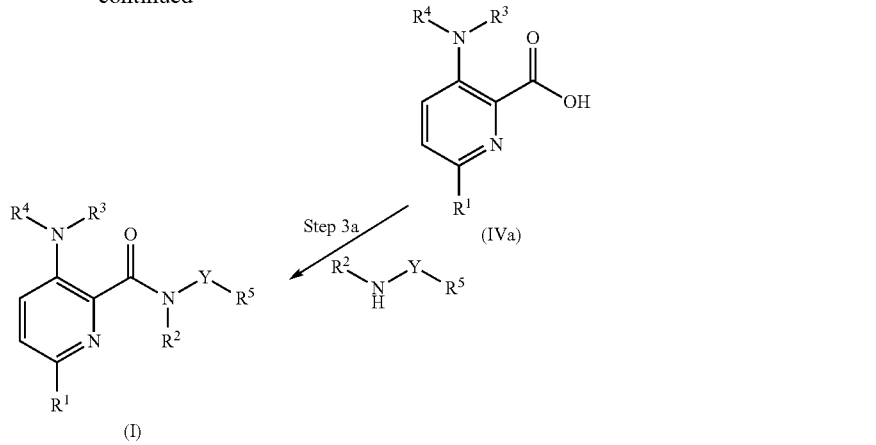

General Procedure 1:

Step 1:

Compounds of formula (II) wherein R is lower alkyl are commercially available or can be prepared starting from pyridine-2,3-dicarboxylic acid according to US 2006/0199960. Compounds of formula (II) can be converted to a compound of formula (III) by a Pd-catalyzed coupling reaction with an organometallic reagent $R^1$-M (e.g. organoboronic acid or organoboronic acid ester) using a Pd-catalyst (e.g. $Pd_2(dba)_2$) and a base (e.g. potassium phosphate) in an organic solvent (e.g. dioxane). Compounds of formula (III) can be isolated and purified by conventional methods.

The compound of formula (II) wherein R is H is commercially available or can be prepared according to in WO 2008/106692 and can be transformed to the compound of formula (II) wherein R is lower alkyl by standard methods of ester formation known to those skilled in the art.

Step 1a:

Compounds of formula (II) wherein R is lower alkyl can also be converted to a compound of formula (III) according to the methods described in US 2006/0199960 by i) protection of the amino group with a suitable protective group (e.g. Boc) using e.g. di-tert-butyl-dicarbonate in the presence of an organic or inorganic base (e.g. DMAP or triethylamine) in an organic solvent, ii) Pd-catalyzed coupling reaction with an organometallic reagent $R^1$-M (e.g. organozinc reagent or organotin reagent) using a Pd-catalyst (e.g. $Pd(PPh_3)_4$) and a base (e.g. potassium carbonate) in an organic solvent (e.g. dioxane), and iii) deprotection of the amino group using e.g. an organic or inorganic acid (e.g. HCl or trifluoroacetic acid) in an organic solvent. Compounds of formula (III) can be isolated and purified by conventional methods.

Step 2:

A compound of formula (IV) can be obtained by e.g. a Pd-catalyzed arylation of the amino group of compounds of formula (III) using aryl halides or heteroaryl halides (e.g. 5-bromopyrimidine) $R^4$—X, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). Compounds of formula (IV) can be isolated and purified by conventional methods.

Step 2a:

Compounds of formula (IIIa) wherein R is lower alkyl can be prepared according to US 2006/0199960. Alternatively, compounds of formula (III) can be converted to a compound of formula (IIIa) wherein X is a halogen by diazotation using e.g. sodium nitrite or tert-butyl nitrite and subsequent substitution using a suitable copper halide. The compound of formula (IV) can then be obtained by e.g. a Pd-catalyzed amination of compound (IIIa) using arylamines or heteroarylamines (e.g. 5-aminopyrimidine) $R^4$—NH—$R^3$, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). Compounds of formula (IV) can be isolated and purified by conventional methods.

Step 3:

A compound of formula (IV) can be converted to a compound of formula (I) by direct aminolysis of the ester group using heteroarylamines $R^5$—Y—NH—$R^2$ and a Lewis acid (e.g. trimethylaluminium or dimethylaluminium chloride) in an organic solvent (e.g. toluene or dioxane). Compounds of formula (I) can be isolated and purified by conventional methods. Heteroarylamines $R^5$—Y—NH—$R^2$ are commercially available or can be prepared by standard methods known to those skilled in the art and as described at the respective examples.

Step 3a:

Alternatively, the ester group of a compound of formula (IV) can be saponified to its free acid (IVa) using an inorganic base (e.g. lithium hydroxide, sodium hydroxide) in an organic solvent (e.g. ethanol, dioxane, THF) or a mixture thereof. A compound of formula (IVa) can then be converted to a compound of formula (I) by amide bond formation using heteroarylamines $R^5$—Y—NH—$R^2$, a coupling reagent (e.g. propylphosphonic acid anhydride, HATU, TBTU) and an organic base (e.g. N,N-diisopropylethylamine, N-methylmorpholine or triethylamine) in an organic solvent (e.g. DMF, ethyl acetate, THF). Compounds of formula (I) can be isolated and purified by conventional methods.

Compounds of general formula (I) wherein $A^1$ and $A^2$ are CH that can not be synthesized as outlined in scheme 1 and in general procedure 1 can be prepared from intermediates of general formula (IIIb) or (IIIc) as outlined in scheme 2 and in general procedures 2a and 2b.

Scheme 2

General Procedure 2a:

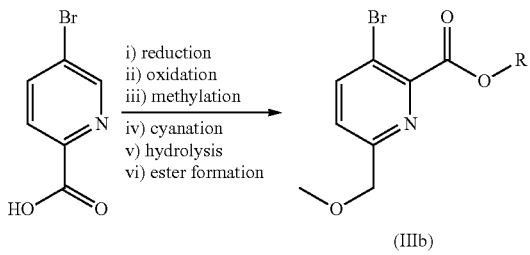

General Procedure 2b:

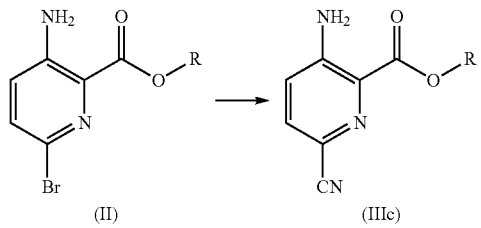

General Procedure 2a:

Starting from commercially available 5-bromopyridine-2-carboxylic acid, a 5-bromo-2-methoxymethyl-pyridine-2-carboxylate intermediate of formula (IIIb) can be prepared by:

i) reduction of carboxylate using a reducing agent (e.g. sodium borohydride, borane-dimethylsulphide) in an organic solvent (e.g. THF)
ii) oxidation of pyridine to pyridine-N-oxide using an oxidizing reagent (e.g. m-chlorobenzoic acid) in an organic solvent (e.g. dichloromethane)
iii) alkylation of hydroxyl group using an alkylating reagent (e.g. methyl iodide) and a suitable inorganic base (e.g. sodium hydride) in an organic solvent (e.g. THF or dioxane)
iv) cyanation of pyridinium-N-oxide using e.g. cyanotrimethylsilane, a suitable base (e.g. triethylamine) in an organic solvent (e.g. acetonitrile or DMF)
v) hydrolysis of nitrile to result in free acid using a strong inorganic base (e.g. potassium hydroxide) in an organic solvent (e.g. methanol or ethanol)
vi) ester formation of acid group using e.g. an alcohol in the presence of a strong acid, an alkylhalide in the presence of a base or special alkylating reagents (e.g. trimethylsilyl-diazomethane).
vii) Intermediates of formula (IIIb) can be further converted to compounds of general formula (I) by the general methods described above.

General Procedure 2b:

Starting from compounds of formula (II) wherein R is lower alkyl, a 3-amino-6-cyano-pyridine-2-carboxylate intermediate of formula (IIIc) can be prepared by replacement of the bromine by a nitrile group using e.g. copper (I) cyanide in an organic solvent as e.g. DMF. This intermediate can either be converted to compounds of general formula (I) by the general methods described above. Or the nitrile group can be further converted to e.g. a carboxylic acid (via hydrolysis), an alkyl carboxylate (via hydrolysis and ester formation), an alcohol (via hydrolysis and reduction), a ketone (via hydrolysis, activation as e.g. Weinreb amide and alkylation with e.g. a Grignard reagent), or an amino group (via hydrolysis and Curtius reaction) which can be further substituted by e.g. alkyl groups on the stage of either the different intermediates or the final products. These intermediates can be further converted to compounds of general formula (I) by the general methods described above.

Compounds of general formula (I) wherein $A^1$ is CH and $A^2$ is N can be prepared as outlined in schemes 3 and 4 and in general procedures 3 and 4.

Scheme 3

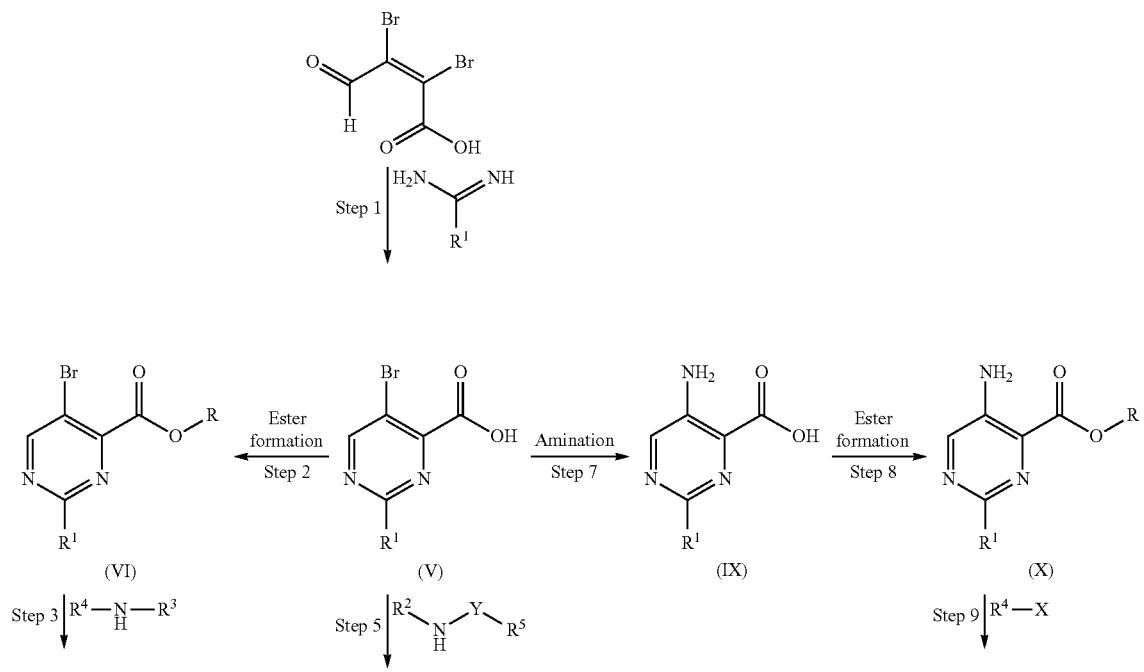

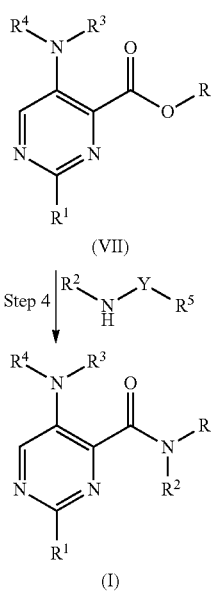

(VII)

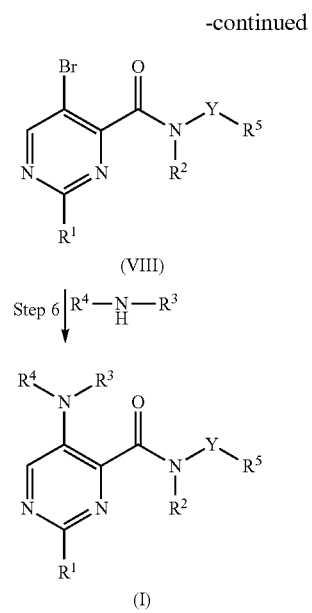

(VIII)

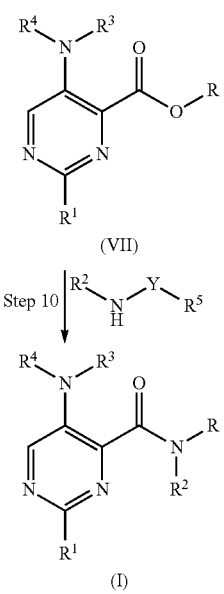

(VII)

General Procedure 3:

Step 1:
Compounds of formula (V) are commercially available or can be prepared according to the general methods described in e.g. WO 2000/066566 or WO 2005/021500 by condensation of e.g. mucobromic acid with a suitable amidine containing residue $R^1$ in the presence of an organic base (e.g. sodium ethylate) in an organic solvent (e.g. ethanol) at ambient or elevated temperatures.

Step 2:
A compound of formula (V) can be converted to compounds of formula (VI) wherein R is lower alkyl by formation of an ester using e.g. an alcohol in the presence of a strong acid, an alcohol in the presence of an acid chloride-forming reagent (e.g. thionyl chloride), an alkylhalide in the presence of a base or special alkylating reagents (e.g. trimethylsilyldiazomethane). Compounds of formula (VI) can be isolated and purified by conventional methods.

Step 3:
A compound of formula (VII) can be obtained by e.g. a Pd-catalyzed arylation of the amino group of (VI) using aryl amines or heteroaryl amines (e.g. 5-aminopyrimidine) $R^4$—NH—$R^3$, a Pd-catalyst (e.g. PdOAc$_2$), a suitable ligand (e.g. 4,5-bis(diphenyl-phosphino)-9,9-dimethylxanthene) and a base (e.g. potassium carbonate) in an organic solvent (e.g. toluene, o-xylene). Compounds of formula (VII) can be isolated and purified by conventional methods.

Step 4:
A compound of formula (VII) can be converted to a compound of formula (I) by direct aminolysis of the ester group using heteroarylamines $R^5$—Y—NH—$R^2$ and a Lewis acid (e.g. trimethylaluminium or dimethylaluminium chloride) in an organic solvent (e.g. toluene or dioxane). Compounds of formula (I) can be isolated and purified by conventional methods.

Alternatively, a compound of formula (VII) can be saponified to its free acid using an inorganic base (e.g. lithium hydroxide, sodium hydroxide) in an organic solvent (e.g. ethanol, dioxane, THF) or a mixture thereof. The free acid of a compound of formula (VII) can then be converted to compounds of formula (I) by amide bond formation using heteroarylamines $R^5$—Y—NH—$R^2$, a coupling reagent (e.g. propylphosphonic acid anhydride, HATU, TBTU) and an organic base (e.g. N,N-diisopropylethylamine, N-methylmorpholine or triethylamine) in an organic solvent (e.g. DMF, ethyl acetate, THF).

Step 5:
A compound of formula (V) can be converted to compounds of formula (VIII) according to the method described in step 4 for the conversion of acids of formula (VII).

Step 6:
A compound of formula (VIII) can be converted to a compound of formula (I) according to the method described in step 3 for the formation of compounds of formula (VII).

Step 7:
A compound of formula (V) can be converted to compounds of formula (IX) by amination of the bromide using an ammonia source (e.g. ammonium hydroxide) in the presence of a transition metal (e.g. copper (II) sulfate) in a solvent like water.

Step 8:
A compound of formula (IX) can be converted to compounds of formula (X) according to the method described in step 2 for the formation of compounds of formula (VI).

Step 9:
A compound of formula (X) can be converted to compounds of formula (VII) according to the method described in step 3 for the formation of compounds of formula (VII) using aryl halides or heteroaryl halides (e.g. 5-bromopyrimidine) $R^4$—X.

Step 10:
A compound of formula (XI) can be converted to compounds of formula (I) according to the method described in step 4 for the conversion of compounds of formula (VII).

Compounds of general formula (VI) wherein $A^1$ is CH and $A^2$ is N and R is H or lower alkyl that can not be synthesized as outlined in scheme 3 and in general procedure 3 can be prepared e.g from commercially available intermediates of general formula (VIa) as outlined in scheme 4 and in general procedure 4.

Scheme 4

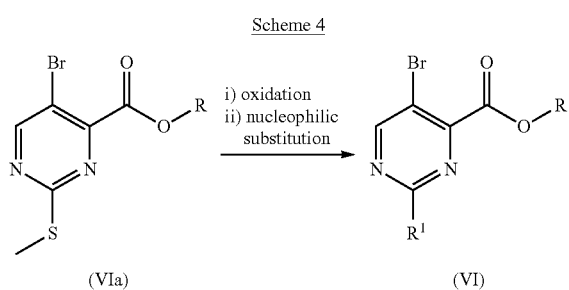

General Procedure 4:

Starting from commercially available 5-bromo-2-methylthio-pyrimidine-4-carboxylates of general formula (VIa), intermediates of formula VI wherein $R^1$ is alkoxy or optionally substituted amine can be prepared by:

i) oxidation of the methylthio group using an oxidizing reagent (e.g. 3-chloroperbenzoic acid) in an organic solvent (e.g. methylenechloride) to form a methylsulphone group ii) nucleophilic substitution of the methylsulphone group by oxygen or nitrogen nucleophiles (e.g. alkylamine or alkylalcohol) in an organic solvent (e.g. methylenechloride) to yield intermediates (VI).

iii) These intermediates can be further converted to compounds of general formula (I) by the general methods described above.

Compounds of general formula (I) wherein $A^1$ is N and $A^2$ is CH can be prepared according to the general methods described in US 2006/0199828 and as outlined in scheme 5 and in general procedure 5.

Scheme 5

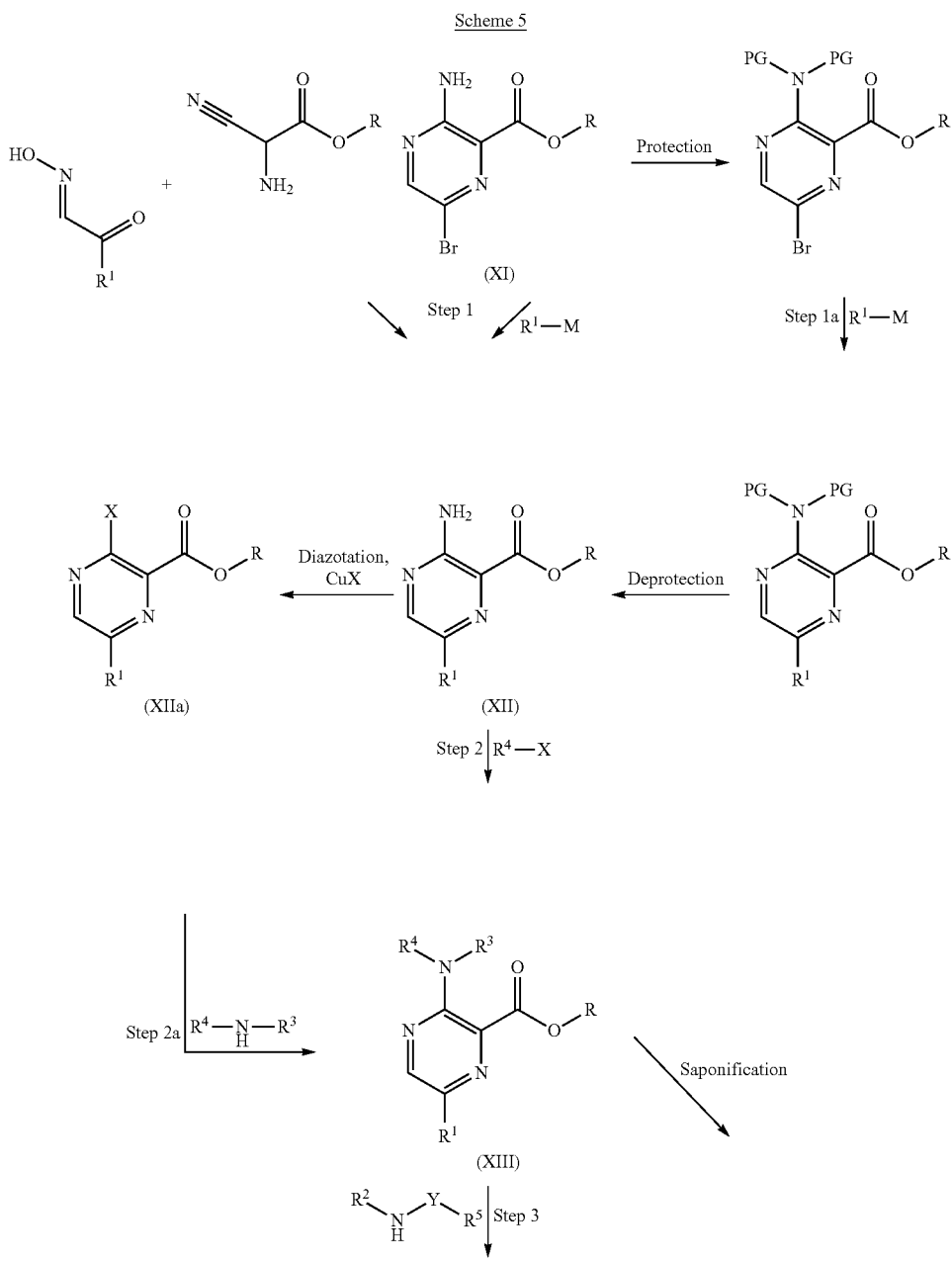

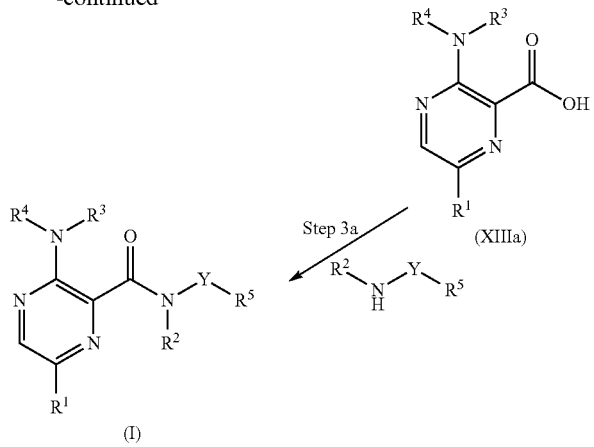

General Procedure 5:
Step 1:
Compounds of formula (XII) are commercially available or can be prepared according to the method described in US 2006/199828 starting from an amino-cyano-acetic acid ester and an appropriate α-ketoaldehyde oxime.

Compounds of formula (XII) wherein R is lower alkyl can also be prepared starting from compounds of formula (XI) which are commercially available or can be prepared starting from methyl 3-amino-pyrazine-2-carboxylate or 3-amino-pyrazine-2-carboxylic acid according to e.g. J. Am. Chem. Soc. 1949, 71, 2798 or WO 2004/092177. Compounds of formula (XI) can be converted to a compound of formula (XII) by a Pd-catalyzed coupling reaction with an organometallic reagent $R^1$-M (e.g. organoboronic acid or organoboronic acid ester) using a Pd-catalyst (e.g. $Pd_2(dba)_3$) and a base (e.g. potassium phosphate) in an organic solvent (e.g. dioxane). Compounds of formula (XII) can be isolated and purified by conventional methods.

Step 1a:
Compounds of formula (XI) wherein R is lower alkyl can also be converted to a compound of formula (XII) by i) protection of the amino group with a suitable protective group (e.g. Boc) using e.g. di-tert-butyl-dicarbonate in the presence of an organic or inorganic base (e.g. DMAP or triethylamine) in an organic solvent, ii) Pd-catalyzed coupling reaction with an organometallic reagent $R^1$-M (e.g. organozinc reagent or organotin reagent) using a Pd-catalyst (e.g. $Pd(PPh_3)_4$) and a base (e.g. potassium carbonate) in an organic solvent (e.g. dioxane), and iii) deprotection of the amino group using e.g. an organic or inorganic acid (e.g. HCl or trifluoroacetic acid) in an organic solvent. Compounds of formula (XII) can be isolated and purified by conventional methods.

Step 2:
A compound of formula (XIII) can be obtained by e.g. a Pd-catalyzed arylation of the amino group of (XII) using aryl halides or heteroaryl halides (e.g. 5-bromopyrimidine) $R^4$—X, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). Compounds of formula (XIII) can be isolated and purified by conventional methods.

Step 2a:
Alternatively, compounds of formula (XII) can be converted to a compound of formula (XIIa) wherein X is a halogene by diazotation using e.g. sodium nitrite or tert-butyl nitrite and subsequent substitution using a suitable copper halide. A compound of formula (XIII) can then be obtained by e.g. a Pd-catalyzed amination of compound (XIIa) using arylamines or heteroarylamines (e.g. 5-aminopyrimidine) $R^4$—NH—$R^3$, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). Compounds of formula (XIII) can be isolated and purified by conventional methods.

Step 3:
Compounds of formula (XIII) can be converted to a compound of formula (I) by direct aminolysis of the ester group using heteroarylamines $R^5$—Y—NH—$R^2$ and a Lewis acid (e.g. trimethylaluminium or dimethylaluminium chloride) in an organic solvent (e.g. toluene or dioxane). Compounds of formula (I) can be isolated and purified by conventional methods.

Step 3a:
Alternatively, the ester group of a compound of formula (XIII) can be saponified to its free acid (XIIIa) using an inorganic base (e.g. lithium hydroxide, sodium hydroxide) in an organic solvent (e.g. ethanol, dioxane, THF). Compounds of formula (XIIIa) can then be converted to a compound of formula (I) by amide bond formation using heteroarylamines $R^5$—Y—NH—$R^2$, a coupling reagent (e.g. propylphosphonic acid anhydride, HATU, TBTU) and an organic base (e.g. N,N-diisopropylethylamine, N-methyl-morpholine or triethylamine) in an organic solvent (e.g. DMF, ethyl acetate, THF). Compounds of formula (I) can be isolated and purified by conventional methods.

Certain substituents on the groups $R^1$, $R^2$, $R^3$, $R^4$ and $R^5$ may not be inert to the conditions of the synthesis sequences described above and may require protection by standard protecting groups known in the art. For instance, an amino or hydroxyl group may be protected as an acetyl or tert.-butoxycarbonyl derivative. Alternatively, some substituents may be derived from others at the end of the reaction sequence. For instance, a compound of formula I may be synthesized bearing a nitro-, an ethoxycarbonyl, an ether, a sulfonic acid substituent on the groups $R^1$, $R^2$, $R^3$, $R^4$ and $R^5$, which substituents are finally converted to an amino- (e.g. by reduction of a nitro group or cleavage of a suitable amino protective group (e.g. removal of a Boc group with TFA)), alkylamino- (e.g. by reductive amination of an amino group), dialkylamino- (e.g. by alkylation of an amino group, reduction of an appropriate acylamino group with lithium aluminum hydride or Eschweiler-Clarke reaction with an appropriate amino or alkylamino group), acylamino- (by amide formation from an amino group e.g. with appropriate acyl halides or with appropriate carboxylic acids after their activation with CDI, EDC etc.), alkylsulfonylamino (e.g. by reaction of an amino group with sulfonyl chlorides), arylsulfonylamino substituent (e.g. by reaction of an amino group with sulfonyl chlorides), hydroxyl- (by cleavage of a suitable hydroxy protective group (e.g. hydrogenolytic removal of a benzyl ether or oxidative cleavage of a p-methoxy benzyl ether), ether- (e.g. by Williamson's ether synthesis from a hydroxyl group) or to a carboxamide substituent (e.g. by amide formation from a carboxylic acid group with appropriate amines after activation of the carboxylic acid group with CDI, EDC etc. or conversion to an acyl chloride), or to a sulfonamide substituent by standard procedures.

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxane or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another preferred embodiment, the invention relates to a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also relates to the use of compounds as described above for the preparation of medicaments for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

The invention also relates to compounds or pharmaceutically acceptable salts thereof as defined above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Prevention and/or treatment of schizophrenia is a preferred indication. Furthermore, prevention and/or treatment of positive, negative and/or cognitive symptoms associated with schizophrenia is preferred.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 μl contained 20 mM HEPES pH=7.5/10 mM MgCl$_2$/0.05 mg/ml BSA (Sigma cat. # A-7906), 50 nM cGMP (Sigma, cat. # G6129) and 50 nM [$^3$H]-cGMP (GE Healthcare, cat. # TRK392 S.A. 13.2Ci/mmol), 3.75 ng/well PDE10A enzyme (Enzo Life Science, Lausen, Switzerland cat # SE-534) with or without a specific test compound. A range of concentrations of the potential inhibitor was used to generate data for calculating the concentration of inhibitor resulting in 50% of the effect (e.g. IC$_{50}$, the concentration of the competitor inhibiting PDE10A activity by 50%). Non-specific activity was tested without the enzyme. The reaction was initiated by the addition of the substrate solution (cGMP and [$^3$H]-cGMP) and allowed to progress for 20 minutes at room temperature. The reaction was terminated by adding 25 μA of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) preferably have an IC$_{50}$ value below 10 μM, preferably below 5 μM, more preferably below 1 μM. Preferably, the IC$_{50}$ values are above 0.01 nM. The following table shows data for some examples.

| Example | PDE10A inhibition IC$_{50}$ [μmol/l] |
|---|---|
| 1 | 0.09 |
| 4 | 0.368 |
| 5 | 0.048 |
| 6 | 0.023 |
| 7 | 0.01 |
| 8 | 0.005 |
| 9 | 0.122 |
| 10 | 0.002 |
| 11 | 0.005 |
| 12 | 0.001 |
| 13 | 0.256 |
| 14 | 0.001 |
| 15 | 0.004 |
| 16 | 0.002 |
| 17 | 0.005 |
| 18 | 0.013 |
| 19 | 0.002 |
| 20 | 0.001 |
| 21 | 0.004 |
| 22 | 0.002 |
| 23 | 0.002 |
| 24 | 0.001 |
| 25 | <0.001 |
| 26 | 0.002 |
| 27 | 0.003 |
| 28 | 0.001 |
| 29 | 0.002 |
| 30 | 0.005 |
| 31 | 0.001 |
| 32 | 0.001 |
| 33 | 0.170 |
| 34 | 0.001 |
| 35 | 0.021 |
| 36 | 0.004 |
| 37 | 0.002 |
| 38 | <0.001 |
| 39 | 0.003 |
| 40 | <0.001 |
| 41 | 0.003 |
| 42 | 0.024 |
| 43 | 0.004 |
| 44 | 1.879 |
| 45 | 6.378 |
| 46 | 0.612 |
| 47 | 1.446 |
| 48 | 0.435 |
| 49 | 0.744 |
| 50 | 0.001 |
| 51 | 0.004 |
| 52 | 0.033 |
| 53 | 0.020 |
| 54 | 0.087 |
| 55 | 0.004 |
| 56 | 1.451 |
| 57 | 0.781 |
| 58 | 2.451 |
| 59 | 0.007 |
| 60 | 0.006 |
| 61 | 0.028 |
| 62 | 0.002 |
| 63 | 0.327 |
| 64 | 2.042 |

-continued

| Example | PDE10A inhibition IC$_{50}$ [μmol/l] |
|---|---|
| 65 | 0.055 |
| 66 | 0.187 |

The invention provides pharmaceutical compositions containing compounds of formula (I) and/or their pharmaceutically acceptable salts and a pharmaceutically acceptable carrier and/or adjuvant. Such compositions can be, e.g. in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical compositions can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical compositions are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula (I) can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 0.1-500 mg, preferably 1-200 mg, of a compound of formula (I).

The following examples serve to illustrate the present invention in more detail. They are, however, not intended to limit its scope in any manner.

EXAMPLES

A. Intermediates

A-1: 6-Methyl-3-(pyrimidin-5-ylamino)-pyridine-2-carboxylic acid ethyl ester

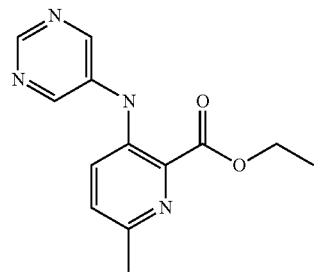 [SMILES: CCOC(=O)c1nc(C)ccc1Nc1cncnc1]

This compound was prepared according to the method described in US 2006/199960.

MS: M=259.3 (M+H)$^+$

A-2: 6-Cyclopropyl-3-(pyrimidin-5-ylamino)-pyridine-2-carboxylic acid ethyl ester

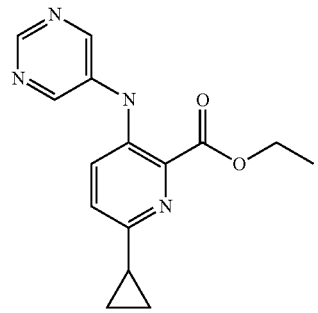 [SMILES: CCOC(=O)c1nc(C2CC2)ccc1Nc1cncnc1]

Step 1:
3-Amino-6-cyclopropyl-pyridine-2-carboxylic acid ethyl ester

To a solution of 3-amino-6-bromo-pyridine-2-carboxylic acid ethyl ester (prepared according to US 2006/199960; 1.0 g, 4.08 mmol), potassium phosphate (3.03 g, 14.3 mmol), tricyclohexylphosphine (0.228 g, 0.82 mmol) and water (1.25 ml) in toluene (25 ml) was added cyclopropylboronic acid (0.91 g, 10.6 mmol) and palladium (II) acetate (90 mg, 0.4 mmol). The resulting suspension was stirred at 100° C. for 24 hours. After solvent evaporation, the title compound was obtained after silica gel chromatography using a heptane/ethyl acetate gradient as yellow solid (0.374 g, 44%).

MS: M=207.0 (M+H)$^+$

Step 2: 6-Cyclopropyl-3-(pyrimidin-5-ylamino)-pyridine-2-carboxylic acid ethyl ester A suspension of 3-amino-6-cyclopropylpyridine-2-carboxylic acid ethyl ester (763 mg, 3.7 mmol), 5-bromopyrimidine (823 mg, 5.2 mmol), water (140 µl, 7.8 mmol) and potassium carbonate (920 mg, 6.7 mmol) in o-xylene (10 ml) was evacuated and vented with argon. Palladium(II) acetate (33 mg, 0.15 mmol) and 4,5-bis(diphenylphosphino)-9,9-dimethylxanthene (Xantphos; 107 mg, 0.18 µmol) were consecutively added under inert gas atmosphere and the reaction mixture was heated to 140° C. and stirred overnight. After cooling-down to ambient temperature, the reaction mixture was diluted with methylenechloride (15 ml) and filtrated. The filtrate was concentrated in vacuo and the product was purified by silica gel chromatography using a heptane/ethyl acetate gradient to yield the title compound (796 mg, 75.7%) as light yellow solid.
MS: M=285.3 (M+H)+

A-3: 6-Methoxymethyl-3-(pyrimidin-5-ylamino)-pyridine-2-carboxylic acid methyl ester

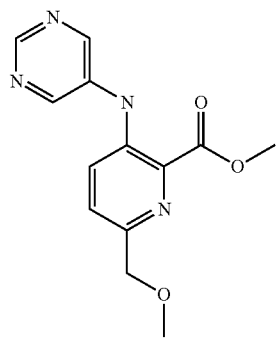

Step 1: 5-Bromo-pyridin-2-yl-methanol

To a solution of 5-bromopyridin-2-carboxylic acid (8 g, 42.1 mmol) in THF (100 ml) was added borane-dimethylsulphide (16 ml, 168.30 mmol) dropwise at 0° C. After warming-up to ambient temperature stirring was continued for 24 hours. The solution was cooled again to 0° C., quenched with MeOH and refluxed for 1 h. Solvents were removed and the residue was treated with water. The aqueous phase was extracted with ethyl acetate and the combined organic layers were washed with water and brine, dried, filtered and concentrated under reduced pressure to afford 4.76 g (64%) of the title compound.
MS: M=188.0 & 190.0 (M+H)+

Step 2: 5-Bromo-2-hydroxymethyl-pyridine-1-oxide

5-Bromo-pyridin-2-yl-methanol (6.0 g, 31.9 mmol) was dissolved in methylenechloride (80 ml) and cooled to 0° C. A solution of 3-chloroperbenzoic acid (8.26 g, 47.9 mmol) in methylenechloride (20 ml) was slowly added, the ice bath was removed after completion of the addition, and the reaction mixture was stirred at ambient temperature for 1 h. The solvent was removed and the crude product was purified by silica gel chromatography using ethyl acetate to yield 3.68 g (56%) of the title compound.
MS: M=204.0 & 206.2 (M+H)+

Step 3: 5-Bromo-2-methoxymethyl-pyridine-1-oxide

To a solution of 5-bromo-2-hydroxymethyl-pyridine-1-oxide (6.43 g, 31.5 mmol) in THF (200 ml) was added sodium hydride (1.51 g, 63.1 mmol) at 0° C., and then the reaction mixture was stirred at ambient temperature for 1 h. After cooling to 0° C., MeI (2.90 ml, 46.6 mmol) was added. The temperature was raised to ambient temperature and the reaction mixture was heated to 70° C. for 1 h. After cooling to 0° C. the reaction mixture was quenched with MeOH. The solvents were removed, and the crude product was purified by silica gel chromatography using an ethyl acetate/hexane eluent to yield 4.8 g (70%) of the title compound.
MS: M=218.2 & 220.2 (M+H)+

Step 4: 3-Bromo-6-methoxymethyl-pyridine-2-carbonitrile

A solution of 5-bromo-2-methoxymethyl-pyridine-1-oxide (5.0 g, 22.7 mmol), triethylamine (12.7 ml, 91 mmol) and trimethylsilyl cyanide (9.1 ml, 68.2 mmol) in acetonitrile (10 ml) was heated to 120° C. for 18 hours in a sealed tube. After completion of the reaction, water was added to the reaction mixture and acetonitrile was removed. The crude material was extracted with ethyl acetate, the combined organic layers were washed with water and brine, dried, filtered, and evaporated. The crude product was purified by silica gel chromatography using an ethyl acetate/hexane eluent to yield 3.0 g (58%) of the title compound.
MS: M=229.2 (M+H)+

Step 5: 3-Bromo-6-methoxymethyl-pyridine-2-carboxylic acid

To a solution of 3-bromo-6-methoxymethyl-pyridine-2-carbonitrile (300 mg, 1.32 mmol) in MeOH (6 ml) was added a solution of potassium hydroxide (1.48 g, 26.43 mmol) in water (4 ml). The mixture was refluxed for 3 hours. MeOH was removed in vacuo, the aqueous solution was neutralized with conc. HCl under cooling, and the mixture was extracted with ethyl acetate. The combined organic layers were washed with water and brine, dried, filtered and evaporated. The obtained product (276 mg, 85%) was used in the next step without any further purification.
MS: M=246.2 & 248.2 (M+H)+

Step 6: 3-Bromo-6-methoxymethyl-pyridine-2-carboxylic acid methyl ester

To a solution of 3-bromo-6-methoxymethyl-pyridine-2-carboxylic acid (200 mg, 0.81 mmol) in benzene (4 ml) and MeOH (1 ml) was slowly added trimethylsilyl-diazomethane (0.41 ml, 0.81 mmol) at ambient temperature, and the reaction mixture was stirred for 2 hours. The solvents were removed and the residue was extracted with ethyl acetate. The combined organic layers were washed with water and brine, dried, filtered, and evaporated. The crude product was purified by silica gel chromatography using an ethyl acetate/hexane eluent to yield 158 mg (75%) of the title compound as light yellow oil.
MS: M=260.0 & 262.0 (M+H)+

Step 7: 6-Methoxymethyl-3-(pyrimidin-5-ylamino)-pyridine-2-carboxylic acid methyl ester According to the method described in step 2 of example A-2, the title compound was obtained as off-white solid in 75% yield.
MS: M=275.2 (M+H)⁺

A-4: 2-Methoxymethyl-5-(pyrimidin-5-ylamino)-pyrimidine-4-carboxylic acid methyl ester

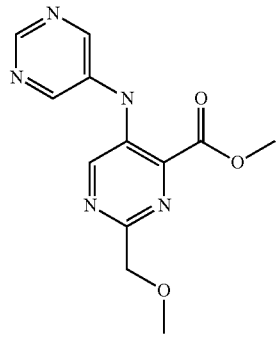

Step 1: 2-Methoxy-acetamidine

To a solution of methoxy-acetonitrile (6 g, 84.4 mmol) in MeOH (60 ml) was added sodium methylate (0.86 g, 16.0 mmol) and the reaction mixture was stirred at ambient temperature for 48 hours. Ammonium chloride (4.52 g, 84.5 mmol) was added to the reaction mixture and stirring was continued for another 12 h. The solvent was removed under reduced pressure yielding the title compound which was used in the next step without any further purification. Yield: 6.5 g (88%)
MS: M=89.1 (M+H)⁺

Step 2: 5-Bromo-2-methoxymethyl-pyrimidine-4-carboxylic acid

To a solution of 2-methoxy-acetamidine (7.21 g, 89.19 mmol) in EtOH (50 ml) was added sodium ethylate (26 ml, 22% solution in EtOH) and the reaction mixture was heated to 50° C. for 30 min. A solution of mucobromic acid (6.5 g, 38.77 mmol) in EtOH (50 ml) was added followed by sodium ethylate (14 ml, 22% solution in EtOH), and the reaction mixture was continued to stir at 50° C. for 1 h. After filtration and solvent evaporation, water (5 ml) was added, the reaction mixture was cooled to 0° C. and acidified with 2N HCl solution to pH ~6. After evaporation of water, the residue was dissolved in MeOH, filtered, and the filtrate was evaporated. The crude material was purified by silica gel chromatography using a methanol/methylenechloride eluent as solvent to yield 3.73 g (60%) of the title compound.
MS: M=246.9 & 248.9 (M+H)⁺

Step 3: 5-Bromo-2-methoxymethyl-pyrimidine-4-carboxylic acid methyl ester

To a solution of 5-bromo-2-methoxymethyl-pyrimidine-4-carboxylic acid (2.5 g, 10.1 mmol) in acetone (100 ml) was added Cs₂CO₃ (19.8 g, 60.7 mmol) followed by methyliodide (3.8 ml, 60.7 mmol). The mixture was heated to reflux for 8 h. The reaction mixture was then filtered, and the filtrate was evaporated. The crude material was purified by silica gel chromatography using a ethyl acetate/hexane eluent to yield 700 mg (27%) of the title compound as yellow oil.
MS: M=260.9 & 262.7 (M+H)⁺

Step 4: 2-Methoxymethyl-5-(pyrimidin-5-ylamino)-pyrimidine-4-carboxylic acid methyl ester According to the method described in step 2 of example A-2, the title compound was obtained as yellow solid in 17% yield.
MS: M=276.2 (M+H)⁺

A-5: 6-Cyclopropyl-3-(pyrimidin-5-ylamino)-pyridine-2-carboxylic acid

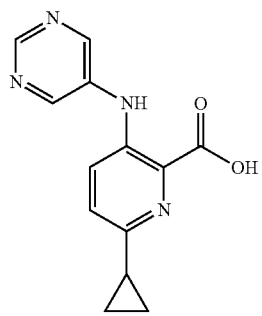 [SMILES: O=C(O)c1nc(C2CC2)ccc1Nc1cncnc1]

A suspension of 6-cyclopropyl-3-(pyrimidin-5-ylamino)-pyridine-2-carboxylic acid ethyl ester (1.85 g, 6.5 mmol) from example A-2 in EtOH (15 ml) was treated with 1N NaOH (13 ml). The reaction mixture was stirred at r.t. overnight. The compact suspension was brought to pH 6 by addition of 1N HCl. The solid was collected by filtration, washed with EtOH and dried to give the product (1.29 g, 77%) as off-white solid.
MS: M=255.0 (M−H)

A-6: 6-Ethyl-3-(pyrimidin-5-ylamino)-pyridine-2-carboxylic acid ethyl ester

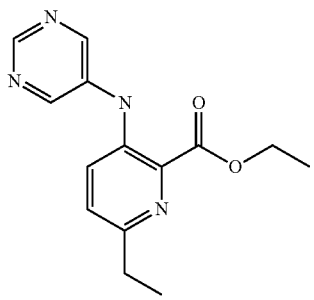 [SMILES: CCOC(=O)c1nc(CC)ccc1Nc1cncnc1]

This compound was prepared according to the method described in US 2006/199960
MS: M=273.3 (M+H)⁺

A-7: 6-Cyclopropyl-3-(pyrimidin-5-ylamino)-pyrazine-2-carboxylic acid methyl ester

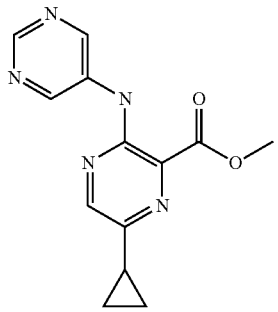 [SMILES: COC(=O)c1nc(C2CC2)cnc1Nc1cncnc1]

Step 1: 3-amino-6-cyclopropylpyrazine-2-carboxylic acid methyl ester

To a suspension of 3-amino-6-bromopyrazine-2-carboxylic acid methyl ester (17.8 g, 76.7 mmol), cyclopropylboronic acid (8.57 g, 99.7 mmol), potassium phosphate (57.0 g, 268 mmol) and tricyclohexylphosphine (2.15 g, 7.67 mmol) in toluene (445 ml) and water (22 ml) was added palladium(II) acetate (0.86 g, 3.84 mmol). The reaction mixture was heated to 100° C. and stirred for 20 h. Water (200 ml) was added, the organic layer was washed with water and brine and the aqueous layer was back-extracted with ethyl acetate. The combined organic phases were dried and the solvent was evaporated. The product was obtained after silica gel chromatography using a heptane/ethyl acetate gradient as yellow solid (1.69 g, 11.4%).

MS: M=194.1 (M+H)$^+$

Step 2: 6-Cyclopropyl-3-(pyrimidin-5-ylamino)-pyrazine-2-carboxylic acid methyl ester A suspension of 3-amino-6-cyclopropylpyrazine-2-carboxylic acid methyl ester (2.17 g, 11.2 mmol), 5-bromopyrimidine (2.5 g, 15.7 mmol), water (425 µl, 23.6 mmol) and potassium carbonate (2.79 g, 20.2 mmol) in o-xylene (43.4 ml) was vented with argon and treated with ultrasound for 2 min. Palladium(II) acetate (101 mg, 0.45 mmol) and 4,5-bis(diphenylphosphino)-9,9-dimethylxanthene (Xantphos; 325 mg, 0.56 µmol) were consecutively added under inert gas atmosphere and the reaction mixture was heated to 140° C. and stirred for 2 h. After cooling-down to ambient temperature, the reaction mixture was poured into water (100 ml) and extracted with ethyl acetate. The organic layers were dried and concentrated in vacuo. The product was obtained after silica gel chromatography using a heptane/ethyl acetate gradient as yellow solid (2.49 g, 81.7%).

MS: M=272.2 (M+H)$^+$

A-8: 6-Methyl-3-(pyrimidin-5-ylamino)-pyrazine-2-carboxylic acid

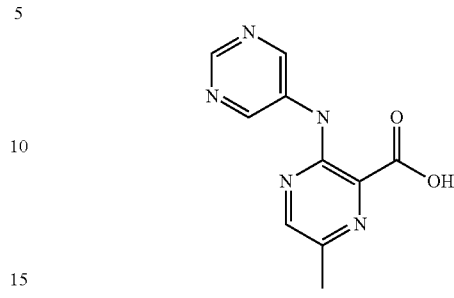

Step 1: 3-Amino-6-methyl-pyrazine-2-carboxylic acid ethyl ester

This compound was prepared according to the method described in US 2006/199828.

MS: M=182.1 (M+H)$^+$

Step 2: 6-Methyl-3-(pyrimidin-5-ylamino)-pyrazine-2-carboxylic acid ethyl ester A suspension of 3-amino-6-methyl-pyrazine-2-carboxylic acid ethyl ester (500 mg, 2.8 mmol), 5-bromopyrimidine (614 mg, 3.9 mmol), water (104 µl, 5.8 mmol) and potassium carbonate (686 mg, 5.0 mmol) in xylene (7 ml) was vented with argon. Palladium(II) acetate (25 mg, 0.11 mmol) and 4,5-bis(diphenylphosphino)-9,9-dimethylxanthene (Xantphos; 80 mg, 0.14 mmol) were consecutively added under inert gas atmosphere and the reaction mixture was heated to 140° C. and stirred for 5 h. After cooling-down to ambient temperature, the reaction mixture was diluted with water (5 ml) and extracted with methylenechloride. The organic layers were washed with water and brine, dried and concentrated in vacuo. The product was obtained after silica gel chromatography using a heptane/ethyl acetate gradient as light yellow solid (585 mg, 81.8%). MS: M=260.1 (M+H)$^+$

Step 3: 6-Methyl-3-(pyrimidin-5-ylamino)-pyrazine-2-carboxylic acid

6-Methyl-3-(pyrimidin-5-ylamino)-pyrazine-2-carboxylic acid ethyl ester (300 mg, 1.15 mmol) was dissolved in a THF/ethanol (5 ml/1 ml) mixture, cooled to 0° C. and treated with lithium hydroxide (4.7 ml, 1N aqueous solution). The reaction mixture was allowed to warms to ambient temperature and stirred at that temperature for 1 hour. The pH value was subsequently adjusted to acidic and the resulting suspension was filtrated. The precipitate was washed with water and ethyl acetate and dried to yield the product as light yellow solid (185 mg, 69%).

MS: M=230.2 (M+H)$^+$

A-9: 2-Isopropyl-5-(pyrimidin-5-ylamino)-pyrimidine-4-carboxylic acid methyl ester

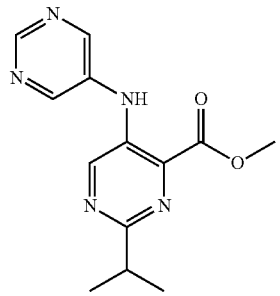 [SMILES: COC(=O)c1nc(C(C)C)ncc1Nc1cncnc1]

Step 1: 5-Bromo-2-isopropyl-pyrimidine-4-carboxylic acid

To a stirred suspension of isobutyramidine hydrochloride (6.47 g, 47.5 mmol) at r.t. in EtOH (30 ml) under an argon atmosphere was added sodium ethylate solution (21 ml, 21% in EtOH) over 5 min. The suspension was heated to 50° C. and a solution of mucobromic acid (5.7 g, 22.1 mmol) in EtOH (24 ml) was added dropwise over 5 min at 50° C. An additional portion of sodium ethylate solution (12 ml, 21% in EtOH) was added dropwise over 5 min. The mixture was then cooled to r.t. The solids were filtered off, and the cake was washed with plenty of ethanol. The filtrate was concentrated to leave the crude product as a light brown solid. The crude material was triturated in 2 N HCl (100 ml). The product was collected by filtration, washed with plenty of $H_2O$ and plenty of n-heptane and dried to give the product (2.09 g, 73%) as beige solid. MS: M=244.9 (M–H)$^+$

Step 2: 5-Bromo-2-isopropyl-pyrimidine-4-carboxylic acid methyl ester

To a stirred, cooled (0° C.) solution of 5-bromo-2-isopropyl-pyrimidine-4-carboxylic acid (3 g, 12.2 mmol) in methanol (50 ml) under an argon atmosphere was added dropwise thionyl chloride (4.37 g, 2.68 ml, 36.7 mmol). When the addition was complete, the mixture was allowed to warm to r.t. and stirring at r.t. was continued for 17 h. The orange mixture was concentrated to leave a paste which was taken up in EtOAc (50 ml)/saturated aqueous $Na_2CO_3$ solution (50 ml). The aqueous phase was extracted with EtOAc. The combined organics were washed with $H_2O$ and brine, dried over $MgSO_4$, filtered and concentrated to leave the product (2.98 g, 94%) as a light brown oil which was used in the next reaction step without further purification.

MS: M=260.9 (M+H)$^+$

Step 3: 2-Isopropyl-5-(pyrimidin-5-ylamino)-pyrimidine-4-carboxylic acid methyl ester According to the method described in step 2 of example A-2, the title compound was obtained as yellow solid in 76% yield.

MS: M=272.1 (M–H)$^-$

A-10: 2-Cyclopropyl-5-(pyrimidin-5-ylamino)-pyrimidine-4-carboxylic acid methyl ester

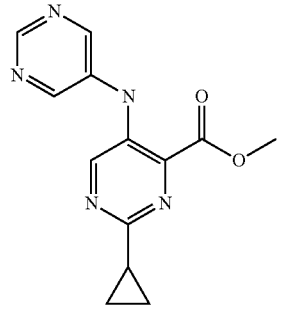 [SMILES: COC(=O)c1nc(C2CC2)ncc1Nc1cncnc1]

According to the methods described in example A-9, the title compound was obtained as yellow solid starting from cyclopropanecarboxamidine hydrochloride.

MS: M=270.1 (M–H)$^-$

A-11: 2-tert-Butyl-5-(pyrimidin-5-ylamino)-pyrimidine-4-carboxylic acid methyl ester

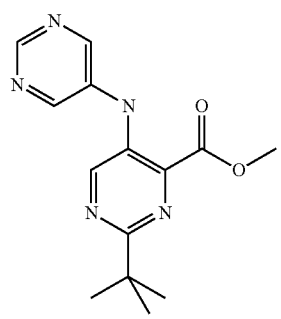 [SMILES: COC(=O)c1nc(C(C)(C)C)ncc1Nc1cncnc1]

According to the methods described in example A-9, the title compound was obtained as waxy solid starting from 2,2-dimethyl-propionamidine hydrochloride.

MS: M=288.1 (M+H)$^+$

A-12: 2-Cyclohexyl-5-(pyrimidin-5-ylamino)-pyrimidine-4-carboxylic acid methyl ester

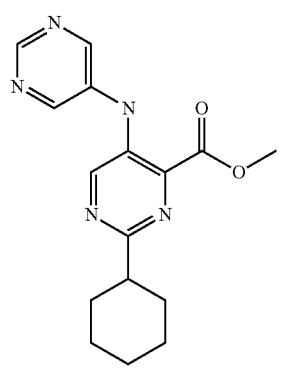 [SMILES: COC(=O)c1nc(C2CCCCC2)ncc1Nc1cncnc1]

According to the methods described in example A-9, the title compound was obtained as waxy solid starting from cyclohexanecarboxamidine.
MS: M=314.1 (M+H)⁺

A-13: 2-Isobutyl-5-(pyrimidin-5-ylamino)-pyrimidine-4-carboxylic acid methyl ester

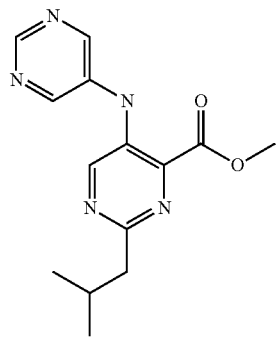 [SMILES: COC(=O)c1nc(CC(C)C)ncc1Nc1cncnc1]

According to the methods described in example A-9, the title compound was obtained as viscous oil starting from 3-methyl-butyramidine hydrochloride.
MS: M=288.1 (M+H)⁺

A-14: 6-Ethyl-3-(pyrimidin-5-ylamino)-pyridine-2-carboxylic acid

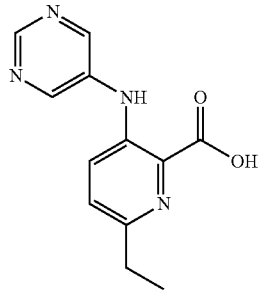 [SMILES: CCc1ccc(Nc2cncnc2)c(C(=O)O)n1]

6-Ethyl-3-(pyrimidin-5-ylamino)-pyridine-2-carboxylic acid ethyl ester (prepared according to US 2006/199960; 200 mg, 0.73 mmol) was dissolved in a THF/ethanol (12 ml/3 ml) mixture, cooled to 0° C. and treated with lithium hydroxide (2.2 ml, 1N aqueous solution). The reaction mixture was allowed to warm-up to ambient temperature and stirring was continued at that temperature for 2 hours. The pH value was subsequently adjusted to acidic and the reaction mixture was extracted with dichloromethane (3×40 ml). The combined organic phases were dried and evaporated to yield the product as light yellow solid (175 mg, 97%).
MS: M=243.1 (M+H)⁺

A-15: 3-Amino-6-cyano-pyridine-2-carboxylic acid ethyl ester

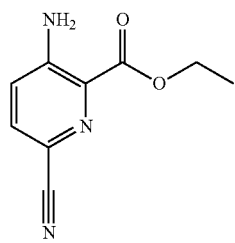

A solution of 3-amino-6-bromo-pyridine-2-carboxylic acid ethyl ester (40 mg, 163 μmol) and copper(I) cyanide (29.2 mg, 326 μmol) in DMF (800 μL) was heated in the microwave at 220° C. for 8 min. The reaction mixture was filtered through diatomaceous filter-aid and the crude product was purified by preparative HPLC to afford the title compound as off-white solid (8.3 mg, 26.6%).
MS: M=192.2 (M+H)⁺

A-16: 5-Bromo-2-(2-methoxy-ethylamino)-pyrimidine-4-carboxylic acid ethyl ester

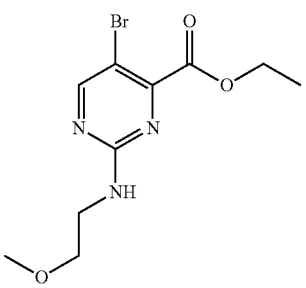 [SMILES: CCOC(=O)c1nc(NCCOC)ncc1Br]

Step 1:
5-Bromo-2-methanesulfonyl-pyrimidine-4-carboxylic acid ethyl ester

A solution of 3-chloroperbenzoic acid (1.78 g, 7.2 mmol) in dichloromethane (50 ml) was slowly added to a solution of 5-bromo-2-methylsulfanyl-pyrimidine-4-carboxylic acid ethyl ester (1.0 g, 3.6 mmol) in dichloromethane (50 ml) at 0-5° C. After 30 min. the cooling bath was removed and the reaction mixture was stirred at room temperature overnight. The reaction mixture was extracted with saturated sodium bicarbonate solution and water. The aqueous phases were back-extracted with dichloromethane and the combined organic phases were dried over MgSO₄, filtered and evaporated. The crude product was purified by silica gel chromatography using an ethyl acetate/heptane eluent to yield the title compound as colorless waxy solid (0.83 g, 74%). MS: M=311.1 (M+H)⁺

Step 2: 5-Bromo-2-(2-methoxy-ethylamino)-pyrimidine-4-carboxylic acid ethyl ester 2-Methoxyethylamine (0.278 ml, 3.2 mmol) was added at room temperature to a solution of 5-bromo-2-methanesulfonyl-pyrimidine-4-carboxylic acid ethyl ester (0.2 g, 0.65 mmol) in dichloromethane (5 ml). Stirring was continued at 45° C. for 2 hours. The solvent was evaporated and the crude product was purified by silica gel chromatography using an ethyl acetate/heptane eluent to yield the title compound as colorless oil (0.175 g, 89%).
MS: M=304.2 (M+H)⁺

B. Final Products

Example 1

6-Methyl-3-(pyrimidin-5-ylamino)-pyridine-2-carboxylic acid (1-phenyl-1H-pyrazol-3-yl)-amide

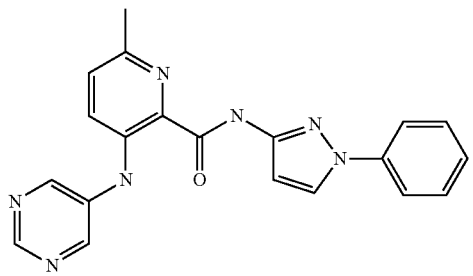 [SMILES: Cc1ccc(Nc2cncnc2)c(C(=O)Nc2ccn(-c3ccccc3)n2)n1]

Phenyl-1H-pyrazol-3-ylamine (277 mg, 1.74 mmol) was dissolved under inert gas atmosphere in dioxane (8 ml) and trimethylaluminium (1.02 ml, 2M heptane solution) was added. After stirring for 30 min at ambient temperature, 6-methyl-3-(pyrimidin-5-ylamino)-pyridine-2-carboxylic acid ethyl ester (A-1; 150 mg, 0.58 mmol) was added and the reaction mixture was heated at reflux for 1.5 hours. Upon cooling to room temperature water (0.7 ml) was added and intensive stirring was continued for 5 min. Sufficient sodium sulfate for water absorption and dichloromethane were added while stirring was continued. The resulting solution was then filtered through decalite and washed with dichloromethane. The solvent was evaporated and the final product was obtained after silica gel chromatography using a heptane/ethyl acetate gradient as light yellow crystalline material (176 mg, 81%).

MS: M=372.2 (M+H)$^+$

Example 2

6-Methyl-3-(pyrimidin-5-ylamino)-pyridine-2-carboxylic acid [1-(4-fluoro-phenyl)-1H-pyrazol-3-yl]-amide

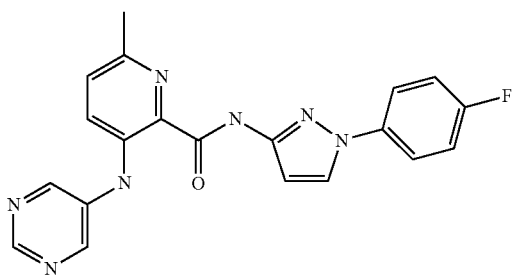 [SMILES: Cc1ccc(Nc2cncnc2)c(C(=O)Nc2ccn(-c3ccc(F)cc3)n2)n1]

Step 1: 1-(4-Fluoro-phenyl)-1H-pyrazol-3-ylamine

To a hot solution of potassium tert-butoxide (2.54 g, 23 mmol) in tert-butanol (30 ml) was added 4-fluorophenylhydrazine hydrochloride (1.67 g, 10 mmol). After cooling to ambient temperature, a solution of 3-ethoxyacrylonitrile (1.0 g, 10 mmol) in tert-butanol (5 ml) was added and the mixture was refluxed for 3 h. After cooling to ambient temperature, the solvent was evaporated. The residue was dissolved in ethyl acetate and extracted with water. The organic phases were combined, dried and evaporated. Silica gel chromatography using a heptane/ethyl acetate gradient yielded the amine as orange solid (0.78 g, 42%).

MS: M=178.3 (M+H)$^+$

Step 2: 6-Methyl-3-(pyrimidin-5-ylamino)-pyridine-2-carboxylic acid [1-(4-fluoro-phenyl)-1H-pyrazol-3-yl]-amide 1-(4-Fluoro-phenyl)-1H-pyrazol-3-ylamine (55 mg, 0.31 mmol) was dissolved under inert gas atmosphere in dioxane (2 ml) and trimethylaluminium (0.154 ml, 2M toluene solution) was added. After stirring for 30 min at ambient temperature, 6-methyl-3-(pyrimidin-5-ylamino)-pyridine-2-carboxylic acid ethyl ester (A-1; 20 mg, 0.08 mmol) was added and the reaction mixture was heated at reflux for 18 hours. Upon cooling to room temperature water (0.5 ml) was added and intensive stirring was continued for 5 min. Sufficient sodium sulfate for water absorption and dichloromethane were added while stirring is continued. The resulting solution was then filtered through decalite and washed with dichloromethane. The solvent was evaporated and the final product was obtained after silica gel chromatography using a heptane/ethyl acetate gradient as off-white solid (5 mg, 16%).

MS: M=390.2 (M+H)$^+$

Example 3

6-Methyl-3-(pyrimidin-5-ylamino)-pyridine-2-carboxylic acid [1-(2-fluoro-phenyl)-1H-pyrazol-3-yl]-amide

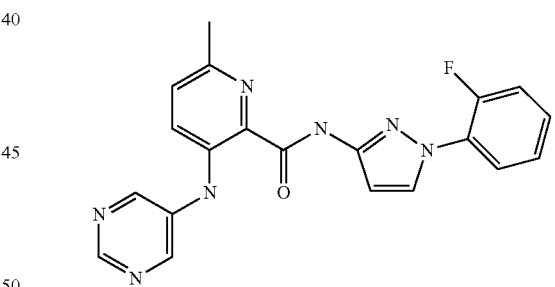

Step 1: 1-(2-Fluoro-phenyl)-1H-pyrazol-3-ylamine

According to the method described in step 1 of example 2, the amine was obtained starting from 2-fluorophenylhydrazine×HCl as brown solid in 24% yield.

MS: M=178.3 (M+H)$^+$

Step 2: 6-Methyl-3-(pyrimidin-5-ylamino)-pyridine-2-carboxylic acid [1-(2-fluoro-phenyl)-1H-pyrazol-3-yl]-amide According to the method described in step 2 of example 2, the title compound was obtained starting from A-1 and 1-(2- fluoro-phenyl)-1H-pyrazol-3-ylamine as off-white solid in 16% yield. MS: M=390.2 (M+H)+

Example 4

6-Methyl-3-(pyrimidin-5-ylamino)-pyridine-2-carboxylic acid (1-pyridin-2-yl-1H-pyrazol-3-yl)-amide

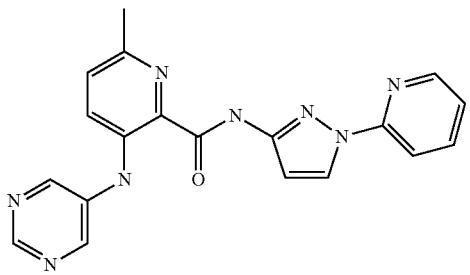 [SMILES: Cc1ccc(Nc2cncnc2)c(C(=O)Nc2ccn(-c3ccccn3)n2)n1]

Step 1: 1-Pyridin-2-yl-1H-pyrazol-3-ylamine

According to the method described in step 1 of example 2, the amine was obtained starting from pyridine-2-ylhydrazine as yellow solid in 34% yield.
MS: M=161.5 (M+H)+

Step 2: 6-Methyl-3-(pyrimidin-5-ylamino)-pyridine-2-carboxylic acid (1-pyridin-2-yl-1H-pyrazol-3-yl)-amide According to the method described in step 2 of example 2, the title compound was obtained starting from A-1 and 1-pyridin-2-yl-1H-pyrazol-3-ylamine as off-white solid in 48% yield. MS: M=373.1 (M+H)+

Example 5

6-Methyl-3-(pyrimidin-5-ylamino)-pyridine-2-carboxylic acid (1-pyridin-4-yl-1H-pyrazol-3-yl)-amide

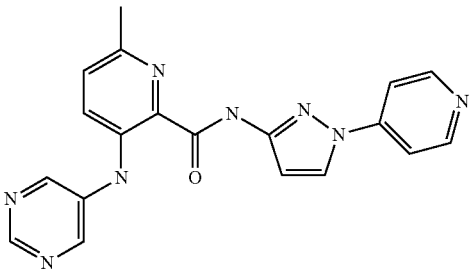 [SMILES: Cc1ccc(Nc2cncnc2)c(C(=O)Nc2ccn(-c3ccncc3)n2)n1]

Step 1: 1-Pyridin-4-yl-1H-pyrazol-3-ylamine

To a solution of potassium carbonate (4.46 g, 32 mmol) in water (20 ml) was added pyridine-4-yl-hydrazine×2HCl (1.47 g, 8 mmol) and the mixture was cooled to 10° C. 2,3-Dichloropropionitrile (1.0 g, 8 mmol) was added dropwise at that temperature. Subsequently, the mixture was stirred at 45° C. for 3 h and at ambient temperature overnight. The reaction mixture was extracted with dichloromethane, the organic phases were combined, washed with brine, dried and the solvent was evaporated. Silica gel chromatography using a heptane/ethyl acetate gradient yielded the amine as yellow solid (80 mg, 6%).
MS: M=161.3 (M+H)+

Step 2: 6-Methyl-3-(pyrimidin-5-ylamino)-pyridine-2-carboxylic acid (1-pyridin-4-yl-1H pyrazol-3-yl)-amide According to the method described in step 2 of example 2, the title compound was obtained starting from A-1 and 1-pyridin-4-yl-1H-pyrazol-3-ylamine as off-white solid in 25% yield. MS: M=373.2 (M+H)+

Example 6

6-Cyclopropyl-3-(pyrimidin-5-ylamino)-pyridine-2-carboxylic acid [1-(4-fluoro-phenyl)-1H-pyrazol-3-yl]-amide

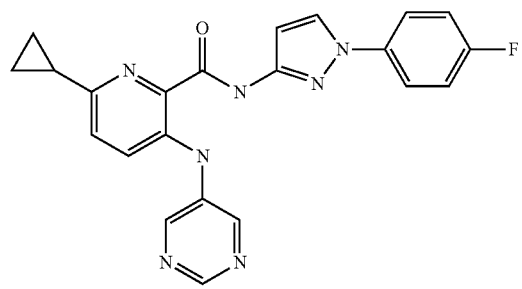 [SMILES: O=C(Nc1ccn(-c2ccc(F)cc2)n1)c1nc(C2CC2)ccc1Nc1cncnc1]

According to the method described in step 2 of example 2, the title compound was obtained starting from A-2 and 1-(4-fluoro-phenyl)-1H-pyrazol-3-ylamine as light yellow solid in 86% yield. MS: M=416.2 (M+H)+

Example 7

6-Cyclopropyl-3-(pyrimidin-5-ylamino)-pyridine-2-carboxylic acid (1-pyridin-4-yl-1H-pyrazol-3-yl)-amide

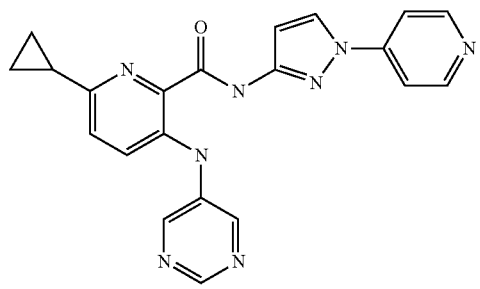 [SMILES: O=C(Nc1ccn(-c2ccncc2)n1)c1nc(C2CC2)ccc1Nc1cncnc1]

According to the method described in step 2 of example 2, the title compound was obtained starting from intermediate A-2 and 1-pyridin-4-yl-1H-pyrazol-3-ylamine as yellow solid in 62% yield. MS: M=399.2 (M+H)+

Example 8

6-Cyclopropyl-3-(pyrimidin-5-ylamino)-pyridine-2-carboxylic acid (2-methyl-5-pyridin-2-yl-2H-pyrazol-3-yl)-amide

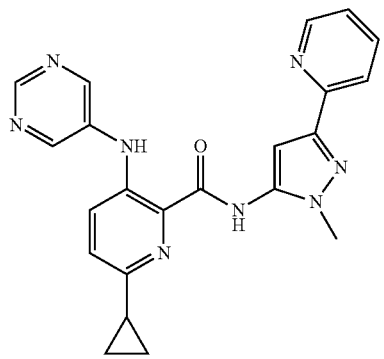 [SMILES: Cn1nc(-c2ccccn2)cc1NC(=O)c1nc(C2CC2)ccc1Nc1cncnc1]

According to the method described in example 1, the title compound was obtained starting from intermediate A-2 and 1-methyl-3-pyridin-2-yl-1H-pyrazol-5-amine as light yellow solid in 63% yield. MS: M=413.2 (M+H)$^+$

Example 9

6-Cyclopropyl-3-(pyrimidin-5-ylamino)-pyridine-2-carboxylic acid [2-(2-hydroxy-ethyl)-5-phenyl-2H-pyrazol-3-yl]-amide

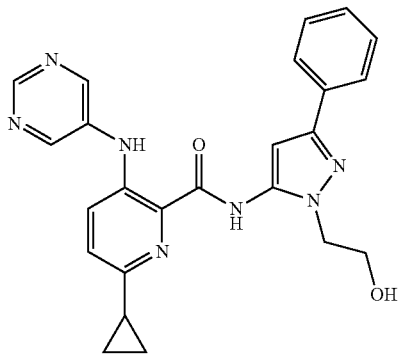 [SMILES: O=C(Nc1cc(-c2ccccc2)nn1CCO)c1nc(C2CC2)ccc1Nc1cncnc1]

According to the method described in example 1, the title compound was obtained starting from intermediate A-2 and 2-(5-amino-3-phenyl-pyrazol-1-yl)-ethanol (CAS 14085-42-8) as light yellow solid in 12% yield. MS: M=442.2 (M+H)$^+$

Example 10

6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide

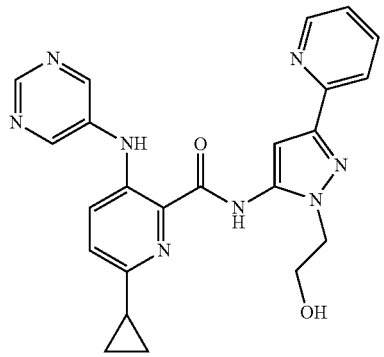 [SMILES: O=C(Nc1cc(-c2ccccn2)nn1CCO)c1nc(C2CC2)ccc1Nc1cncnc1]

Step 1: 2-(5-Amino-3-pyridin-2-yl-pyrazol-1-yl)-ethanol

A solution of 3-oxo-3-pyridin-2-yl-propionitrile (0.5 g, 3.4 mmol; CAS 54123-21-6) in EtOH (20 ml) was treated with 2-hydroxyethylhydrazine (0.7 ml, 10.3 mmol). The reaction mixture was refluxed overnight, then concentrated. After silica gel chromatography using a CH$_2$Cl$_2$/MeOH gradient, the product was obtained as viscous yellow oil (0.56 g, 80%). MS: M=205.1 (M+H)$^+$ Step 2: 6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide According to the method described in example 1, the title compound was obtained starting from intermediate A-2 and 2-(5-amino-3-pyridin-2-yl-pyrazol-1-yl)-ethanol as yellow solid in 16% yield. MS: M=443.2 (M+H)$^+$

Example 11

6-Methoxymethyl-3-(pyrimidin-5-ylamino)-pyridine-2-carboxylic acid [2-(2-hydroxy-ethyl)-5-pyridin-2-yl-2H-pyrazol-3-yl]-amide

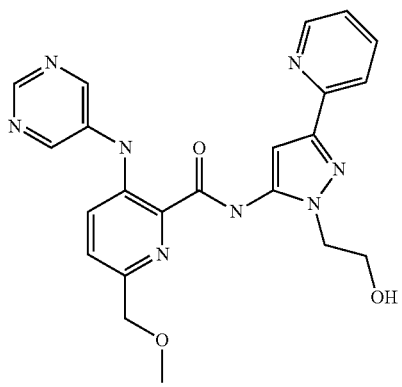 [SMILES: COCc1ccc(Nc2cncnc2)c(C(=O)Nc2cc(-c3ccccn3)nn2CCO)n1]

According to the method described in example 1, the title compound was obtained starting from intermediate A-3 and 2-(5-amino-3-pyridin-2-yl-pyrazol-1-yl)-ethanol as yellow solid in 18% yield. MS: M=447.3 (M+H)$^+$

Example 12

6-Cyclopropyl-3-(pyrimidin-5-ylamino)-pyridine-2-carboxylic acid [2-(2-dimethylamino-ethyl)-5-pyridin-2-yl-2H-pyrazol-3-yl]-amide

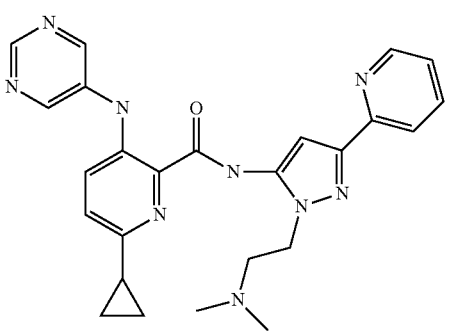 [SMILES: CN(C)CCn1nc(-c2ccccn2)cc1NC(=O)c1nc(C2CC2)ccc1Nc1cncnc1]

According to the method described in example 10, the title compound was obtained in two steps starting from dimethylaminoethylhydrazine dihydrochloride (1$^{st}$ step; 25% yield) and intermediate A-2 (2$^{nd}$ step; 29% yield) as yellow solid.

Example 13

2-Methoxymethyl-5-(pyrimidin-5-ylamino)-pyrimidine-4-carboxylic acid (2-methyl-5-pyridin-2-yl-2H-pyrazol-3-yl)-amide

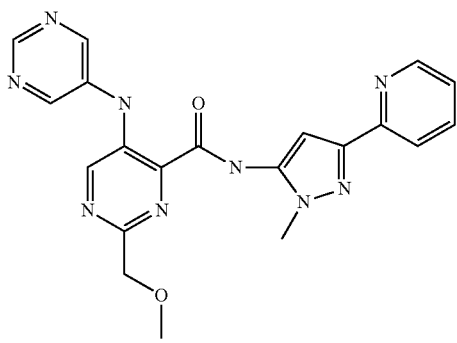 [SMILES: COCc1ncc(Nc2cncnc2)c(C(=O)Nc2cc(-c3ccccn3)nn2C)n1]

According to the method described in example 1, the title compound was obtained starting from intermediate A-4 and 1-methyl-3-pyridin-2-yl-1H-pyrazol-5-amine as yellow solid in 18% yield. MS: M=418.4 (M+H)+

Example 14

6-Cyclopropyl-3-(pyrimidin-5-ylamino)-pyridine-2-carboxylic acid (2-cyclohexyl-5-pyridin-2-yl-2H-pyrazol-3-yl)-amide

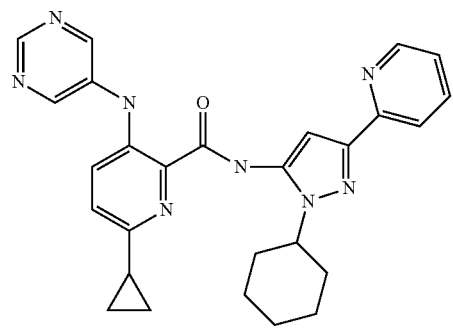 [SMILES: O=C(Nc1cc(-c2ccccn2)nn1C1CCCCC1)c1nc(C2CC2)ccc1Nc1cncnc1]

Step 1:
2-Cyclohexyl-5-pyridin-2-yl-2H-pyrazol-3-ylamine

According to the method described in step 1 of example 10, the title compound was obtained from cyclohexylhydrazine hydrochloride as off-white solid in 53% yield.
MS: M=243.2 (M+H)+

Step 2: 6-Cyclopropyl-3-(pyrimidin-5-ylamino)-pyridine-2-carboxylic acid (2-cyclohexyl-5-pyridin-2-yl-2H-pyrazol-3-yl)-amide To a suspension of 6-cyclopropyl-3-(pyrimidin-5-ylamino)-pyridine-2-carboxylic acid (50 mg, 0.2 mmol; intermediate A-5) at r.t under an argon atmosphere were added 2-cyclohexyl-5-pyridin-2-yl-2H-pyrazol-3-ylamine (47 mg, 0.2 mmol) and N-ethyldiisopropylamine (0.1 ml, 0.6 mmol). The yellow suspension was cooled to 0°, and propylphosphonic anhydride (0.31 ml, 1 mmol; 50% in AcOEt) was added. The suspension was stirred at 0° for 30 min. and at r.t overnight. The solvent was evaporated. After silica gel chromatography using a $CH_2Cl_2$/MeOH gradient, the product was obtained as yellow solid in 29% yield. MS: M=481.3 (M+H)+

Example 15

(5-{[6-Cyclopropyl-3-(pyrimidin-5-ylamino)-pyridine-2-carbonyl]-amino}-3-pyridin-2-yl-pyrazol-1-yl)-acetic acid ethyl ester

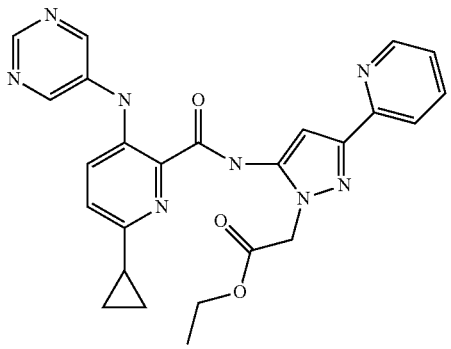 [SMILES: CCOC(=O)Cn1nc(-c2ccccn2)cc1NC(=O)c1nc(C2CC2)ccc1Nc1cncnc1]

According to the method described in example 14, the title compound was obtained in two steps starting from ethyl hydrazinoacetate hydrochloride (1st step; 22% yield) and intermediate A-5 (2nd step; 29% yield) as yellow solid.
MS: M=485.3 (M+H)+

Example 16

6-Cyclopropyl-3-(pyrimidin-5-ylamino)-pyridine-2-carboxylic acid [2-(2-morpholin-4-yl-ethyl)-5-pyridin-2-yl-2H-pyrazol-3-yl]-amide

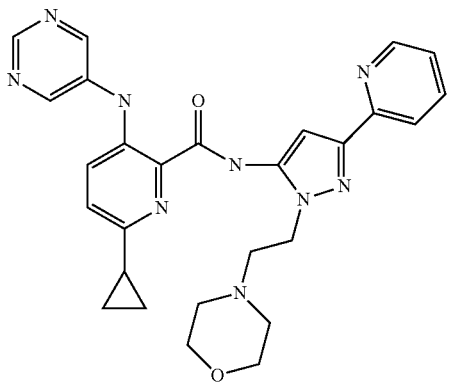 [SMILES: O=C(Nc1cc(-c2ccccn2)nn1CCN1CCOCC1)c1nc(C2CC2)ccc1Nc1cncnc1]

According to the method described in example 14, the title compound was obtained in two steps starting from (2-morpholin-4-yl-ethyl)-hydrazine (1st step; 23% yield) and intermediate A-5 (2nd step; 14% yield) as beige solid.
MS: M=512.4 (M+H)+

Example 17

6-Cyclopropyl-3-(pyrimidin-5-ylamino)-pyridine-2-carboxylic acid (2-phenethyl-5-pyridin-2-yl-2H-pyrazol-3-yl)-amide

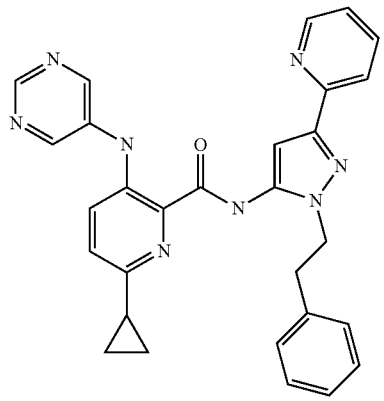 [SMILES: O=C(Nc1cc(-c2ccccn2)nn1CCc1ccccc1)c1nc(C2CC2)ccc1Nc1cncnc1]

Step 1: 2-Phenethyl-5-pyridin-2-yl-2H-pyrazol-3-ylamine

To a stirred solution of 3-oxo-3-pyridin-2-yl-propionitrile (0.46 g, 3.1 mmol; CAS 54123-21-6) at r.t. in EtOH (10 ml) under an argon atmosphere were added triethylamine (2.6 ml, 18.9 mmol) and phenelzine sulfate salt (2.2 g, 9.4 mmol). The mixture was heated to reflux and stirring was continued for 2 hrs. The orange solution was cooled to r.t. The solids were filtered off. The filtrate was concentrated to leave an orange viscous oil which was taken up in EtOAc and washed with water. The aqueous layer was extracted with EtOAc and with $CH_2Cl_2$/MeOH 9:1. The combined organics were dried over $MgSO_4$, filtered and concentrated. The product was obtained after silica gel chromatography using $CH_2Cl_2$/MeOH as gradient as off-white solid (0.722 g, 87%). MS: M=265.1 $(M+H)^+$

Step 2: 6-Cyclopropyl-3-(pyrimidin-5-ylamino)-pyridine-2-carboxylic acid (2-phenethyl-5-pyridin-2-yl-2H-pyrazol-3-yl)-amide According to the method described in step 2 of example 14, the title compound was obtained from intermediate A-5 and 2-phenethyl-5-pyridin-2-yl-2H-pyrazol-3-ylamine as light yellow solid in 21% yield. MS: M=503.3 $(M+H)^+$

Example 18

6-Cyclopropyl-3-(pyrimidin-5-ylamino)-pyridine-2-carboxylic acid (2-tert-butyl-5-pyridin-2-yl-2H-pyrazol-3-yl)-amide

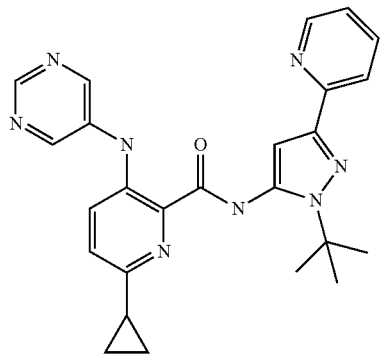 [SMILES: CC(C)(C)n1nc(-c2ccccn2)cc1NC(=O)c1nc(C2CC2)ccc1Nc1cncnc1]

Step 1: 2-tert-Butyl-5-pyridin-2-yl-2H-pyrazol-3-ylamine

To a stirred solution of 3-oxo-3-pyridin-2-yl-propionitrile (0.40 g, 2.7 mmol; CAS 54123-21-6) at r.t. in EtOH (10 ml) under an argon atmosphere were added triethylamine (1.1 ml, 8.2 mmol) and t-butylhydrazine hydrochloride (1.02 g, 8.2 mmol). The mixture was heated to reflux and stirring was continued for 2 hrs. The orange solution was cooled to r.t. The solids were filtered off. The filtrate was concentrated to leave an orange viscous oil which was taken up in EtOAc and washed with water. The aqueous layer was extracted with EtOAc and with $CH_2Cl_2$/MeOH 9:1. The combined organics were dried over $MgSO_4$, filtered and concentrated. After silica gel chromatography using $CH_2Cl_2$/MeOH as gradient, the product was obtained as off-white solid (0.366 g, 62%).
MS: M=265.1 $(M+H)^+$

Step 2: 6-Cyclopropyl-3-(pyrimidin-5-ylamino)-pyridine-2-carboxylic acid (2-tert-butyl-5-pyridin-2-yl-2H-pyrazol-3-yl)-amide According to the method described in example 1, the title compound was obtained from 2-tert-butyl-5-pyridin-2-yl-2H-pyrazol-3-ylamine and intermediate A-2 as light yellow solid in 39% yield. MS: M=455.3 $(M+H)^+$

Example 19

6-Ethyl-3-(pyrimidin-5-ylamino)-pyridine-2-carboxylic acid (2-methyl-5-pyridin-2-yl-2H-pyrazol-3-yl)-amide

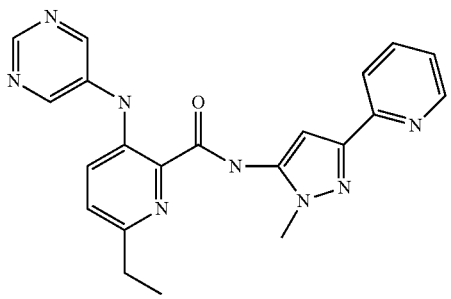 [SMILES: CCc1ccc(Nc2cncnc2)c(C(=O)Nc2cc(-c3ccccn3)nn2C)n1]

A solution of 2-methyl-5-pyridin-2-yl-2H-pyrazol-3-ylamine (0.1 g, 0.55 mmol) in dioxane (5 ml), cooled under inert gas atmosphere to 0° C., was treated with trimethylaluminium (0.275 ml, 2M heptane solution) and stirred at ambient temperature for 2 h. Intermediate A-6 (0.05 g, 0.18 mmol) was added in one portion and the resulting reaction mixture was heated at reflux for 24 hours. After cooling down to ambient temperature the solvent was evaporated. The final product was obtained after purification by preparative HPLC using a water/acetonitrile gradient and trituration with ethyl acetate as light yellow solid (7 mg, 10%).
MS: M=401.4 $(M+H)^+$

Example 20

6-Cyclopropyl-3-(pyrimidin-5-ylamino)-pyridine-2-carboxylic acid [5-pyridin-2-yl-2-(tetrahydro-pyran-4-yl)-2H-pyrazol-3-yl]-amide

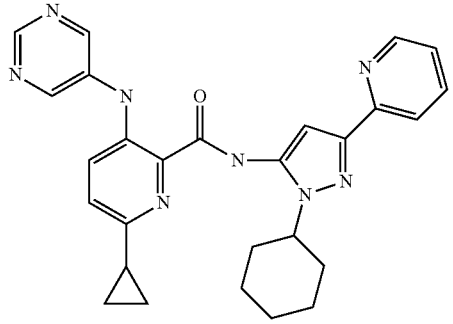 [SMILES: O=C(Nc1cc(-c2ccccn2)nn1C1CCCCC1)c1nc(C2CC2)ccc1Nc1cncnc1]

According to the method described in example 14, the title compound was obtained in two steps starting from (tetrahydro-pyran-4-yl)-hydrazine hydrochloride (1$^{st}$ step; 10% yield) and intermediate A-5 (2$^{nd}$ step; 11% yield) as yellow solid.

MS: M=483.2 (M+H)$^+$

Example 21

6-Cyclopropyl-3-(pyrimidin-5-ylamino)-pyrazine-2-carboxylic acid (2-methyl-5-pyridin-2-yl-2H-pyrazol-3-yl)-amide

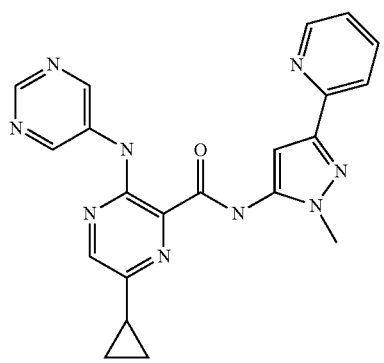 [SMILES: Cn1nc(-c2ccccn2)cc1NC(=O)c1nc(C2CC2)cnc1Nc1cncnc1]

According to the method described in example 19, the title compound was obtained starting from A-7 and 2-methyl-5-pyridin-2-yl-2H-pyrazol-3-ylamine after silica gel chromatography and preparative HPLC purification as yellow solid in 21% yield.

MS: M=414.3 (M+H)$^+$

Example 22

6-Cyclopropyl-3-(pyrimidin-5-ylamino)-pyridine-2-carboxylic acid [5-pyridin-2-yl-2-(2,2,2-trifluoro-ethyl)-2H-pyrazol-3-yl]-amide

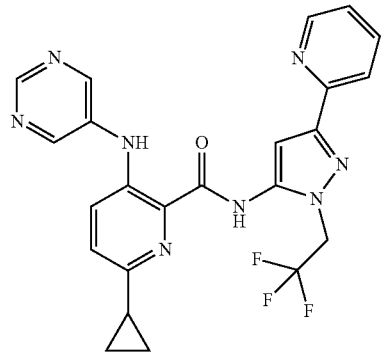 [SMILES: O=C(Nc1cc(-c2ccccn2)nn1CC(F)(F)F)c1nc(C2CC2)ccc1Nc1cncnc1]

According to the method described in example 10, the title compound was obtained in two steps starting from 2,2,2-trifluoroethylhydrazine (70% aqueous solution; 1$^{st}$ step, 29% yield) and intermediate A-2 (2$^{nd}$ step; 59% yield) as off-white solid.

MS: M=481.2 (M+H)$^+$

Example 23

6-Cyclopropyl-3-(pyrimidin-5-ylamino)-pyridine-2-carboxylic acid (2-propyl-5-pyridin-2-yl-2H-pyrazol-3-yl)-amide

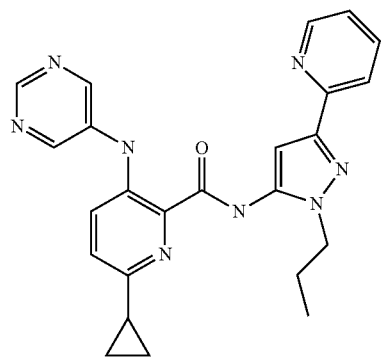 [SMILES: CCCn1nc(-c2ccccn2)cc1NC(=O)c1nc(C2CC2)ccc1Nc1cncnc1]

According to the method described in example 17, the title compound was obtained in two steps starting from propylhydrazine oxalate (1$^{st}$ step; 70% yield) and intermediate A-5 (2$^{nd}$ step; 33% yield) as yellow solid.

MS: M=439.3 (M–H)$^-$

Example 24

6-Cyclopropyl-3-(pyrimidin-5-ylamino)-pyridine-2-carboxylic acid [5-(6-chloro-pyridin-2-yl)-2-(2-hydroxy-ethyl)-2H-pyrazol-3-yl]-amide

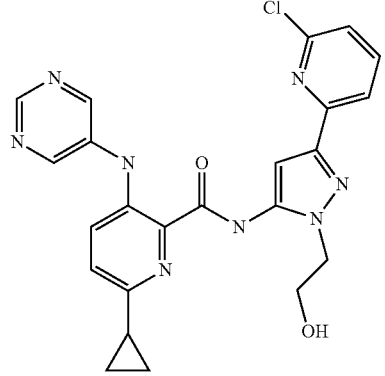 [SMILES: O=C(Nc1cc(-c2cccc(Cl)n2)nn1CCO)c1nc(C2CC2)ccc1Nc1cncnc1]

Step 1: 3-(6-Chloro-pyridin-2-yl)-3-oxo-propionitrile

A suspension of NaH (1.03 g, 26 mmol; 60% in mineral oil) in toluene (30 ml) was heated to 65° under an argon atmosphere. A solution of 6-chloro-pyridine-2-carboxylic acid methyl ester (4.4 g, 26 mmol) and acetonitrile (1.33 ml, 26 mmol) in toluene (20 ml; heating was required to dissolve the ester) was then added dropwise (exothermic), and the mixture was stirred at 65° for 24 h (compact slurry). After cooling to r.t., ice water was added while stirring. The aqueous phase was collected, washed with Et$_2$O, neutralized with HCl, extracted with CH$_2$Cl$_2$, dried over MgSO$_4$, filtered and evaporated. The product was obtained after silica gel chromatography using a CH$_2$Cl$_2$/MeOH gradient (2.04 g, 40%) as brown solid.
MS: M=181.2 (M+H)$^+$

Step 2: 2-[5-Amino-3-(6-chloro-pyridin-2-yl)-pyrazol-1-yl]-ethanol

According to the method described in step 1 of example 10, the title compound was obtained from 3-(6-chloro-pyridin-2-yl)-3-oxo-propionitrile and 2-hydroxyethyl-hydrazine as light brown solid in 64% yield. MS: M=239.0 (M+H)$^+$

Step 2: 6-Cyclopropyl-3-(pyrimidin-5-ylamino)-pyridine-2-carboxylic acid [5-(6-chloro-pyridin-2-yl)-2-(2-hydroxy-ethyl)-2H-pyrazol-3-yl]-amide According to the method described in example 1, the title compound was obtained from intermediate A-2 and 2-[5-amino-3-(6-chloro-pyridin-2-yl)-pyrazol-1-yl]-ethanol as yellow solid in 8% yield.
MS: M=477.15 (M+H)$^+$

Example 25

6-Cyclopropyl-3-(pyrimidin-5-ylamino)-pyridine-2-carboxylic acid [2-(2-hydroxy-ethyl)-5-quinolin-2-yl-2H-pyrazol-3-yl]-amide

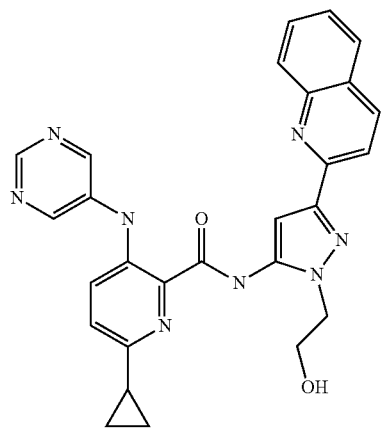 [SMILES: O=C(Nc1cc(-c2ccc3ccccc3n2)nn1CCO)c1nc(C2CC2)ccc1Nc1cncnc1]

Step 1: 2-(5-Amino-3-quinolin-2-yl-pyrazol-1-yl)-ethanol

According to the methods described in step 1 and 2 of example 24, the title compound was obtained from quinoline-2-carboxylic acid methyl ester (1$^{st}$ step; 43% yield) and 2-hydroxyethyl-hydrazine (2$^{nd}$ step; 42% yield) as off-white solid. MS: M=255.2 (M+H)$^+$

Step 2: 2-[5-Amino-3-(6-chloro-pyridin-2-yl)-pyrazol-1-yl]-ethanol

According to the method described in step 2 of example 14, the title compound was obtained from intermediate A-5 and 2-(5-amino-3-quinolin-2-yl-pyrazol-1-yl)-ethanol in 5% yield as yellow solid. MS: M=493.2 (M+H)$^+$

Example 26

6-Cyclopropyl-3-(pyrimidin-5-ylamino)-pyridine-2-carboxylic acid [5-(5-chloro-pyridin-2-yl)-2-(2-hydroxy-ethyl)-2H-pyrazol-3-yl]-amide

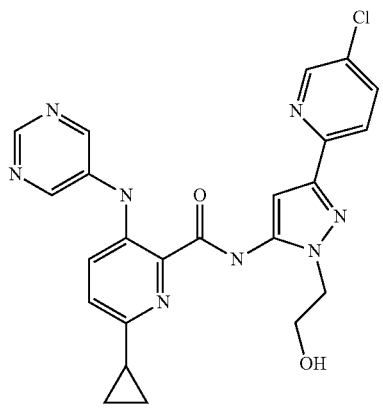 [SMILES: O=C(Nc1cc(-c2ccc(Cl)cn2)nn1CCO)c1nc(C2CC2)ccc1Nc1cncnc1]

According to the methods described in of example 24, the title compound was obtained from 5-chloro-pyridine-2-carboxylic acid methyl ester (1$^{st}$ step; 13% yield), 2-hydroxyethyl-hydrazine (2$^{nd}$ step; 64% yield) and intermediate A-5 (3$^{rd}$ step; 23% yield) as off-white solid.
MS: M=477.15 (M+H)$^+$

Example 27

6-Cyclopropyl-3-(pyrimidin-5-ylamino)-pyridine-2-carboxylic acid (2-isopropyl-5-pyridin-2-yl-2H-pyrazol-3-yl)-amide

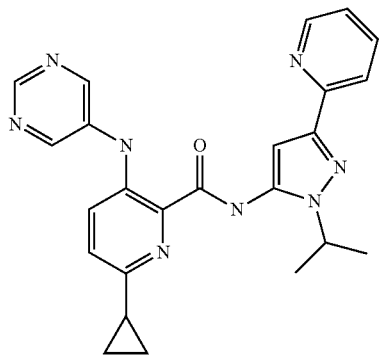 [SMILES: CC(C)n1nc(-c2ccccn2)cc1NC(=O)c1nc(C2CC2)ccc1Nc1cncnc1]

According to the method described in example 17, the title compound was obtained in two steps starting from isopropylhydrazine hydrochloride (1$^{st}$ step; 76% yield) and intermediate A-5 (2$^{nd}$ step; 22% yield) as yellow solid. MS: M=441.3 (M+H)$^+$

Example 28
6-Cyclopropyl-3-(pyrimidin-5-ylamino)-pyridine-2-carboxylic acid (2-isobutyl-5-pyridin-2-yl-2H-pyrazol-3-yl)-amide

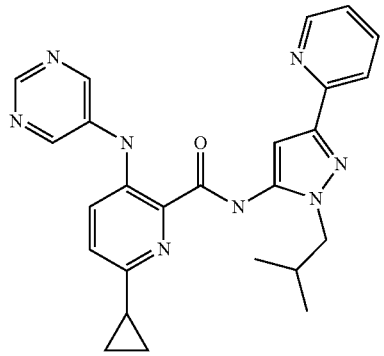 [SMILES: CC(C)Cn1nc(-c2ccccn2)cc1NC(=O)c1nc(C2CC2)ccc1Nc1cncnc1]

According to the method described in example 17, the title compound was obtained in two steps starting from 2-methyl-propylhydrazine hydrochloride (1$^{st}$ step; 61% yield) and intermediate A-5 (2$^{nd}$ step; 26% yield) as yellow solid. MS: M=455.3 (M+H)$^+$

Example 29
6-Cyclopropyl-3-(pyrimidin-5-ylamino)-pyridine-2-carboxylic acid (2-benzyl-5-pyridin-2-yl-2H-pyrazol-3-yl)-amide

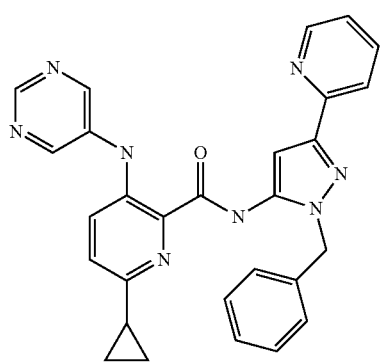 [SMILES: O=C(Nc1cc(-c2ccccn2)nn1Cc1ccccc1)c1nc(C2CC2)ccc1Nc1cncnc1]

According to the method described in example 17, the title compound was obtained in two steps starting from benzylhydrazine dihydrochloride (1$^{st}$ step; 74% yield) and intermediate A-5 (2$^{nd}$ step; 6% yield) as off-white solid. MS: M=489.4 (M+H)$^+$

Example 30
6-Cyclopropyl-3-(pyrimidin-5-ylamino)-pyridine-2-carboxylic acid (2-ethyl-5-pyridin-2-yl-2H-pyrazol-3-yl)-amide

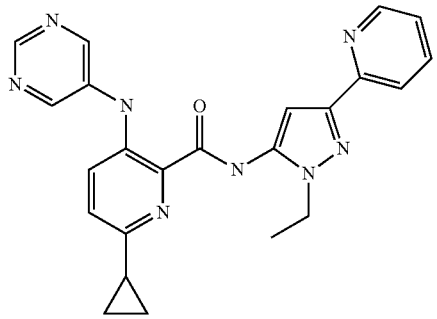 [SMILES: CCn1nc(-c2ccccn2)cc1NC(=O)c1nc(C2CC2)ccc1Nc1cncnc1]

According to the method described in example 18, the title compound was obtained in two steps starting from ethyl hydrazine oxalate (1$^{st}$ step) and intermediate A-2 (2$^{nd}$ step) as light-yellow solid. MS: M=427.2 (M+H)$^+$

Example 31
6-Cyclopropyl-3-(pyrimidin-5-ylamino)-pyridine-2-carboxylic acid (2-cyclopentylmethyl-5-pyridin-2-yl-2H-pyrazol-3-yl)-amide

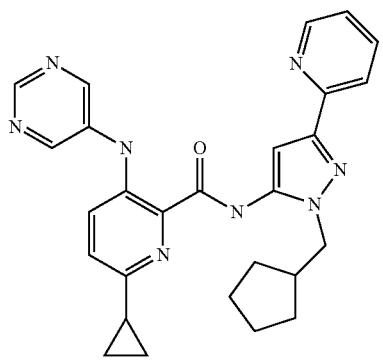 [SMILES: O=C(Nc1cc(-c2ccccn2)nn1CC1CCCC1)c1nc(C2CC2)ccc1Nc1cncnc1]

According to the method described in example 17, the title compound was obtained in two steps starting from 1-(cyclopentylmethyl)hydrazine dihydrochloride (1$^{st}$ step; 33% yield) and intermediate A-5 (2$^{nd}$ step; 8% yield) as yellow solid. MS: M=481.3 (M+H)$^+$

Example 32
6-Cyclopropyl-3-(pyrimidin-5-ylamino)-pyridine-2-carboxylic acid (2-cyclohexylmethyl-5-pyridin-2-yl-2H-pyrazol-3-yl)-amide

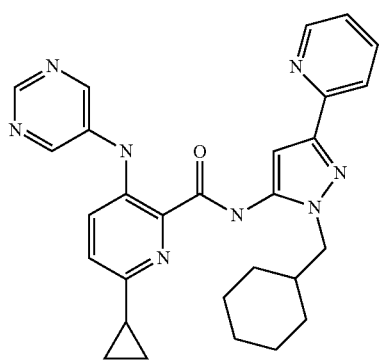 [SMILES: O=C(Nc1cc(-c2ccccn2)nn1CC1CCCCC1)c1nc(C2CC2)ccc1Nc1cncnc1]

According to the method described in example 17, the title compound was obtained in two steps starting from 1-(cyclohexylmethyl)hydrazine dihydrochloride (1$^{st}$ step; 53% yield) and intermediate A-5 (2$^{nd}$ step; 28% yield) as yellow solid. MS: M=495.3 (M+H)$^+$

Example 33

6-Cyclopropyl-3-(pyrimidin-5-ylamino)-pyridine-2-carboxylic acid [2-(2-cyano-ethyl)-5-pyridin-2-yl-2H-pyrazol-3-yl]-amide

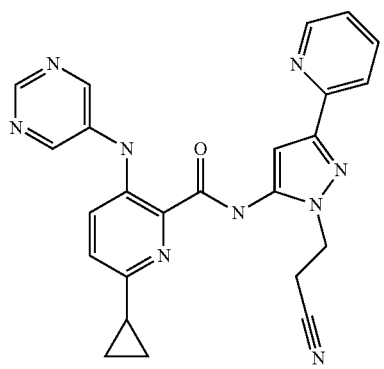 [SMILES: N#CCCn1nc(-c2ccccn2)cc1NC(=O)c1nc(C2CC2)ccc1Nc1cncnc1]

According to the method described in example 14, the title compound was obtained in two steps starting from 2-cyano-ethylhydrazine (1$^{st}$ step; 55% yield) and intermediate A-5 (2$^{nd}$ step; 26% yield) as yellow solid. MS: M=452.3 (M+H)$^+$

Example 34

6-Ethyl-3-(pyrimidin-5-ylamino)-pyridine-2-carboxylic acid [2-(2-hydroxy-ethyl)-5-pyridin-2-yl-2H-pyrazol-3-yl]-amide

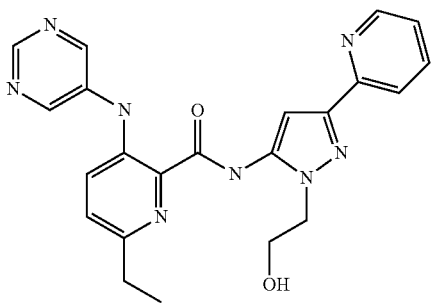 [SMILES: CCc1ccc(Nc2cncnc2)c(C(=O)Nc2cc(-c3ccccn3)nn2CCO)n1]

To a solution of intermediate A-14 (50 mg, 0.2 mmol) in DMF (2 ml) was added TBTU (75 mg, 0.23 mmol), N,N-diisopropyl ethyl amine (174 μl, 1.0 mmol) and 2-(5-amino-3-pyridin-2-yl-pyrazol-1-yl)-ethanol (46 mg, 0.23 mmol; see example 10, step 1). The reaction mixture was stirred at ambient temperature overnight, partitioned between ethyl acetate and water and extracted. The combined organic phases were washed with water and brine, dried and evaporated. The resulting residue was dissolved in ethyl acetate, washed with aqueous 10% potassium bisulfate, water and brine and the combined organic phases were dried and evaporated. The final product was obtained after purification by silica gel chromatography using a heptane/ethyl acetate gradient as light yellow solid (8 mg, 9%). MS: M=431.3 (M+H)$^+$

Example 35

6-Methyl-3-(pyrimidin-5-ylamino)-pyrazine-2-carboxylic acid (2-methyl-5-pyridin-2-yl-2H-pyrazol-3-yl)-amide

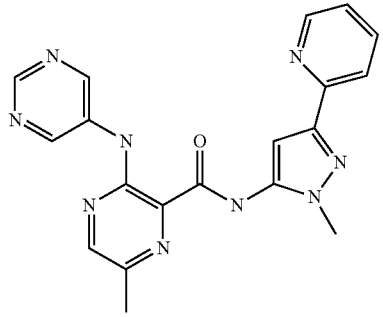 [SMILES: Cc1cnc(Nc2cncnc2)c(C(=O)Nc2cc(-c3ccccn3)nn2C)n1]

According to the method described in example 34, the title compound was obtained starting from A-8 and 2-methyl-5-pyridin-2-yl-2H-pyrazol-3-ylamine after aqueous work-up as precipitating yellow material without chromatographic purification in 15% yield.
MS: M=388.3 (M+H)$^+$

Example 36

6-Methyl-3-(pyrimidin-5-ylamino)-pyrazine-2-carboxylic acid [2-(2-hydroxy-ethyl)-5-pyridin-2-yl-2H-pyrazol-3-yl]-amide

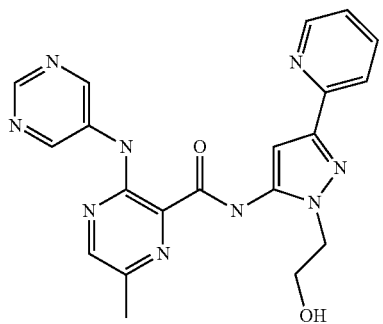 [SMILES: Cc1cnc(Nc2cncnc2)c(C(=O)Nc2cc(-c3ccccn3)nn2CCO)n1]

According to the method described in example 34, the title compound was obtained starting from A-8 and 2-(5-amino-3-pyridin-2-yl-pyrazol-1-yl)-ethanol (see example 10, step 1) after preparative HPLC purification as light yellow solid in 9% yield.
MS: M=418.4 (M+H)$^+$

Example 37

6-Cyclopropyl-3-(pyrimidin-5-ylamino)-pyridine-2-carboxylic acid [2-(3-methyl-3H-imidazol-4-ylm-ethyl)-5-pyridin-2-yl-2H-pyrazol-3-yl]-amide

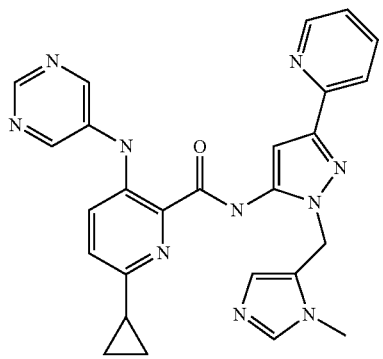 [SMILES: Cn1cncc1Cn1nc(-c2ccccn2)cc1NC(=O)c1nc(C2CC2)ccc1Nc1cncnc1]

According to the method described in example 17, the title compound was obtained in two steps starting from (3-methyl-3H-imidazol-4-ylmethyl)-hydrazine dihydrochloride (1st step; 67% yield) and intermediate A-5 (2nd step; 15% yield) as light yellow solid. MS: M=493.4 (M+H)+

Example 38

6-Cyclopropyl-3-(pyrimidin-5-ylamino)-pyridine-2-carboxylic acid [2-(2-methoxy-ethyl)-5-pyridin-2-yl-2H-pyrazol-3-yl]-amide

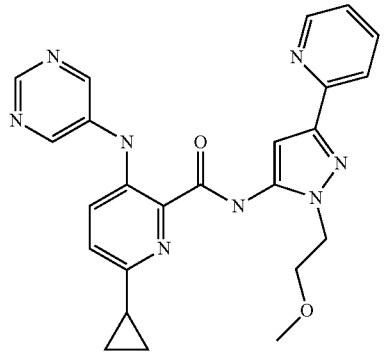 [SMILES: COCCn1nc(-c2ccccn2)cc1NC(=O)c1nc(C2CC2)ccc1Nc1cncnc1]

According to the method described in example 17, the title compound was obtained in two steps starting from 2-(methoxyethyl)hydrazine dihydrochloride (1st step; 73% yield) and intermediate A-5 (2nd step; 28% yield) as yellow solid. MS: M=457.3 (M+H)+

Example 39

6-Cyclopropyl-3-(pyrimidin-5-ylamino)-pyridine-2-carboxylic acid [5-(5-chloro-pyridin-2-yl)-2-methyl-2H-pyrazol-3-yl]-amide

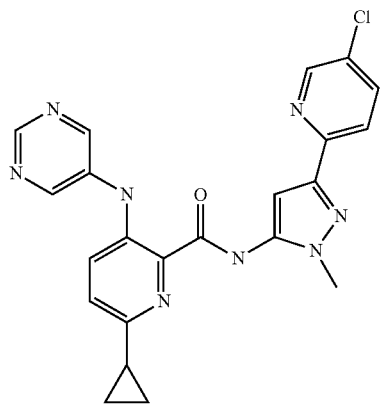 [SMILES: Cn1nc(-c2ccc(Cl)cn2)cc1NC(=O)c1nc(C2CC2)ccc1Nc1cncnc1]

According to the methods described in of example 24, the title compound was obtained from 5-chloro-pyridine-2-carboxylic acid methyl ester (1st step; 13% yield), methylhydrazine (2nd step; 75% yield) and intermediate A-2 (3rd step; 15% yield) as yellow solid. MS: M=447.3 (M+H)+

Example 40

6-Cyclopropyl-3-(pyrimidin-5-ylamino)-pyridine-2-carboxylic acid (2-methyl-5-quinolin-2-yl-2H-pyrazol-3-yl)-amide

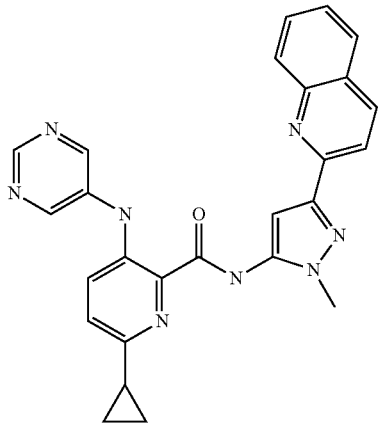 [SMILES: Cn1nc(-c2ccc3ccccc3n2)cc1NC(=O)c1nc(C2CC2)ccc1Nc1cncnc1]

According to the methods described in of example 25, the title compound was obtained from quinoline-2-carboxylic acid methyl ester (1st step; 43% yield), methylhydrazine (2nd step; 83% yield) and intermediate A-5 (3rd step; 47% yield) as yellow solid. MS: M=463.3 (M+H)+

Example 41

6-Cyclopropyl-3-(pyrimidin-5-ylamino)-pyridine-2-carboxylic acid [5-(6-chloro-pyridin-2-yl)-2-methyl-2H-pyrazol-3-yl]-amide

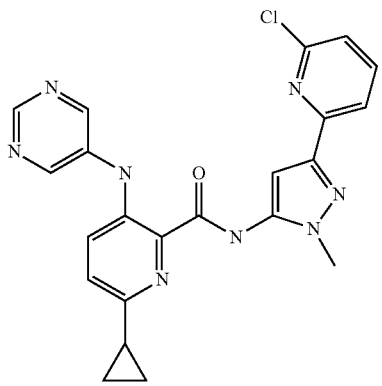 [SMILES: Cn1nc(-c2cccc(Cl)n2)cc1NC(=O)c1nc(C2CC2)ccc1Nc1cncnc1]

According to the methods described in of example 24, the title compound was obtained from 6-chloro-pyridine-2-carboxylic acid methyl ester (1st step; 40% yield), methylhydrazine (2nd step; 68% yield) and intermediate A-2 (3rd step; 25% yield) as yellow solid.

MS: M=447.3 (M+H)+

Example 42

6-Cyclopropyl-3-(pyrimidin-5-ylamino)-pyridine-2-carboxylic acid [1-(2-dimethylamino-ethyl)-5-pyridin-2-yl-1H-pyrazol-3-yl]-amide

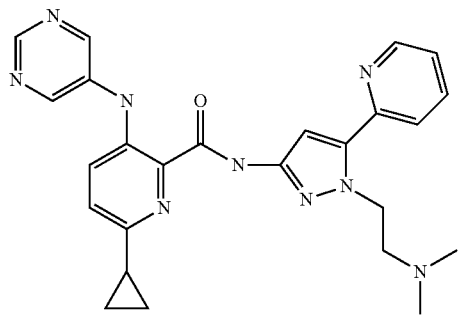 [SMILES: CN(C)CCn1nc(NC(=O)c2nc(C3CC3)ccc2Nc2cncnc2)cc1-c1ccccn1]

The title compound was isolated by silica gel chromatography as minor side product in the last step of the preparation of 6-cyclopropyl-3-(pyrimidin-5-ylamino)-pyridine-2-carboxylic acid [2-(2-dimethyl-amino-ethyl)-5-pyridin-2-yl-2H-pyrazol-3-yl]-amide (example 12).

MS: M=470.3 (M+H)$^+$

Example 43

6-Cyclopropyl-3-(pyrimidin-5-ylamino)-pyridine-2-carboxylic acid [2-(1-methyl-piperidin-4-yl)-5-pyridin-2-yl-2H-pyrazol-3-yl]-amide

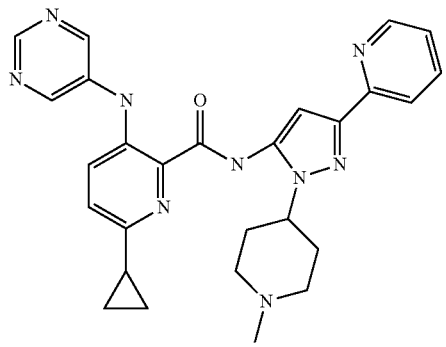 [SMILES: CN1CCC(n2nc(-c3ccccn3)cc2NC(=O)c2nc(C3CC3)ccc2Nc2cncnc2)CC1]

According to the method described in example 17, the title compound was obtained in two steps starting from (1-methyl-piperidin-4-yl)-hydrazine dihydrochloride (1$^{st}$ step; 68% yield) and intermediate A-5 (2$^{nd}$ step; 6% yield) as yellow solid. MS: M=496.3 (M+H)$^+$

Example 44

6-Cyclopropyl-3-(pyrimidin-5-ylamino)-pyridine-2-carboxylic acid [5-(4-methoxy-phenyl)-[1,3,4]thiadiazol-2-yl]-amide

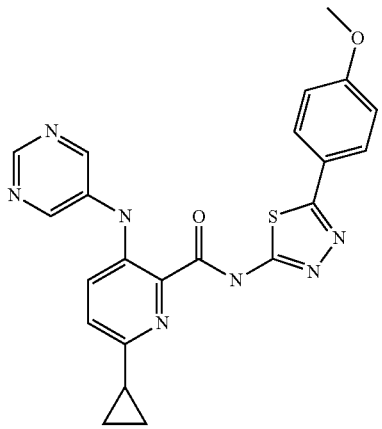 [SMILES: COc1ccc(-c2nnc(NC(=O)c3nc(C4CC4)ccc3Nc3cncnc3)s2)cc1]

To a solution of intermediate A-2 (50 mg, 0.2 mmol) and 5-(4-methoxy-phenyl)-[1,3,4]thiadiazol-2-ylamine (73 mg, 0.4 mmol) in dioxane (1.5 ml) was added trimethylaluminium (0.176 ml, 2M heptane solution) under inert gas atmosphere. The resulting reaction mixture was heated at reflux overnight. The final product was obtained after purification by preparative HPLC using a water/acetonitrile gradient as yellow solid (4 mg, 5%).

MS: M=446.1 (M+H)$^+$

Example 45

6-Cyclopropyl-3-(pyrimidin-5-ylamino)-pyridine-2-carboxylic acid [5-(4-fluoro-phenyl)-[1,3,4]thiadiazol-2-yl]-amide

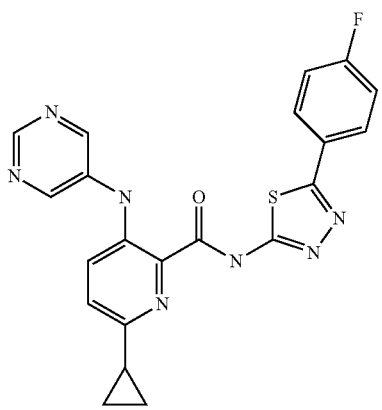 [SMILES: O=C(Nc1nnc(-c2ccc(F)cc2)s1)c1nc(C2CC2)ccc1Nc1cncnc1]

According to the method described in example 44, the title compound was obtained starting from A-2 and 5-(4-fluorophenyl)-[1,3,4]thiadiazol-2-ylamine after preparative HPLC purification as yellow solid in 17% yield. MS: M=434.3 (M+H)+

Example 46

6-Cyclopropyl-3-(pyrimidin-5-ylamino)-pyridine-2-carboxylic acid (3-phenyl-isoxazol-5-yl)-amide

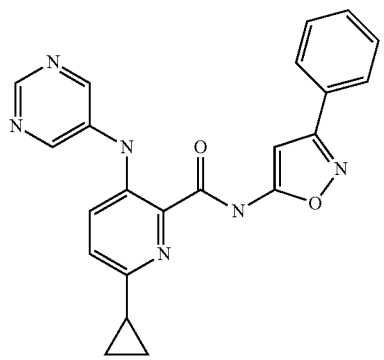 [SMILES: O=C(Nc1cc(-c2ccccc2)no1)c1nc(C2CC2)ccc1Nc1cncnc1]

According to the method described in example 44, the title compound was obtained starting from A-2 and 3-phenyl-isoxazol-5-ylamine after preparative HPLC purification as yellow solid in 22% yield. MS: M=399.2 (M+H)+

Example 47

6-Cyclopropyl-3-(pyrimidin-5-ylamino)-pyridine-2-carboxylic acid (5-phenyl-isoxazol-3-yl)-amide

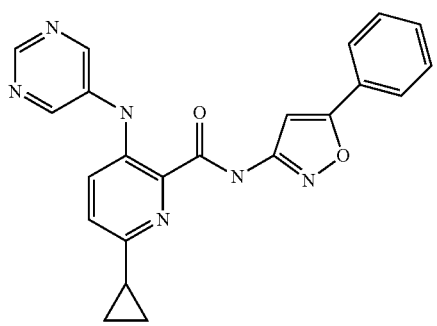 [SMILES: O=C(Nc1cc(-c2ccccc2)on1)c1nc(C2CC2)ccc1Nc1cncnc1]

Step 1: 5-phenyl-isoxazol-3-ylamine

This amine was obtained from either benzoylacetonitrile or phenylpropiolonitrile as commercially available starting materials according to known literature procedures (Heterocycles 1991, 32 (6), 1153; J. Chem. Soc., Perkin Trans. 1, 1984 (5), 1079; Chem. Pharm. Bull. 1966, 14 (11), 1277) as solid material. MS: M=161.3 (M+H)+

Step 2: 6-Cyclopropyl-3-(pyrimidin-5-ylamino)-pyridine-2-carboxylic acid (5-phenyl-isoxazol-3-yl)-amide According to the method described in example 44, the title compound was obtained starting from A-2 and 5-phenyl-isoxazol-3-ylamine after preparative HPLC purification as yellow solid in 9% yield. MS: M=399.2 (M+H)+

Example 48

6-Cyclopropyl-3-(pyrimidin-5-ylamino)-pyridine-2-carboxylic acid (5-phenyl-[1,3,4]thiadiazol-2-yl)-amide

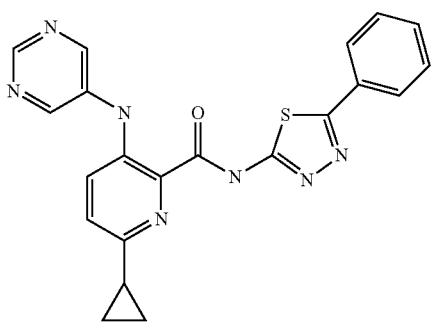 [SMILES: O=C(Nc1nnc(-c2ccccc2)s1)c1nc(C2CC2)ccc1Nc1cncnc1]

To a solution of intermediate A-5 (42 mg, 0.16 mmol) in DMF (2 ml) was added TBTU (60 mg, 0.18 mmol), N,N-diisopropyl ethyl amine (139 µl, 0.8 mmol) and 5-phenyl-[1,3,4]thiadiazol-2-ylamine (32 mg, 0.18 mmol). The reaction mixture was stirred at ambient temperature overnight. The final product was obtained after purification by preparative HPLC using a water/acetonitrile gradient as yellow solid (12 mg, 17%). MS: M=416.3 (M+H)+

Example 49

6-Cyclopropyl-3-(pyrimidin-5-ylamino)-pyridine-2-carboxylic acid (5-pyrazin-2-yl-[1,3,4]thiadiazol-2-yl)-amide

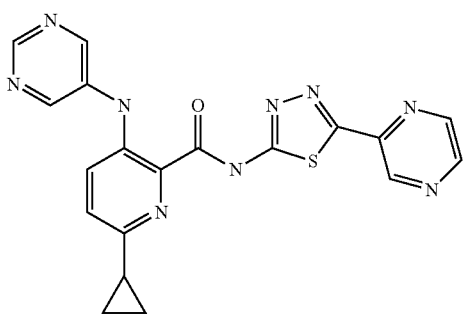 [SMILES: O=C(Nc1nnc(-c2cnccn2)s1)c1nc(C2CC2)ccc1Nc1cncnc1]

According to the method described in example 48, the title compound was obtained starting from A-5 and 5-pyrazin-2-yl-[1,3,4]thiadiazol-2-ylamine after preparative HPLC purification as yellow solid in 18% yield. MS: M=418.3 (M+H)+

Example 50

6-Cyclopropyl-3-(pyrimidin-5-ylamino)-pyridine-2-carboxylic acid (5-pyridin-2-yl-thiophen-2-yl)-amide

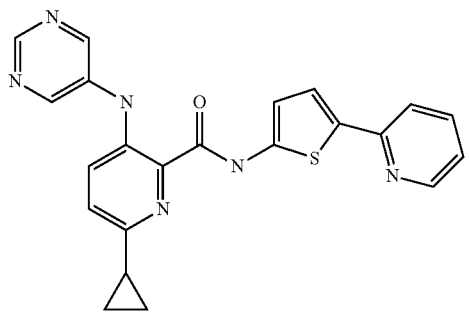 [SMILES: O=C(Nc1ccc(-c2ccccn2)s1)c1nc(C2CC2)ccc1Nc1cncnc1]

Step 1: 5-Pyridine-2-yl-thiophen-2-ylamine

This amine was obtained starting from commercially available 5-pyridin-2-yl-thiophene-2-carboxylic acid according to WO 2007/058942 as solid material in 27% yield for the two-step procedure. MS: M=177.2 (M+H)$^+$

Step 2: 6-Cyclopropyl-3-(pyrimidin-5-ylamino)-pyridine-2-carboxylic acid (5-pyridin-2-yl-thiophen-2-yl)-amide According to the method described in example 44, the title compound was obtained starting from A-2 and 5-pyridine-2-yl-thiophen-2-ylamine after preparative HPLC purification as solid material in 38% yield. MS: M=415.3 (M+H)$^+$

Example 51

6-Cyclopropyl-3-(pyrimidin-5-ylamino)-pyridine-2-carboxylic acid (3-pyridin-2-yl-isoxazol-5-yl)-amide

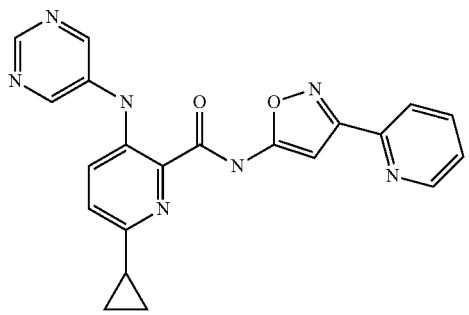 [SMILES: O=C(Nc1cc(-c2ccccn2)no1)c1nc(C2CC2)ccc1Nc1cncnc1]

According to the method described in example 44, the title compound was obtained starting from A-2 and 3-pyridin-2-yl-isoxazol-5-ylamine after preparative HPLC purification as solid material in 24% yield. MS: M=400.2 (M+H)$^+$

Example 52

6-Cyclopropyl-3-(pyrimidin-5-ylamino)-pyridine-2-carboxylic acid (1-pyridin-2-yl-1H-imidazol-4-yl)-amide

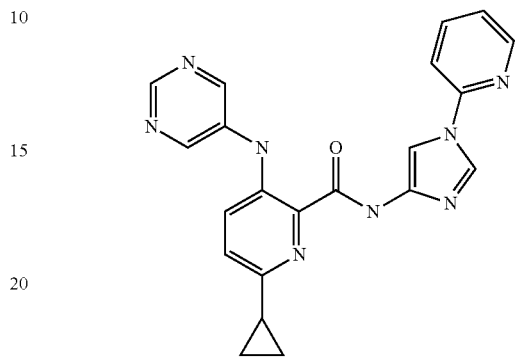

Step 1: 2-(4-Nitro-imidazol-1-yl)-pyridine

A suspension of 4-nitro-1H-imidazole (0.5 g, 4.4 mmol) in DMF (15 ml) was cooled to 0° C. and treated with sodium hydride (0.23 g, 5.3 mmol). Stirring was continued at 0° C. for 1 h and subsequently cooled to −30° C. A solution of N-fluoropyridinium triflate (0.55 g, 2.2 mmol) in DMF (10 ml) was added within 5 min. After warming-up to ambient temperature, the reaction mixture was stirred at that temperature overnight. The crude product was obtained after extraction with ethyl acetate (2×100 ml), washing of the combined organic phases with 10% aqueous potassium bisulphate solution, water and brine and finally drying and solvent evaporation. This off-white solid material (0.33 g, 39%) was used without any further purification for the next step. MS: M=191.3 (M+H)$^+$

Step 2: 1-Pyridin-2-yl-1H-imidazol-4-ylamine

To a solution of 2-(4-nitro-imidazol-1-yl)-pyridine (150 mg, 0.79 mmol) in THF (12 ml) was added under inert gas atmosphere 10% Pd/C (28 mg, 0.026 mmol). Upon evacuation, the reaction vessel was charged with hydrogen and the reaction mixture was stirred at ambient temperature overnight. The catalyst was filtered off, the solvent volume was reduced and the amine was used without any further purification as ~0.2 M THF solution for the next step.

MS: M=161.0 (M+H)$^+$

Step 3: 6-Cyclopropyl-3-(pyrimidin-5-ylamino)-pyridine-2-carboxylic acid (1-pyridin-2-yl-1H-imidazol-4-yl)-amide According to the method described in example 48, the title compound was obtained starting from A-5 and 1-pyridin-2- yl-1H-imidazol-4-ylamine (~0.2 M THF solution) after preparative HPLC purification as light yellow solid in 27% yield. MS: M=399.1 (M+H)+

Example 53

2-Isopropyl-5-(pyrimidin-5-ylamino)-pyrimidine-4-carboxylic acid (2-methyl-5-pyridin-2-yl-2H-pyrazol-3-yl)-amide

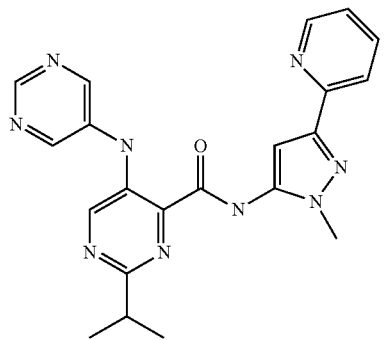 [SMILES: CC(C)c1ncc(Nc2cncnc2)c(C(=O)Nc2cc(-c3ccccn3)nn2C)n1]

According to the method described in example 1, the title compound was obtained starting from intermediate A-9 and 1-methyl-3-pyridin-2-yl-1H-pyrazol-5-amine as light yellow solid in 38% yield. MS: M=416.2 (M+H)+

Example 54

2-Cyclopropyl-5-(pyrimidin-5-ylamino)-pyrimidine-4-carboxylic acid (2-methyl-5-pyridin-2-yl-2H-pyrazol-3-yl)-amide

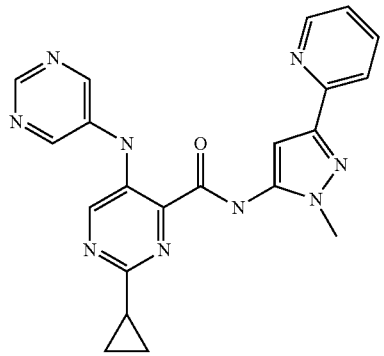 [SMILES: Cn1nc(-c2ccccn2)cc1NC(=O)c1nc(C2CC2)ncc1Nc1cncnc1]

According to the method described in example 1, the title compound was obtained starting from intermediate A-10 and 1-methyl-3-pyridin-2-yl-1H-pyrazol-5-amine as yellow solid in 50% yield. MS: M=414.2 (M+H)+

Example 55

2-tert-Butyl-5-(pyrimidin-5-ylamino)-pyrimidine-4-carboxylic acid (2-methyl-5-pyridin-2-yl-2H-pyrazol-3-yl)-amide

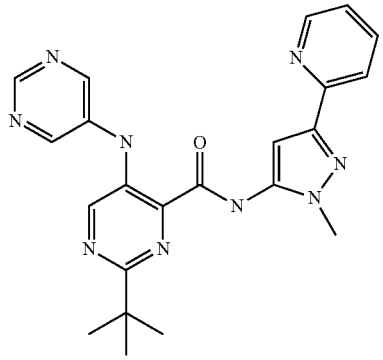 [SMILES: Cn1nc(-c2ccccn2)cc1NC(=O)c1nc(C(C)(C)C)ncc1Nc1cncnc1]

According to the method described in example 1, the title compound was obtained starting from intermediate A-11 and 1-methyl-3-pyridin-2-yl-1H-pyrazol-5-amine as yellow solid in 31% yield. MS: M=430.3 (M+H)+

Example 56

6-Cyclopropyl-3-(pyrimidin-5-ylamino)-pyridine-2-carboxylic acid [3-(4-chloro-phenyl)-isoxazol-5-yl]-amide

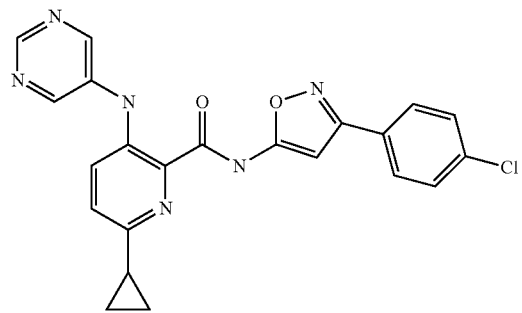 [SMILES: O=C(Nc1cc(-c2ccc(Cl)cc2)no1)c1nc(C2CC2)ccc1Nc1cncnc1]

To a solution of intermediate A-5 (30 mg, 0.12 mmol), HATU (49 mg, 0.13 mmol) and 3-(4-chloro-phenyl)-isoxazol-5-ylamine (25 mg, 0.13 mmol) in THF (1 ml) was added N-methylmorpholine (65 µl, 0.6 mmol). The reaction mixture was stirred at reflux overnight. The final product was obtained after purification by preparative HPLC using a water/acetonitrile gradient as light yellow solid (11 mg, 23%). MS: M=433.3 (M+H)+

Example 57

6-Cyclopropyl-3-(pyrimidin-5-ylamino)-pyridine-2-carboxylic acid [3-(4-bromo-phenyl)-isoxazol-5-yl]-amide

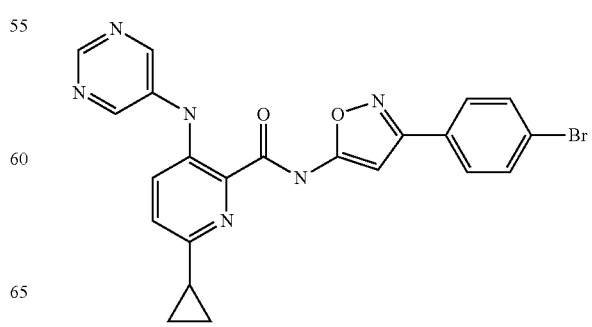

According to the method described in example 56, the title compound was obtained starting from A-5 and 3-(4-bromophenyl)-isoxazol-5-ylamine after preparative HPLC purification as light yellow solid in 52% yield. MS: M=477.1 (M+H)⁺

Example 58

6-Cyclopropyl-3-(pyrimidin-5-ylamino)-pyridine-2-carboxylic acid [3-(4-fluoro-phenyl)-isoxazol-5-yl]-amide

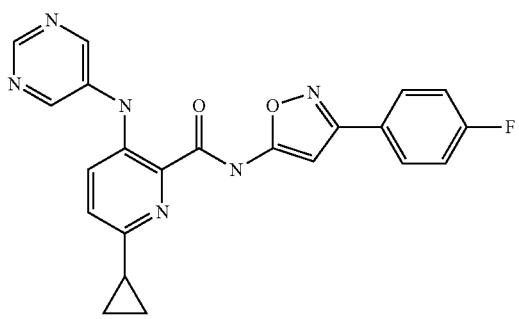 [SMILES: O=C(Nc1cc(-c2ccc(F)cc2)no1)c1nc(C2CC2)ccc1Nc1cncnc1]

According to the method described in example 56, the title compound was obtained starting from A-5 and 3-(4-fluorophenyl)-isoxazol-5-ylamine after preparative HPLC purification as light yellow solid in 14% yield. MS: M=417.3 (M+H)⁺

Example 59

6-Methoxymethyl-3-(pyrimidin-5-ylamino)-pyridine-2-carboxylic acid (2-methyl-5-pyridin-2-yl-2H-pyrazol-3-yl)-amide

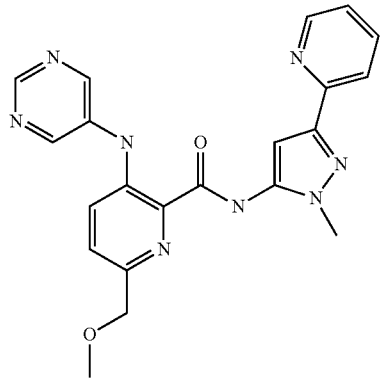 [SMILES: COCc1ccc(Nc2cncnc2)c(C(=O)Nc2cc(-c3ccccn3)nn2C)n1]

According to the method described in example 1, the title compound was obtained starting from intermediate A-3 and 1-methyl-3-pyridin-2-yl-1H-pyrazol-5-amine as light yellow solid in 18% yield. MS: M=417.2 (M+H)⁺

Example 60

2-Cyclohexyl-5-(pyrimidin-5-ylamino)-pyrimidine-4-carboxylic acid (2-methyl-5-pyridin-2-yl-2H-pyrazol-3-yl)-amide

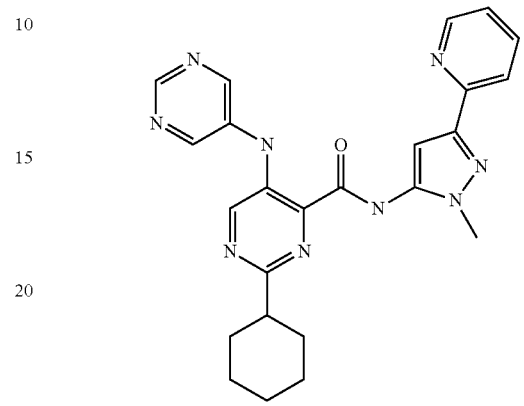

According to the method described in example 1, the title compound was obtained starting from intermediate A-12 and 1-methyl-3-pyridin-2-yl-1H-pyrazol-5-amine as yellow solid in 7% yield. MS: M=456.3 (M+H)⁺

Example 61

2-Isobutyl-5-(pyrimidin-5-ylamino)-pyrimidine-4-carboxylic acid (2-methyl-5-pyridin-2-yl-2H-pyrazol-3-yl)-amide

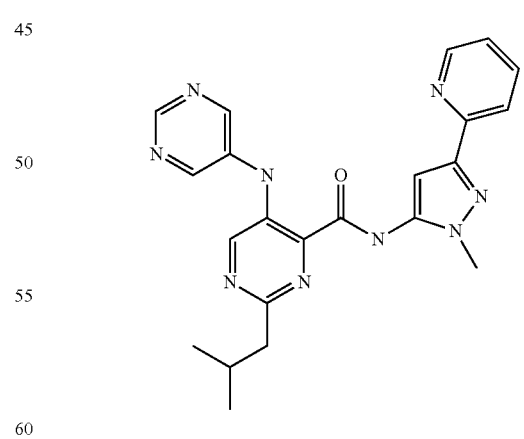

According to the method described in example 1, the title compound was obtained starting from intermediate A-13 and 1-methyl-3-pyridin-2-yl-1H-pyrazol-5-amine as yellow solid in 19% yield. MS: M=430.3 (M+H)⁺

Example 62

6-Cyclopropyl-3-(pyrimidin-5-ylamino)-pyridine-2-carboxylic acid (2-pyridin-2-yl-thiazol-5-yl)-amide

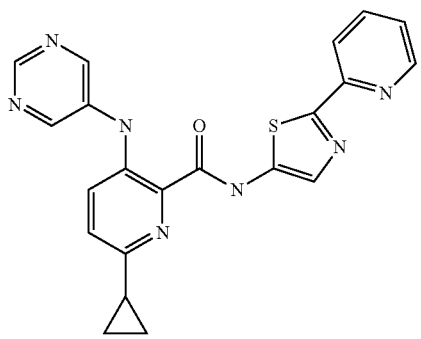 [SMILES: O=C(Nc1cnc(-c2ccccn2)s1)c1nc(C2CC2)ccc1Nc1cncnc1]

Step 1: 2-Pyridin-2-yl-thiazol-5-carboxylic acid methyl ester

To a suspension of 2-bromo-1,3-thiazole-5-carboxylic acid methyl ester (0.5 g, 2.25 mmol) and Pd(PPh$_3$)$_4$ (0.13 g, 0.11 mmol) in THF (12.5 ml) was added bromo-(pyridine-2-yl)-zinc (6.75 ml, 0.5M THF solution) under inert gas atmosphere. The reaction mixture was irradiated under microwave conditions at 120° C. for 10 min. The solvent was removed and the product was obtained after purification by silica gel chromatography using a heptane/ethyl acetate gradient as yellow crystals (0.34 g, 68%) MS: M=221.2 (M+H)$^+$

Step 2: 2-Pyridin-2-yl-thiazol-5-carboxylic acid

2-Pyridin-2-yl-thiazol-5-carboxylic acid methyl ester (0.34 g, 1.55 mmol) was dissolved in a THF/methanol (5 ml/1 ml) mixture, cooled to 0° C. and treated with lithium hydroxide (4.7 ml, 1N aqueous solution). The reaction mixture was allowed to warm-up to ambient temperature, stirred at that temperature for 30 min and the pH value was subsequently adjusted to ~5. The resulting suspension was treated with dichloromethane (50 ml) and filtered. The precipitate was washed with water and dichloromethane, the filtrate was extracted with dichloromethane. The combined organic phases were dried, evaporated and combined with the precipitate to yield the product as light brown solid (0.3 g, 92%). MS: M=161.1 (M-CO$_2$-H)$^-$

Step 3: (2-Pyridin-2-yl-thiazol-5-yl)-carbamic acid tert-butyl ester

A solution of 2-pyridin-2-yl-thiazol-5-carboxylic acid (250 mg, 1.2 mmol) in tert-butanol (4.5 ml) was treated with diphenylphosphoryl azide (0.4 ml, 1.85 mmol) and triethylamine (0.34 ml, 2.4 mmol) and stirred at 90° C. for 5 h. The reaction mixture was extracted with ethyl acetate and the combined organic phases were washed with saturated ammonium acetate solution, water and brine. The final product was obtained after purification by silica gel chromatography using a heptane/ethyl acetate gradient as yellow oil (180 mg, 54%). MS: M=278.2 (M+H)$^+$

Step 4: 2-Pyridin-2-yl-thiazol-5-ylamine

A solution of (2-pyridin-2-yl-thiazol-5-yl)-carbamic acid tert-butyl ester (200 mg, 0.72 mmol) in dioxane (3 ml) was treated with 4M HCl in dioxane (3 ml) and the resulting suspension was stirred at ambient temperature overnight. The reaction mixture was filtrated and the precipitate was dissolved in sodium hydroxide (20 ml, 0.5M aqueous solution) and extracted with dichloromethane. The combined organic phases were dried and the solvent was evaporated to yield the product as orange solid (78 mg, 60%) which was used without any further purification. MS: M=178.1 (M+H)$^+$

Step 5: 6-Cyclopropyl-3-(pyrimidin-5-ylamino)-pyridine-2-carboxylic acid (2-pyridin-2-yl-thiazol-5-yl)-amide To a solution of intermediate A-5 (40 mg, 0.16 mmol), HATU (66 mg, 0.17 mmol) and 2-pyridin-2-yl-thiazol-5-ylamine (39 mg, 0.22 mmol) in THF (1.5 ml) was added N-methylmorpholine (86 µl, 0.78 mmol). The reaction mixture was stirred at reflux overnight. The resulting suspension was filtered and the collected solid material was thoroughly washed with THF. The final product was obtained upon drying of the precipitate as yellow solid (40 mg, 61%). MS: M=416.2 (M+H)$^+$

Example 63

6-Cyclopropyl-3-(pyrimidin-5-ylamino)-pyridine-2-carboxylic acid (1-methyl-5-pyridin-2-yl-1H-pyrazol-3-yl)-amide

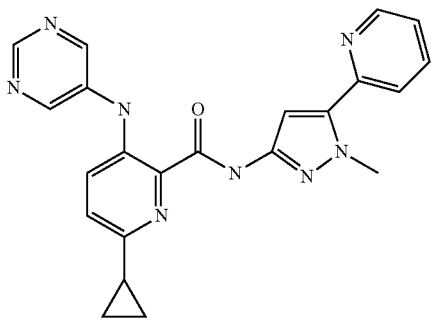 [SMILES: Cn1nc(NC(=O)c2nc(C3CC3)ccc2Nc2cncnc2)cc1-c1ccccn1]

Step 1: (Z)-4-Hydroxy-2-oxo-4-pyridin-2-yl-but-3-enoic acid ethyl ester

A solution of 2-acetylpyridine (5.0 g, 40 mmol) and diethyl oxalate (5.9 g, 40 mmol) in diethylether (75 ml) was cooled to 0° C. and treated with sodium ethylate (16.6 ml, 21% solution in ethanol). While stirring overnight, the reaction mixture was allowed to warm-up slowly to ambient temperature. The reaction mixture was acidified with acetic acid, diluted with water and extracted with diethylether. The combined organic phases were washed with water and brine, dried and evaporated. The isolated residue was triturated with heptane (30 ml) and diethylether (5 ml) for 2 h and the resulting suspension was filtrated to collect the product. This process was repeated to obtain the product as light brown solid (3.96 g, 44%). MS: M=220.1 (M-H)$^-$

Step 2: 1-Methyl-5-pyridin-2-yl-1H-pyrazole-3-carboxylic acid ethyl ester

To a stirred solution of (Z)-4-hydroxy-2-oxo-4-pyridin-2-yl-but-3-enoic acid ethyl ester (2.32 g, 10 mmol) at r.t. in EtOH (15 ml) under an argon atmosphere was added methylhydrazine (0.55 ml, 10 mmol). The mixture was heated to reflux and stirring was continued for 90 min. The mixture was cooled to r.t. and concentrated to leave a brown paste. After silica gel chromatography using a $CH_2Cl_2$/MeOH gradient, the product (1.43 g, 59%) was obtained as yellow waxy solid. MS: M=232.1 $(M+H)^+$

Step 3: 1-Methyl-5-pyridin-2-yl-1H-pyrazole-3-carboxylic acid

To a stirred solution of 1-methyl-5-pyridin-2-yl-1H-pyrazole-3-carboxylic acid ethyl ester (655 mg, 2.8 mmol) at r.t. in ethanol (6 ml) under an argon atmosphere was added 1 N NaOH (5.7 ml) in one portion. The mixture was stirred at r.t. for 5 hrs, neutralized by the addition of 1 N HCl and concentrated to leave a light brown solid. This was triturated in a mixture of $Et_2O$ (10 ml) and EtOH (1 ml). The suspension was stirred at r.t. for 2 h. The solids was collected by filtration, washed with $Et_2O$ and dried to give the title compound (0.79 g, 100% with 73% purity; impurity: NaCl) as light brown solid. MS: M=204.2 $(M+H)^+$

Step 4: (1-Methyl-5-pyridin-2-yl-1H-pyrazole-3-yl)-carbamic acid tert-butyl ester A solution of 1-methyl-5-pyridin-2-yl-1H-pyrazole-3-carboxylic acid (205 mg, 1.0 mmol) in tert-butanol (3.8 ml) was treated with diphenylphosphoryl azide (225 µl, 1.0 mmol) and triethylamine (280 µl, 2.0 mmol) and stirred at 90° C. for 24 hours. Since the reaction was not completed, another equivalent of diphenylphosphoryl azide (225 µl) and two equivalents of triethylamine (280 µl) were added and stirring was continued at 90° C. for another 24 hours. The crude product was purified by silica gel chromatography using a heptane/ethyl acetate gradient and the final product was obtained as off-white solid (66 mg, 24%).

MS: M=219.3 $(M-C_4H_8+H)^+$

Step 5: 1-Methyl-5-pyridin-2-yl-1H-pyrazole-3-ylamine

A solution of (1-methyl-5-pyridin-2-yl-1H-pyrazole-3-yl)-carbamic acid tert-butyl ester (82 mg, 0.30 mmol) in dioxane (0.85 ml) was treated with 4M HCl in dioxane (0.85 ml) and the resulting suspension was stirred at ambient temperature overnight. The reaction mixture was extracted with ethyl acetate and the combined organic phases were washed with aqueous sodium bicarbonate solution and brine. The ethyl acetate phase was dried and the solvent was evaporated to yield the product as light brown viscous oil (51 mg, 97%) which was used without any further purification. MS: M=175.2 $(M+H)^+$

Step 6: 6-Cyclopropyl-3-(pyrimidin-5-ylamino)-pyridine-2-carboxylic acid (1-methyl-5-pyridin-2-yl-1H-pyrazol-3-yl)-amide According to the method described in example 62, the title compound was obtained starting from A-5 and 1-methyl-5-pyridin-2-yl-1H-pyrazole-3-ylamine as precipitated light yellow solid in 87% yield. MS: M=413.3 $(M+H)^+$

Example 64

6-Cyclopropyl-3-(pyrimidin-5-ylamino)-pyridine-2-carboxylic acid (5-pyridin-2-yl-[1,3,4]oxadiazol-2-yl)-amide

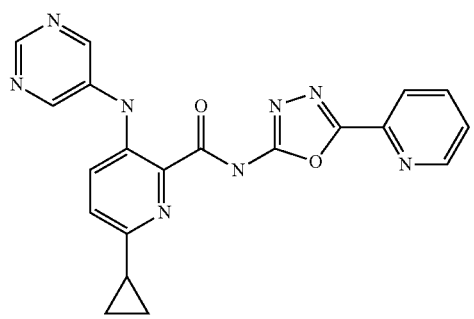 [SMILES: O=C(Nc1nnc(-c2ccccn2)o1)c1nc(C2CC2)ccc1Nc1cncnc1]

According to the method described in example 62, the title compound was obtained starting from A-5 and 5-pyridin-2-yl-[1,3,4]oxadiazol-2-ylamine after preparative HPLC purification and trituration with ethyl acetate as light brown solid in 17% yield.

MS: M=401.3 $(M+H)^+$

Example 65

6-Cyclopropyl-3-(pyrimidin-5-ylamino)-pyridine-2-carboxylic acid (1-pyridin-2-yl-1H-pyrazol-4-yl)-amide

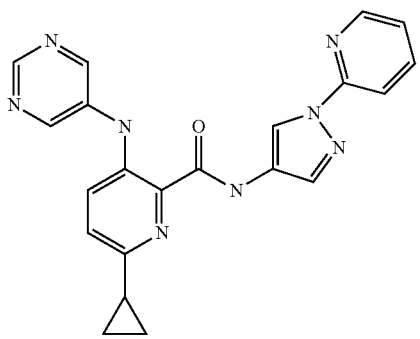 [SMILES: O=C(Nc1cnn(-c2ccccn2)c1)c1nc(C2CC2)ccc1Nc1cncnc1]

Step 1: 1-Pyridin-2-yl-1H-pyrazol-4-carboxylic acid ethyl ester

A solution of 1H-pyrazol-4-carboxylic acid ethyl ester (1.25 g, 8.9 mmol), 2-chloropyridine (2.02 g, 17.8 mmol) and cesium carbonate (8.7 g, 26.75 mmol) in DMF (26.8 ml) was irradiated under microwave conditions at 180° C. for 10 min. The reaction mixture was extracted with diethylether, and the combined organic phases were washed with water and brine. The product was obtained after silica gel chromatography using a heptane/ethyl acetate gradient as white solid (0.81 mg, 42%). MS: M=218.2 $(M+H)^+$ Step 2: 1-Pyridin-2-yl-1H-pyrazol-4-carboxylic acid Pyridin-2-yl-1H-pyrazol-4-carboxylic acid ethyl ester (0.81 g, 3.73 mmol) was dissolved in a THF/ethanol (50 ml/10 ml) mixture, cooled to 0° C. and treated with lithium hydroxide (11.2 ml, 1N aqueous solution). The reaction mixture was allowed to warm-up to ambient temperature and subsequently stirred at that temperature for 7 h. The reaction mixture was extracted with dichloromethane (4×100 ml) and the combined organic phases were dried and evaporated to yield the product as white solid (0.68 g, 96%) which was used without any further purification.
MS: M=188.2 (M−H)⁻

Step 3: (1-Pyridin-2-yl-1H-pyrazol-4-yl)-carbamic acid tert-butyl ester

A solution of 1-pyridin-2-yl-1H-pyrazol-4-carboxylic acid (200 mg, 1.06 mmol) in tert-butanol (4.0 ml) was treated with diphenylphosphoryl azide (240 µl, 1.06 mmol) and triethylamine (300 µl, 2.12 mmol) and stirred at 90° C. for 3 hours. The solvent was removed and the crude product was purified by silica gel chromatography using a heptane/ethyl acetate gradient to yield the product as light yellow solid (190 mg, 69%). MS: M=261.1 (M+H)⁺

Step 4: 1-Pyridin-2-yl-1H-pyrazol-4-ylamine

A solution of (1-pyridin-2-yl-1H-pyrazol-4-yl)-carbamic acid tert-butyl ester (185 mg, 0.72 mmol) in dioxane (1.85 ml) was treated with 4M HCl in dioxane (1.85 ml) and the resulting suspension was stirred at ambient temperature for 2 hours. The reaction mixture was adjusted to basic pH with sodium hydroxide (20 ml, 0.5M aqueous solution) and extracted with dichloromethane. The combined organic phases were dried and the solvent was evaporated to yield the product as light brown solid (110 mg, 96%) which was used without any further purification. MS: M=161.3 (M+H)⁺

Step 5: 6-Cyclopropyl-3-(pyrimidin-5-ylamino)-pyridine-2-carboxylic acid-(1-pyridin-2-yl-1H-pyrazol-4-yl)-amide According to the method described in example 62, the title compound was obtained starting from A-5 and 1-pyridin-2-yl-1H-pyrazol-4-ylamine as precipitated light yellow solid in 24% yield. MS: M=399.2 (M+H)⁺

Example 66

6-Cyclopropyl-3-(pyrimidin-5-ylamino)-pyrazine-2-carboxylic acid (1-pyridin-2-yl-1H-imidazol-4-yl)-amide

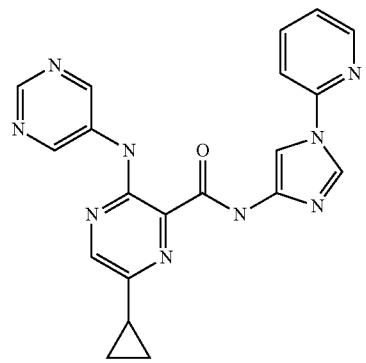 [SMILES: O=C(Nc1cn(-c2ccccn2)cn1)c1nc(C2CC2)cnc1Nc1cncnc1]

According to the method described in example 62, the title compound was obtained starting from A-7 and 1-pyridin-2-yl-1H-imidazol-4-ylamine (~0.2 M THF solution; example 52, step 2) after preparative HPLC purification as brown solid in 2% yield. MS: M=400.1 (M+H)⁺

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

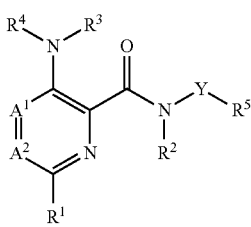

wherein $A^1$ and $A^2$ are each independently selected from the group consisting of CH and N, provided that $A^1$ and $A^2$ are not simultaneously N;

$R^1$ is lower alkyl, lower alkoxy, lower hydroxyalkyl, lower haloalkyl, lower alkoxy lower alkyl, acetyl, lower alkyl-C(O)—, cyano, halogen, amino optionally substituted by 1 or 2 lower alkyl or lower alkoxy lower alkyl, cycloalkyl, or heterocyclyl;

$R^2$ and $R^3$ are each independently hydrogen or lower alkyl;

$R^4$ is heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl;

Y is 5-membered heteroaryl selected from the group consisting of:

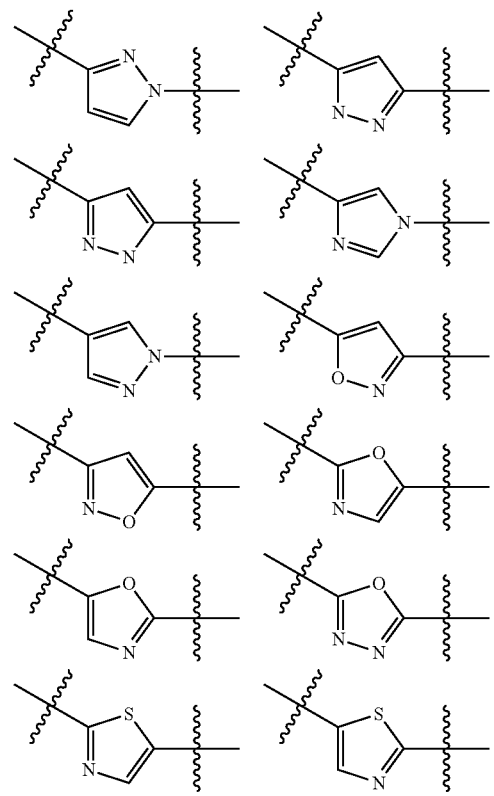

-continued

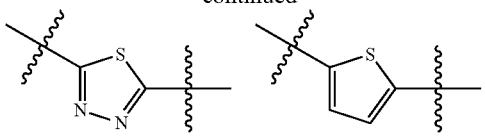

wherein said heteroaryl is optionally substituted by one substituent selected from the group consisting of
  lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COOH, COO-lower alkyl, oxo, cyano and heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl,
  cycloalkyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, and
  heterocyclyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl; and
  $R^5$ is selected from the group consisting of aryl and heteroaryl, wherein said aryl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl,
or a pharmaceutically acceptable salt thereof.

2. The compound of claim 1, wherein $R^1$ is lower alkyl, cycloalkyl, or lower alkoxy lower alkyl.

3. The compound of claim 1, wherein $R^2$ and $R^3$ are hydrogen.

4. The compound of claim 1, wherein $R^4$ is pyrimidinyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl.

5. The compound of claim 1, wherein $R^5$ is phenyl or 6- or 10-membered heteroaryl containing one or two nitrogen, wherein said phenyl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl.

6. The compound of claim 5, wherein 6- or 10-membered heteroaryl is pyridinyl, pyrazinyl, or quinolinyl.

7. The compound of claim 1, wherein Y is selected from the group consisting of:

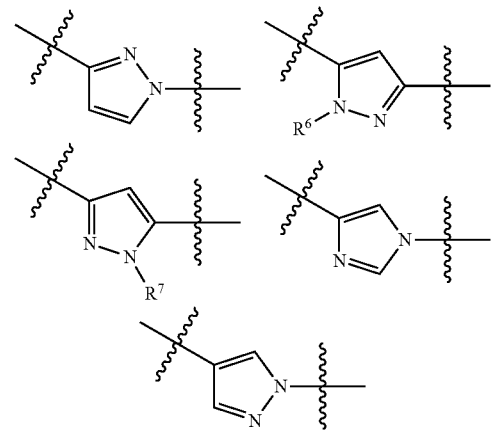

wherein $R^6$ is selected from the group consisting of lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COO-lower alkyl, cyano and heteroaryl optionally substituted by lower alkyl,
  cycloalkyl, and
  heterocyclyl optionally substituted by 1 to 3 substituents selected from the group consisting of lower alkyl, and
  $R^7$ is lower alkyl or lower alkyl substituted by amino optionally substituted by one or two lower alkyl.

8. The compound of claim 6, wherein Y is selected from the group consisting of:

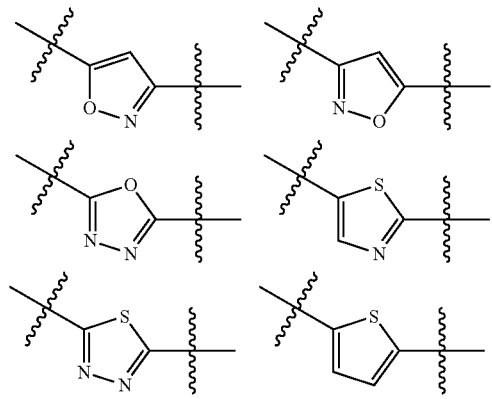

9. The compound of claim 1, selected from the group consisting of:
  6-Methyl-3-(pyrimidin-5-ylamino)-pyridine-2-carboxylic acid (1-phenyl-1H-pyrazol-3-yl)-amide,
  6-Methyl-3-(pyrimidin-5-ylamino)-pyridine-2-carboxylic acid [1-(4-fluoro-phenyl)-1H-pyrazol-3-yl]-amide,
  6-Methyl-3-(pyrimidin-5-ylamino)-pyridine-2-carboxylic acid [1-(2-fluoro-phenyl)-1H-pyrazol-3-yl]-amide,
  6-Methyl-3-(pyrimidin-5-ylamino)-pyridine-2-carboxylic acid (1-pyridin-2-yl-1H-pyrazol-3-yl)-amide,
  6-Methyl-3-(pyrimidin-5-ylamino)-pyridine-2-carboxylic acid (1-pyridin-4-yl-1H-pyrazol-3-yl)-amide,
  6-Cyclopropyl-3-(pyrimidin-5-ylamino)-pyridine-2-carboxylic acid [1-(4-fluoro-phenyl)-1H-pyrazol-3-yl]-amide, 6-Cyclopropyl-3-(pyrimidin-5-ylamino)-pyridine-2-carboxylic acid (1-pyridin-4-yl-1H-pyrazol-3-yl)-amide,
6-Cyclopropyl-3-(pyrimidin-5-ylamino)-pyridine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [2-(2-hydroxy-ethyl)-5-phenyl-2H-pyrazol-3-yl]-amide, and
6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide or a pharmaceutically acceptable salt thereof.

10. The compound of claim 1, selected from the group consisting of:
6-Methoxymethyl-3-(pyrimidin-5-ylamino)-pyridine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(2-dimethylamino-ethyl)-5-pyridin-2-yl-2H-pyrazol-3-yl]-amide,
2-Methoxymethyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid (2-cyclohexyl-5-pyridin-2-yl-2H-pyrazol-3-yl)-amide,
(5-{[6-Cyclopropyl-3-(pyrimidin-5-ylamino)-pyridine-2-carbonyl]-amino}-3-pyridin-2-yl-pyrazol-1-yl)-acetic acid ethyl ester,
6-Cyclopropyl-3-(pyrimidin-5-ylamino)-pyridine-2-carboxylic acid [2-(2-morpholin-4-yl-ethyl)-5-pyridin-2-yl-2H-pyrazol-3-yl]-amide,
6-Cyclopropyl-3-(pyrimidin-5-ylamino)-pyridine-2-carboxylic acid (2-phenethyl-5-pyridin-2-yl-2H-pyrazol-3-yl)-amide,
6-Cyclopropyl-3-(pyrimidin-5-ylamino)-pyridine-2-carboxylic acid (2-tert-butyl-5-pyridin-2-yl-2H-pyrazol-3-yl)-amide,
6-Ethyl-3-(pyrimidin-5-ylamino)-pyridine-2-carboxylic acid (2-methyl-5-pyridin-2-yl-2H-pyrazol-3-yl)-amide, and
6-Cyclopropyl-3-(pyrimidin-5-ylamino)-pyridine-2-carboxylic acid [5-pyridin-2-yl-2-(tetrahydro-pyran-4-yl)-2H-pyrazol-3-yl]-amide or a pharmaceutically acceptable salt thereof.

11. The compound of claim 1, selected from the group consisting of:
6-Cyclopropyl-3-(pyrimidin-5-ylamino)-pyrazine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [5-pyridin-2-yl-2-(2,2,2-trifluoro-ethyl)-2H-pyrazol-3-yl]-amide,
6-Cyclopropyl-3-(pyrimidin-5-ylamino)-pyridine-2-carboxylic acid (2-propyl-5-pyridin-2-yl-2H-pyrazol-3-yl)-amide,
6-Cyclopropyl-3-(pyrimidin-5-ylamino)-pyridine-2-carboxylic acid [5-(6-chloro-pyridin-2-yl)-2-(2-hydroxy-ethyl)-2H-pyrazol-3-yl]-amide,
6-Cyclopropyl-3-(pyrimidin-5-ylamino)-pyridine-2-carboxylic acid [2-(2-hydroxy-ethyl)-5-quinolin-2-yl-2H-pyrazol-3-yl]-amide,
6-Cyclopropyl-3-(pyrimidin-5-ylamino)-pyridine-2-carboxylic acid [5-(5-chloro-pyridin-2-yl)-2-(2-hydroxy-ethyl)-2H-pyrazol-3-yl]-amide,
6-Cyclopropyl-3-(pyrimidin-5-ylamino)-pyridine-2-carboxylic acid (2-isopropyl-5-pyridin-2-yl-2H-pyrazol-3-yl)-amide,
6-Cyclopropyl-3-(pyrimidin-5-ylamino)-pyridine-2-carboxylic acid (2-isobutyl-5-pyridin-2-yl-2H-pyrazol-3-yl)-amide,
6-Cyclopropyl-3-(pyrimidin-5-ylamino)-pyridine-2-carboxylic acid (2-benzyl-5-pyridin-2-yl-2H-pyrazol-3-yl)-amide, and
6-Cyclopropyl-3-(pyrimidin-5-ylamino)-pyridine-2-carboxylic acid (2-ethyl-5-pyridin-2-yl-2H-pyrazol-3-yl)-amide or a pharmaceutically acceptable salt thereof.

12. The compound of claim 1, selected from the group consisting of:
6-Cyclopropyl-3-(pyrimidin-5-ylamino)-pyridine-2-carboxylic acid (2-cyclopentylmethyl-5-pyridin-2-yl-2H-pyrazol-3-yl)-amide,
6-Cyclopropyl-3-(pyrimidin-5-ylamino)-pyridine-2-carboxylic acid (2-cyclohexylmethyl-5-pyridin-2-yl-2H-pyrazol-3-yl)-amide,
6-Cyclopropyl-3-(pyrimidin-5-ylamino)-pyridine-2-carboxylic acid [2-(2-cyano-ethyl)-5-pyridin-2-yl-2H-pyrazol-3-yl]-amide,
6-Ethyl-3-(pyrimidin-5-ylamino)-pyridine-2-carboxylic acid [2-(2-hydroxy-ethyl)-5-pyridin-2-yl-2H-pyrazol-3-yl]-amide,
6-Methyl-3-(pyrimidin-5-ylamino)-pyrazine-2-carboxylic acid (2-methyl-5-pyridin-2-yl-2H-pyrazol-3-yl)-amide,
6-Methyl-3-(pyrimidin-5-ylamino)-pyrazine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(3-methyl-3H-imidazol-4-ylmethyl)-5-pyridin-2-yl-2H-pyrazol-3-yl]-amide,
6-Cyclopropyl-3-(pyrimidin-5-ylamino)-pyridine-2-carboxylic acid [2-(2-methoxy-ethyl)-5-pyridin-2-yl-2H-pyrazol-3-yl]-amide,
6-Cyclopropyl-3-(pyrimidin-5-ylamino)-pyridine-2-carboxylic acid [5-(5-chloro-pyridin-2-yl)-2-methyl-2H-pyrazol-3-yl]-amide, and
6-Cyclopropyl-3-(pyrimidin-5-ylamino)-pyridine-2-carboxylic acid (2-methyl-5-quinolin-2-yl-2H-pyrazol-3-yl)-amide or a pharmaceutically acceptable salt thereof.

13. The compound of claim 1, selected from the group consisting of:
6-Cyclopropyl-3-(pyrimidin-5-ylamino)-pyridine-2-carboxylic acid [5-(6-chloro-pyridin-2-yl)-2-methyl-2H-pyrazol-3-yl]-amide,
6-Cyclopropyl-3-(pyrimidin-5-ylamino)-pyridine-2-carboxylic acid [1-(2-dimethylamino-ethyl)-5-pyridin-2-yl-1H-pyrazol-3-yl]-amide,
6-Cyclopropyl-3-(pyrimidin-5-ylamino)-pyridine-2-carboxylic acid [2-(1-methyl-piperidin-4-yl)-5-pyridin-2-yl-2H-pyrazol-3-yl]-amide,
6-Cyclopropyl-3-(pyrimidin-5-ylamino)-pyridine-2-carboxylic acid [5-(4-methoxy-phenyl)-[1,3,4]thiadiazol-2-yl]-amide,
6-Cyclopropyl-3-(pyrimidin-5-ylamino)-pyridine-2-carboxylic acid [5-(4-fluoro-phenyl)-[1,3,4]thiadiazol-2-yl]-amide,
6-Cyclopropyl-3-(pyrimidin-5-ylamino)-pyridine-2-carboxylic acid (3-phenyl-isoxazol-5-yl)-amide,
6-Cyclopropyl-3-(pyrimidin-5-ylamino)-pyridine-2-carboxylic acid (5-phenyl-isoxazol-3-yl)-amide, 6-Cyclopropyl-3-(pyrimidin-5-ylamino)-pyridine-2-carboxylic acid (5-phenyl-[1,3,4]thiadiazol-2-yl)-amide,
6-Cyclopropyl-3-(pyrimidin-5-ylamino)-pyridine-2-carboxylic acid (5-pyrazin-2-yl-[1,3,4]thiadiazol-2-yl)-amide, and
6-Cyclopropyl-3-(pyrimidin-5-ylamino)-pyridine-2-carboxylic acid (5-pyridin-2-yl-thiophen-2-yl)-amide
or a pharmaceutically acceptable salt thereof.

14. The compound of claim 1, selected from the group consisting of:
6-Cyclopropyl-3-(pyrimidin-5-ylamino)-pyridine-2-carboxylic acid (3-pyridin-2-yl-isoxazol-5-yl)-amide,
6-Cyclopropyl-3-(pyrimidin-5-ylamino)-pyridine-2-carboxylic acid (1-pyridin-2-yl-1H-imidazol-4-yl)-amide,
2-Isopropyl-5-(pyrimidin-5-ylamino)-pyrimidine-4-carboxylic acid (2-methyl-5-pyridin-2-yl-2H-pyrazol-3-yl)-amide,
2-Cyclopropyl-5-(pyrimidin-5-ylamino)-pyrimidine-4-carboxylic acid (2-methyl-5-pyridin-2-yl-2H-pyrazol-3-yl)-amide,
2-tert-Butyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [3-(4-chloro-phenyl)-isoxazol-5-yl]-amide,
6-Cyclopropyl-3-(pyrimidin-5-ylamino)-pyridine-2-carboxylic acid [3-(4-bromo-phenyl)-isoxazol-5-yl]-amide,
6-Cyclopropyl-3-(pyrimidin-5-ylamino)-pyridine-2-carboxylic acid [3-(4-fluoro-phenyl)-isoxazol-5-yl]-amide,
6-Methoxymethyl-3-(pyrimidin-5-ylamino)-pyridine-2-carboxylic acid (2-methyl-5-pyridin-2-yl-2H-pyrazol-3-yl)-amide, and
2-Cyclohexyl-5-(pyrimidin-5-ylamino)-pyrimidine-4-carboxylic acid (2-methyl-5-pyridin-2-yl-2H-pyrazol-3-yl)-amide
or a pharmaceutically acceptable salt thereof.

15. The compound of claim 1, selected from the group consisting of:
2-Isobutyl-5-(pyrimidin-5-ylamino)-pyrimidine-4-carboxylic acid (2-methyl-5-pyridin-2-yl-2H-pyrazol-3-yl)-amide,
6-Cyclopropyl-3-(pyrimidin-5-ylamino)-pyridine-2-carboxylic acid (2-pyridin-2-yl-thiazol-5-yl)-amide,
6-Cyclopropyl-3-(pyrimidin-5-ylamino)-pyridine-2-carboxylic acid (1-methyl-5-pyridin-2-yl-1H-pyrazol-3-yl)-amide,
6-Cyclopropyl-3-(pyrimidin-5-ylamino)-pyridine-2-carboxylic acid (5-pyridin-2-yl-[1,3,4]oxadiazol-2-yl)-amide,
6-Cyclopropyl-3-(pyrimidin-5-ylamino)-pyridine-2-carboxylic acid (1-pyridin-2-yl-1H-pyrazol-4-yl)-amide, and
6-Cyclopropyl-3-(pyrimidin-5-ylamino)-pyrazine-2-carboxylic acid (1-pyridin-2-yl-1H-imidazol-4-yl)-amide,
or a pharmaceutically acceptable salt thereof.

16. The compound of claim 1, selected from the group consisting of
6-Cyclopropyl-3-(pyrimidin-5-ylamino)-pyridine-2-carboxylic acid [1-(4-fluoro-phenyl)-1H-pyrazol-3-yl]-amide,
6-Cyclopropyl-3-(pyrimidin-5-ylamino)-pyridine-2-carboxylic acid (2-methyl-5-pyridin-2-yl-2H-pyrazol-3-yl)-amide,
6-Cyclopropyl-3-(pyrimidin-5-ylamino)-pyridine-2-carboxylic acid [2-(2-hydroxy-ethyl)-5-pyridin-2-yl-2H-pyrazol-3-yl]-amide,
6-Methoxymethyl-3-(pyrimidin-5-ylamino)-pyridine-2-carboxylic acid [2-(2-hydroxy-ethyl)-5-pyridin-2-yl-2H-pyrazol-3-yl]-amide,
6-Cyclopropyl-3-(pyrimidin-5-ylamino)-pyridine-2-carboxylic acid [2-(2-dimethylamino-ethyl)-5-pyridin-2-yl-2H-pyrazol-3-yl]-amide,
6-Cyclopropyl-3-(pyrimidin-5-ylamino)-pyridine-2-carboxylic acid [2-(2-morpholin-4-yl-ethyl)-5-pyridin-2-yl-2H-pyrazol-3-yl]-amide,
6-Cyclopropyl-3-(pyrimidin-5-ylamino)-pyridine-2-carboxylic acid [5-pyridin-2-yl-2-(tetrahydro-pyran-4-yl)-2H-pyrazol-3-yl]-amide,
6-Cyclopropyl-3-(pyrimidin-5-ylamino)-pyrazine-2-carboxylic acid (2-methyl-5-pyridin-2-yl-2H-pyrazol-3-yl)-amide,
6-Ethyl-3-(pyrimidin-5-ylamino)-pyridine-2-carboxylic acid [2-(2-hydroxy-ethyl)-5-pyridin-2-yl-2H-pyrazol-3-yl]-amide, and
6-Methyl-3-(pyrimidin-5-ylamino)-pyrazine-2-carboxylic acid [2-(2-hydroxy-ethyl)-5-pyridin-2-yl-2H-pyrazol-3-yl]-amide
or a pharmaceutically acceptable salt thereof.

17. The compound of claim 1, selected from the group consisting of
6-Cyclopropyl-3-(pyrimidin-5-ylamino)-pyridine-2-carboxylic acid [2-(2-methoxy-ethyl)-5-pyridin-2-yl-2H-pyrazol-3-yl]-amide,
6-Cyclopropyl-3-(pyrimidin-5-ylamino)-pyridine-2-carboxylic acid [5-(5-chloro-pyridin-2-yl)-2-methyl-2H-pyrazol-3-yl]-amide,
6-Cyclopropyl-3-(pyrimidin-5-ylamino)-pyridine-2-carboxylic acid (5-pyridin-2-yl-thiophen-2-yl)-amide,
6-Cyclopropyl-3-(pyrimidin-5-ylamino)-pyridine-2-carboxylic acid (3-pyridin-2-yl-isoxazol-5-yl)-amide,
6-Cyclopropyl-3-(pyrimidin-5-ylamino)-pyridine-2-carboxylic acid (1-pyridin-2-yl-1H-imidazol-4-yl)-amide,
2-tert-Butyl-5-(pyrimidin-5-ylamino)-pyrimidine-4-carboxylic acid (2-methyl-5-pyridin-2-yl-2H-pyrazol-3-yl)-amide,
6-Methoxymethyl-3-(pyrimidin-5-ylamino)-pyridine-2-carboxylic acid (2-methyl-5-pyridin-2-yl-2H-pyrazol-3-yl)-amide,
2-Isobutyl-5-(pyrimidin-5-ylamino)-pyrimidine-4-carboxylic acid (2-methyl-5-pyridin-2-yl-2H-pyrazol-3-yl)-amide, and
6-Cyclopropyl-3-(pyrimidin-5-ylamino)-pyridine-2-carboxylic acid (2-pyridin-2-yl-thiazol-5-yl)-amide,
or a pharmaceutically acceptable salt thereof.

18. A pharmaceutical composition comprising a therapeutically effectively amount of a compound of formula I

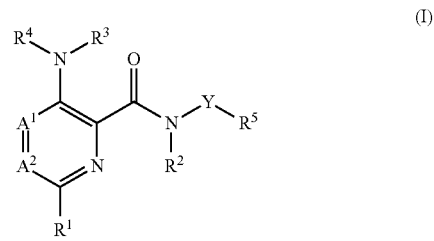

(I)

wherein
- $A^1$ and $A^2$ are each independently selected from the group consisting of CH and N, provided that $A^1$ and $A^2$ are not simultaneously N;
- $R^1$ is lower alkyl, lower alkoxy, lower hydroxyalkyl, lower haloalkyl, lower alkoxy lower alkyl, acetyl, lower alkyl-C(O)—, cyano, halogen, amino optionally substituted by 1 or 2 lower alkyl or lower alkoxy lower alkyl, cycloalkyl, or heterocyclyl;
- $R^2$ and $R^3$ are each independently hydrogen or lower alkyl;
- $R^4$ is heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl;
- Y is 5-membered heteroaryl selected from the group consisting of:

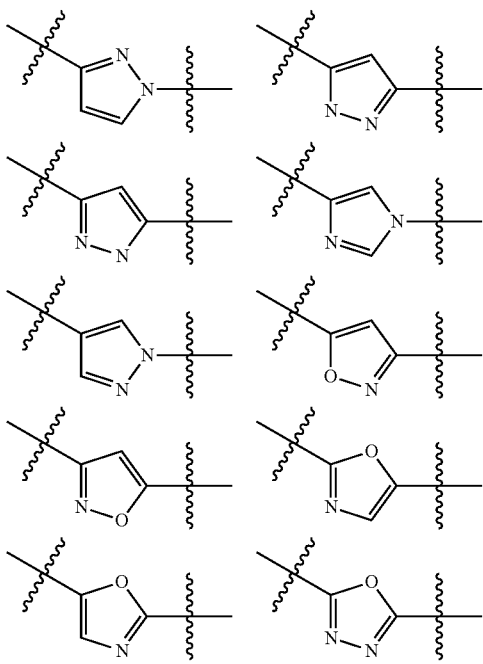

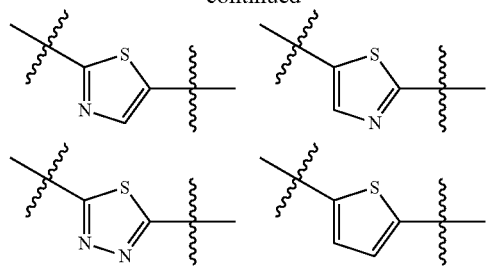

wherein said heteroaryl is optionally substituted by one substituent selected from the group consisting of
- lower alkyl, which is optionally substituted by 1 to 3 substituents selected from the group consisting of aryl, cycloalkyl, heterocyclyl, lower alkoxy, hydroxyl, halogen, amino optionally substituted by one or two lower alkyl, COOH, COO-lower alkyl, oxo, cyano and heteroaryl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl,
- cycloalkyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, and
- heterocyclyl optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl; and
- $R^5$ is selected from the group consisting of aryl and heteroaryl, wherein said aryl and said heteroaryl are optionally substituted by 1 to 3 substituents selected from the group consisting of hydroxyl, halogen, lower alkyl, lower alkoxy, lower hydroxyalkyl, lower haloalkyl, lower alkoxy lower alkyl, acetyl, cyano and amino optionally substituted by 1 or 2 lower alkyl or lower alkoxy lower alkyl, or a pharmaceutically acceptable salt thereof and a pharmaceutically acceptable carrier.

* * * * *